US 12,186,386 B2
(12) United States Patent
Moore et al.

(10) Patent No.: US 12,186,386 B2
(45) Date of Patent: Jan. 7, 2025

(54) RECOMBINANT RSV WITH SILENT MUTATIONS, VACCINES, AND METHODS RELATED THERETO

(71) Applicants: Emory University, Atlanta, GA (US); Children's Healthcare of Atlanta, Inc., Atlanta, GA (US)

(72) Inventors: Martin L. Moore, Decatur, GA (US); Jia Meng, Atlanta, GA (US); Anne Hotard, Atlanta, GA (US); Elizabeth Littauer, Decatur, GA (US); Christopher Stobart, Decatur, GA (US)

(73) Assignee: Emory University and Children's Healthcare of Atlanta, Inc., Atlanta, GA (US)

( * ) Notice: Subject to any disclaimer, the term of this patent is extended or adjusted under 35 U.S.C. 154(b) by 0 days.

(21) Appl. No.: 18/046,743

(22) Filed: Oct. 14, 2022

(65) Prior Publication Data

US 2023/0302115 A1  Sep. 28, 2023

Related U.S. Application Data

(60) Continuation of application No. 17/025,568, filed on Sep. 18, 2020, now Pat. No. 11,471,524, which is a continuation of application No. 16/263,915, filed on Jan. 31, 2019, now Pat. No. 10,792,356, which is a division of application No. 14/775,671, filed as application No. PCT/US2014/027447 on Mar. 14, 2014, now Pat. No. 10,232,032.

(60) Provisional application No. 61/890,500, filed on Oct. 14, 2013, provisional application No. 61/781,228, filed on Mar. 14, 2013.

(51) Int. Cl.
| | |
|---|---|
| *A61K 39/155* | (2006.01) |
| *A61K 39/12* | (2006.01) |
| *A61K 45/06* | (2006.01) |
| *C07K 14/005* | (2006.01) |
| *C12N 7/00* | (2006.01) |
| *A61K 39/00* | (2006.01) |

(52) U.S. Cl.
CPC ............ *A61K 39/155* (2013.01); *A61K 39/12* (2013.01); *A61K 45/06* (2013.01); *C07K 14/005* (2013.01); *C12N 7/00* (2013.01); *A61K 2039/5254* (2013.01); *A61K 2039/55* (2013.01); *A61K 2039/58* (2013.01); *C12N 2760/18522* (2013.01); *C12N 2760/18534* (2013.01); *C12N 2760/18562* (2013.01); *C12N 2800/22* (2013.01)

(58) Field of Classification Search
None
See application file for complete search history.

(56) References Cited

U.S. PATENT DOCUMENTS

| | | |
|---|---|---|
| 5,618,682 A | 4/1997 | Scheirer |
| 5,674,713 A | 10/1997 | Mcelroy et al. |
| 5,922,326 A | 7/1999 | Murphy et al. |
| 5,976,796 A | 11/1999 | Szalay et al. |
| 5,993,824 A | 11/1999 | Murphy et al. |
| 6,033,886 A | 3/2000 | Conzelmann |
| 6,074,859 A | 6/2000 | Hirokawa et al. |
| 6,214,805 B1 | 4/2001 | Torrence et al. |
| 6,264,957 B1 | 7/2001 | Collins |
| 6,689,367 B1 | 2/2004 | Collins et al. |
| 6,699,476 B1 | 3/2004 | Collins et al. |
| 6,713,066 B1 | 3/2004 | Collins et al. |
| 6,790,449 B2 | 9/2004 | Collins |
| 6,923,971 B2 | 8/2005 | Krempl et al. |
| 7,465,574 B2 | 12/2008 | Jin et al. |
| 7,485,440 B2 | 2/2009 | Collins et al. |
| 7,572,904 B2 | 8/2009 | Cheng et al. |
| 7,744,902 B2 | 6/2010 | Krempl et al. |
| 7,846,455 B2 | 12/2010 | Collins et al. |
| 7,951,384 B2 | 5/2011 | Morrison et al. |
| 8,163,530 B2 | 4/2012 | Cheng et al. |
| 8,580,270 B2 | 11/2013 | Morrison |

(Continued)

FOREIGN PATENT DOCUMENTS

| | | |
|---|---|---|
| CA | 2905571 | 9/2014 |
| CN | 105214080 | 1/2016 |

(Continued)

OTHER PUBLICATIONS

Boyapalle S, et al., PLoS One 7(2): e29386 (Year: 2012).*
Coleman JR et al.,Virus attenuation by genome-scale changes in codon pair bias. Science. Jun. 27, 2008;320(5884):1784-7 (Year: 2008).*
International Search Report and Written Opinion issued for Application No. PCT/US2016/058976, dated Apr. 6, 2017, 11 pages.

(Continued)

*Primary Examiner* — Shanon A. Foley
*Assistant Examiner* — Myron G Hill
(74) *Attorney, Agent, or Firm* — Meunier Carlin & Curfman LLC

(57) ABSTRACT

In certain embodiments, the disclosure relates to the polynucleotide sequences of respiratory syncytial virus (RSV). In certain embodiments, the disclosure relates to isolated or recombinant nucleic acids and polypeptides comprising desirable nucleic acid sequences and mutations disclosed herein. In certain embodiments, isolated or recombinant RSV comprising the nucleic acids and polypeptides disclosed herein (e.g., attenuated recombinant RSV) are also provided, as are immunogenic compositions including such nucleic acids, polypeptides, and RSV genomes that are suitable for use as vaccines. Attenuated or killed RSV containing these nucleic acids and mutation in the form of copied nucleic acids (e.g., cDNAs) are also contemplated.

6 Claims, 15 Drawing Sheets

Specification includes a Sequence Listing.

(56) References Cited

U.S. PATENT DOCUMENTS

| | | |
|---|---|---|
| 8,772,256 B2 | 7/2014 | Graham |
| 8,846,051 B2 | 9/2014 | Kew et al. |
| 9,011,876 B2 | 4/2015 | Yagodich et al. |
| 9,107,939 B2 | 8/2015 | Luytjes et al. |
| 9,476,032 B2 | 10/2016 | Wimmer et al. |
| 9,492,525 B2 | 11/2016 | Fattom et al. |
| 9,624,375 B2 | 4/2017 | Wonneberger et al. |
| 10,232,032 B2 * | 3/2019 | Moore .............. A61K 45/06 |
| 10,792,356 B2 * | 10/2020 | Moore .............. A61K 39/155 |
| 11,471,524 B2 * | 10/2022 | Moore .............. A61P 11/00 |
| 2008/0118530 A1 | 5/2008 | Kew et al. |
| 2009/0285853 A1 | 11/2009 | Cheng et al. |
| 2012/0264217 A1 | 10/2012 | Moore et al. |
| 2014/0271699 A1 | 9/2014 | Kwong et al. |
| 2014/0356390 A1 | 12/2014 | Kew et al. |
| 2015/0368622 A1 | 12/2015 | Collins et al. |
| 2018/0333477 A1 | 11/2018 | Moore et al. |

FOREIGN PATENT DOCUMENTS

| | | |
|---|---|---|
| WO | 0189562 | 11/2001 |
| WO | 2006042156 | 4/2006 |
| WO | 2008121992 | 10/2008 |
| WO | 2010053883 | 5/2010 |
| WO | 2012158613 | 11/2012 |
| WO | 2014124238 | 8/2014 |
| WO | 2014152534 | 9/2014 |
| WO | 2014160463 | 10/2014 |

OTHER PUBLICATIONS

International Preliminary Report on Patentability issued for Application No. PCT/US2016/058976, dated May 11, 2018.
Extended European Search Report issued for Application No. 16860742.2, dated May 7, 2019.
Burns, Cara Carthel, et al. "Modulation of poliovirus replicative fitness in HeLa cells by deoptimization of synonymous codon usage in the capsid region." Journal of virology 80.7 (2006): 3259-3272.
Clements, Mary Lou, et al. "Evaluation of bovine, cold-adapted human, and wild-type human parainfluenza type 3 viruses in adult volunteers and in chimpanzees." Journal of clinical microbiology 29.6 (1991): 1175-1182.
Collins, Peter L., and José A. Melero. "Progress in understanding and controlling respiratory syncytial virus: still crazy after all these years." Virus research 162.1-2 (2011): 80-99.
Collins, Peter L., et al. "Gene overlap and site-specific attenuation of transcription of the viral polymerase L gene of human respiratory syncytial virus." Proceedings of the National Academy of Sciences 84.15 (1987): 5134-5138.
Collins, Peter L., et al. "Nucleotide sequences for the gene junctions of human respiratory syncytial virus reveal distinctive features of intergenic structure and gene order." Proceedings of the National Academy of Sciences 83.13 (1986): 4594-4598.
Collins, Peter L., et al. "Production of infectious human respiratory syncytial virus from cloned cDNA confirms an essential role for the transcription elongation factor from the 5'proximal open reading frame of the M2 mRNA in gene expression and provides a capability for vaccine development." Proceedings of the National Academy of Sciences 92.25 (1995): 11563-11567.
DeWet, J. R., et al. "Subramani (1987)." Firefly luciferase gene: structure and expression in mammalian cells. Mol. Cell. Biol 7.725-737.
Glenn, Gregory M., et al. "A randomized, blinded, controlled, dose-ranging study of a respiratory syncytial virus recombinant fusion (F) nanoparticle vaccine in healthy women of childbearing age." The Journal of infectious diseases 213.3 (2015): 411-422.
Hotard et al. A stabilized respiratory syncytial virus reverse genetics system amenable to recombination-mediated mutagenesis. Virology 434, 129-136 (2012).
Hotard et al. Identification of residues in the human respiratory syncytial virus fusion protein that modulate fusion activity and pathogenesis. J Virol 89, 512-522 (2015).
Hotard, Anne L., et al. "Functional analysis of the 60-nucleotide duplication in the respiratory syncytial virus Buenos Aires strain attachment glycoprotein." Journal of virology 89.16 (2015): 8258-8266.
Iyer, Vidyashankara, et al. "Impact of formulation and particle size on stability and immunogenicity of oil-in-water emulsion adjuvants." Human vaccines & immunotherapeutics 11.7 (2015): 1853-1864.
Johnson, Philip R., et al. "The G glycoprotein of human respiratory syncytial viruses of subgroups A and B: extensive sequence divergence between antigenically related proteins." Proceedings of the National Academy of Sciences 84.16 (1987): 5625-5629.
Karron, R. A., et al. "A gene deletion that up-regulates viral gene expression yields an attenuated RSV vaccine with improved antibody responses in children. Sci Transl Med 7: 312ra175." (2015).
Karron, Ruth A., et al. "Identification of a recombinant live attenuated respiratory syncytial virus vaccine candidate that is highly attenuated in infants." The Journal of infectious diseases 191.7 (2005): 1093-1104.
Kim, Hyun Wha, et al. "Respiratory syncytial virus disease in infants despite prior administration of antigenic inactivated vaccine." American journal of epidemiology 89.4 (1969): 422-434.
Kim, Hyun Wha, et al. "Safety and antigenicity of temperature sensitive (TS) mutant respiratory syncytial virus (RSV) in infants and children." Pediatrics 52.1 (1973): 56-63.
Lemon, Ken, et al. "Recombinant subgroup B human respiratory syncytial virus expressing enhanced green fluorescent protein efficiently replicates in primary human cells and is virulent in cotton rats." Journal of virology 89.5 (2015): 2849-2856.
Maniatis, Tom, Stephen Goodbourn, and Janice A. Fischer. "Regulation of inducible and tissue-specific gene expression." Science 236.4806 (1987): 1237-1245.
Meng et al. Respiratory Syncytial Virus Attachment Glycoprotein Contribution to Infection Depends on the Specific Fusion Protein. Journal of virology 90, 245-253 (2015).
Meng, Jia, et al. "Refining the balance of attenuation and immunogenicity of respiratory syncytial virus by targeted codon deoptimization of virulence genes." MBio 5.5 (2014): e01704-14.
Merzlyak, Ekaterina M., et al. "Bright monomeric red fluorescent protein with an extended fluorescence lifetime." Nature methods 4.7 (2007): 555.
Mueller, Steffen, et al. "Reduction of the rate of poliovirus protein synthesis through large-scale codon deoptimization causes attenuation of viral virulence by lowering specific infectivity." Journal of virology 80.19 (2006): 9687-9696.
Murphy, Brian R., et al. "Enhanced pulmonary histopathology is observed in cotton rats immunized with formalin-inactivated respiratory syncytial virus (RSV) or purified F glycoprotein and challenged with RSV 3-6 months after immunization." Vaccine 8.5 (1990): 497-502.
NCBI, GenBank Accession No. ACO83297.1, Apr. 20, 2009.
NCBI, GenBank Accession No. U50362.1, Jun. 30, 2004.
Needleman, Saul B., and Christian D. Wunsch. "A general method applicable to the search for similarities in the amino acid sequence of two proteins." Journal of molecular biology 48.3 (1970): 443-453.
Pearson, William R., and David J. Lipman. "Improved tools for biological sequence comparison." Proceedings of the National Academy of Sciences 85.8 (1988): 2444-2448.
Quan, Fu-Shi, et al. "Viruslike particle vaccine induces protection against respiratory syncytial virus infection in mice." Journal of Infectious Diseases 204.7 (2011): 987-995.
Randhawa, J. S., et al. "Nucleotide sequences of the genes encoding the putative attachment glycoprotein (G) of mouse and tissue culture-passaged strains of pneumonia virus of mice." Virology 207.1 (1995): 240-245.
Rostad, Christina A., et al. "A recombinant respiratory syncytial virus vaccine candidate attenuated by a low-fusion F protein is immunogenic and protective against challenge in cotton rats." Journal of virology 90.16 (2016): 7508-7518.

(56) References Cited

OTHER PUBLICATIONS

Shcherbo, Dmitry, et al. "Far-red fluorescent tags for protein imaging in living tissues." Biochemical journal 418.3 (2009): 567-574.
Smith, Temple F., and Michael S. Waterman. "Comparison of biosequences." Advances in applied mathematics 2.4 (1981): 482-489.
Stobart, Christopher C., et al. "Reverse Genetics of Respiratory Syncytial Virus." Human Respiratory Syncytial Virus. Humana Press, New York, NY, 2016. 141-153.
Voss, Stephan D., Uwe Schlokat, and Peter Gruss. "The role of enhancers in the regulation of cell-type-specific transcriptional control." Trends in Biochemical Sciences 11.7 (1986): 287-289.
Walsh, Edward E., et al. "Immunization with glycoprotein subunits of respiratory syncytial virus to protect cotton rats against viral infection." Journal of Infectious Diseases 155.6 (1987): 1198-1204.
Wright, Peter F., et al. "Administration of a highly attenuated, live respiratory syncytial virus vaccine to adults and children." Infection and Immunity37.1 (1982): 397-400.
Wright, Peter F., et al. "Evaluation of a live, attenuated respiratory syncytial virus vaccine in infants." The Journal of pediatrics 88.6 (1976): 931-936.
Office Action issued in Canadian Application No. 2,906,606, dated Jan. 27, 2020.
Written Opinion for Singaporean Application No. 11201803581V, dated Sep. 10, 2019.
Search Report for Singaporean Application No. 11201803581V, dated Sep. 10, 2019.
English Summary Office Action for Chinese Application No. 2014800254152, dated Oct. 8, 2019.
International Search Report in PCT Application No. PCT/US2014/027447 mailed on Aug. 4, 2014 (7 pages).
EMBL: U39661, Respiratory syncytial virus, complete genome. [online] Mar. 29, 1997.
NCBI, GenBank Accession No. ACO83297.1.
NCBI, GenBank Accession No. U50362.1.
Moore, Martin L., et al. "A chimeric A2 strain of respiratory syncytial virus (RSV) with the fusion protein of RSV strain line 19 exhibits enhanced viral load, mucus, and airway dysfunction." Journal of virology 83.9 (2009): 4185-4194.
Coleman, J. Robert, et al. "Virus attenuation by genome-scale changes in codon pair bias." Science 320.5884 (2008): 1784-1787.
Spann, Kirsten M., Kim C. Tran, and Peter L. Collins. "Effects of nonstructural proteins NS1 and NS2 of human respiratory syncytial virus on interferon regulatory factor 3, NF-κB, and proinflammatory cytokines." Journal of virology 79.9 (2005): 5353-5362.
Buchholz, Ursula J., et al. "Deletion of nonstructural proteins NS1 and NS2 from pneumonia virus of mice attenuates viral replication and reduces pulmonary cytokine expression and disease." Journal of virology 83.4 (2009): 1969-1980.
Boyapalle, Sandhya, et al. "Respiratory syncytial virus NS1 protein colocalizes with mitochondrial antiviral signaling protein MAVS following infection." PloS one 7.2 (2012): e29386.
Title: US-14-775-671-SEQ 4 Alignment versus 08-962-690-SEQ12, 17 pages, dated Sep. 28, 2017.
European Search Report in Application No. 14770291.4 mailed on Jan. 23, 2017 (10 pages).
Communication Pursuant to Article 94(3) EPC, in European Application No. 14770291.4, dated Jun. 5, 2018.
First Office Action issued by the Japanese Patent Office, in Application No. 22016-502442, dated Jun. 5, 2018 (6 pages) English Translation Included.
Office Action issued by the Chinese Patent Office, in Application No. 201480025415.2, dated Jun. 27, 2019. English Translation Included.
Office Action issued by the Chinese Patent Office, in Application No. 201480025415.2, dated Oct. 8, 2018. English Translation Included.
First Examination Report issued by the Australian Patent Office, in Application No. 2014239583, dated Jun. 18, 2019.
Second Examination Report issued by the Australian Patent Office, in Application No. 2014239583, dated Jun. 18, 2020.
Office Action issued by the Japanese Patent Office, in Application No. 2019063498, dated Dec. 3, 2019. English Translation Included.
Examination Report issued in Singaporean Application No. 11201803581V dated Dec. 2, 2020.
English translation of Office Action for Japanese Application No. 2018-522569 dated Nov. 4, 2020.
English translation of Preliminary Office Action for Brazilian Application No. BR 11 2018 008708 4 dated Jan. 19, 2021.
Office Action issued in Canadian Application No. 2906606 dated Feb. 1, 2021.
Extended European Search Report for Application No. 20203964.0 dated Feb. 23, 2021.
Dochow, Melanie, et al. "Independent structural domains in paramyxovirus polymerase protein." Journal of Biological Chemistry 287.9 (2012): 6878-6891.
Teng, N. Michael. "The non-structural proteins of RSV: targeting interferon antagonists for vaccine development." Infectious Disorders—Drug Targets (Formerly Current Drug Targets-—Infectious Disorders) 12.2 (2012): 129-137.
Luongo, Cindy, et al. "Increased genetic and phenotypic stability of a promising live-attenuated respiratory syncytial virus vaccine candidate by reverse genetics." Journal of virology 86.19 (2012): 10792-10804.
English Translations of Office Action and Search report issued for Chinese Application No. 201680072681, dated Dec. 7, 2021.
First Examination Report issued in Australian Application No. 2020244533, mailed Apr. 11, 2022.
Communication pursuant to Article 94(3) EPC, issued in European Application No. 16860742.2, mailed Jun. 3, 2022.
English Summary of office action issued in Mexican application No. MX/a/2018/005462, mailed Apr. 12, 2022.
Jin, Hong, et al. "Evaluation of recombinant respiratory syncytial virus gene deletion mutants in African green monkeys for their potential as live attenuated vaccine candidates." Vaccine 21.25-26 (2003): 3647-3652.
English translation of Decision of Rejection issued in Chinese Application No. 201680072681.X, mailed May 10, 2023.
English translation of Decision to Grant issued in Japanese Application No. 2018-522569, mailed Jun. 6, 2023.
English translation of Decision of Rejection issued in Chinese Application No. 202110603289.6, mailed Jun. 9, 2023.
Ternette et al., Immunogenicity and efficacy of codon optimized DNA vaccines encoding the F-protein of respiratory syncytial virus, Vaccine 25 (2007) 7271-7279.

* cited by examiner

| Score | Expect | Method | Identities | Positives | Gaps |
|---|---|---|---|---|---|
| 1169 bits(3023) | 0.0 | Compositional matrix adjust. | 573/574(99%) | 574/574(100%) | 0/574(0%) |

```
Query   1    MELPILKANAITTILAAVTFCFASSQNITEEFYQSTCSAVSKGYLSALRTGWYTSVITIE   60
             MELPILKANAITTILAAVTFCFASSQNITEEFYQSTCSAVSKGYLSALRTGWYTSVITIE
Sbjct   1    MELPILKANAITTILAAVTFCFASSQNITEEFYQSTCSAVSKGYLSALRTGWYTSVITIE   60

Query   61   LSNIKKNKCNGTDAKVKLMKQELDKYKNAVTELQLLMQSTPAANNRARRELPRFMNYTLN   120
             LSNIKKNKCNGTDAKVKLMKQELDKYKNAVTELQLLMQSTPAANNRARRELPRFMNYTLN
Sbjct   61   LSNIKKNKCNGTDAKVKLMKQELDKYKNAVTELQLLMQSTPAANNRARRELPRFMNYTLN   120

Query   121  NTKKTNVTLSKKRKRRFLGFLLGVGSAIASGIAVSKVLHLEGEVNKIKSALLSTNKAVVS   180
             NTKKTNVTLSKKRKRRFLGFLLGVGSAIASGIAVSKVLHLEGEVNKIKSALLSTNKAVVS
Sbjct   121  NTKKTNVTLSKKRKRRFLGFLLGVGSAIASGIAVSKVLHLEGEVNKIKSALLSTNKAVVS   180

Query   181  LSNGVSVLTSRVLDLKNYIDKQLLPIVNKQSCRISNIETVIEFQQKNNRLLEITREFSVN   240
              LSNGVSVLTSRVLDLKNYIDKQLLPIVNKQSCRISNIETVIEFQQKNNRLLEITREFSVN
Sbjct   181  LSNGVSVLTSRVLDLKNYIDKQLLPIVNKQSCRISNIETVIEFQQKNNRLLEITREFSVN   240

Query   241  AGVTTPVSTYMLTNSELLSLINDMPITNDQKKLMSNNVQIVRQQSYSIMSIIKEEVLAYV   300
             AGVTTPVSTYMLTNSELLSLINDMPITNDQKKLMSNNVQIVRQQSYSIMSIIKEEVLAYV
Sbjct   241  AGVTTPVSTYMLTNSELLSLINDMPITNDQKKLMSNNVQIVRQQSYSIMSIIKEEVLAYV   300

Query   301  VQLPLYGVIDTPCWKLHTSPLCTTNTKEGSNICLTRTDRGWYCDNAGSVSFFPQAEKCKV   360
             VQLPLYGVIDTPCWKLHTSPLCTTNTKEGSNICLTRTDRGWYCDNAGSVSFFPQAEKCKV
Sbjct   301  VQLPLYGVIDTPCWKLHTSPLCTTNTKEGSNICLTRTDRGWYCDNAGSVSFFPQAEKCKV   360

Query   361  QSNRVFCDTMYSLTLPSEVNLCNVDIFNPKYDCKIMTSKTDVSSSVITSLGAIVSCYGKT   420
             QSNRVFCDTMYSLTLPSEVNLCNVDIFNPKYDCKIMTSKTDVSSSVITSLGAIVSCYGKT
Sbjct   361  QSNRVFCDTMYSLTLPSEVNLCNVDIFNPKYDCKIMTSKTDVSSSVITSLGAIVSCYGKT   420

Query   421  KCTASNKNRGIIKTFSNGCDYVSNKGVDTVSVGNTLYYVNKQEGKSLYVKGEPIINFYDP   480
             KCTASNKNRGIIKTFSNGCDYVSNKGVDTVSVGNTLYYVNKQEGKSLYVKGEPIINFYDP
Sbjct   421  KCTASNKNRGIIKTFSNGCDYVSNKGVDTVSVGNTLYYVNKQEGKSLYVKGEPIINFYDP   480

Query   481  LVFPSDEFDASISQVNEKINQSLAFIRKSDELLHNVAGKSTTNIMITTIIVIIVILLS    540
             LVFPSDEFDASISQVNEKINQSLAFIRKSDELLHNVAGKSTTNIMITTIIVIIVILLS
Sbjct   481  LVFPSDEFDASISQVNEKINQSLAFIRKSDELLHNVAGKSTTNIMITTIIVIIVILLS    540

Query   541  LIAVGLLLYCKARSTPVTLSKDQLSGINNIAFSN    574
             LIAVGLLLYCKARSTP+TLSKDQLSGINNIAFSN
Sbjct   541  LIAVGLLLYCKARSTPITLSKDQLSGINNIAFSN    574
```

FIG. 9

| Score | Expect | Method | Identities | Positives | Gaps |
|---|---|---|---|---|---|
| 1160 bits(3001) | 0.0 | Compositional matrix adjust. | 570/574(99%) | 572/574(99%) | 0/574(0%) |

```
Query  1    MELPILKANAITTILAAVTFCFASSQNITEEFYQSTCSAVSKGYLSALRTGWYTSVITIE   60
            MELPILKANAITTILAAVTFCFASSQNITEEFYQSTCSAVSKGYLSALRTGWYTSVITIE
Sbjct  1    MELPILKANAITTILAAVTFCFASSQNITEEFYQSTCSAVSKGYLSALRTGWYTSVITIE   60

Query  61   LSNIKKNKCNGTDAKVKLMKQELDKYKNAVTELQLLMQSTPAANNRARRELPRFMNYTLN   120
            LSNIK+NKCNGTDAKVKLMKQELDKYKNAVTELQLLMQSTPAANNRARRELPRFMNYTLN
Sbjct  61   LSNIKENKCNGTDAKVKLMKQELDKYKNAVTELQLLMQSTPAANNRARRELPRFMNYTLN   120

Query  121  NTKKTNVTLSKKRKRRFLGFLLGVGSAIASGIAVSKVLHLEGEVNKIKSALLSTNKAVVS   180
            NTKKTNVTLSKKRKRRFLGFLLGVGSAIASGIAVSKVLHLEGEVNKIKSALLSTNKAVVS
Sbjct  121  NTKKTNVTLSKKRKRRFLGFLLGVGSAIASGIAVSKVLHLEGEVNKIKSALLSTNKAVVS   180

Query  181  LSNGVSVLTSRVLDLKNYIDKQLLPIVNKQSCRISNIETVIEFQQKNNRLLEITREFSVN   240
            LSNGVSVLTS+VLDLKNYIDKQLLPIVNKQSCRISNIETVIEFQQKNNRLLEITREFSVN
Sbjct  181  LSNGVSVLTSKVLDLKNYIDKQLLPIVNKQSCRISNIETVIEFQQKNNRLLEITREFSVN   240

Query  241  AGVTTPVSTYMLTNSELLSLINDMPITNDQKKLMSNNVQIVRQQSYSIMSIIKEEVLAYV   300
            AGVTTPVSTYMLTNSELLSLINDMPITNDQKKLMSNNVQIVRQQSYSIMSIIKEEVLAYV
Sbjct  241  AGVTTPVSTYMLTNSELLSLINDMPITNDQKKLMSNNVQIVRQQSYSIMSIIKEEVLAYV   300

Query  301  VQLPLYGVIDTPCWKLHTSPLCTTNTKEGSNICLTRTDRGWYCDNAGSVSFFPQAEKCKV   360
            VQLPLYGVIDTPCWKLHTSPLCTTNTKEGSNICLTRTDRGWYCDNAGSVSFFPQAE CKV
Sbjct  301  VQLPLYGVIDTPCWKLHTSPLCTTNTKEGSNICLTRTDRGWYCDNAGSVSFFPQAETCKV   360

Query  361  QSNRVFCDTMYSLTLPSEVNLCNVDIFNPKYDCKIMTSKTDVSSSVITSLGAIVSCYGKT   420
            QSNRVFCDTM SLTLPSEVNLCNVDIFNPKYDCKIMTSKTDVSSSVITSLGAIVSCYGKT
Sbjct  361  QSNRVFCDTMNSLTLPSEVNLCNVDIFNPKYDCKIMTSKTDVSSSVITSLGAIVSCYGKT   420

Query  421  KCTASNKNRGIIKTFSNGCDYVSNKGVDTVSVGNTLYYVNKQEGKSLYVKGEPIINFYDP   480
            KCTASNKNRGIIKTFSNGCDYVSNKGVDTVSVGNTLYYVNKQEGKSLYVKGEPIINFYDP
Sbjct  421  KCTASNKNRGIIKTFSNGCDYVSNKGVDTVSVGNTLYYVNKQEGKSLYVKGEPIINFYDP   480

Query  481  LVFPSDEFDASISQVNEKINQSLAFIRKSDELLHNVAGKSTTNIMITTIIVIIVILLS   540
            LVFPSDEFDASISQVNEKINQSLAFIRKSDELLHNVAGKSTTNIMITTIIVIIVILLS
Sbjct  481  LVFPSDEFDASISQVNEKINQSLAFIRKSDELLHNVAGKSTTNIMITTIIVIIVILLS   540

Query  541  LIAVGLLLYCKARSTPVTLSKDQLSGINNIAFSN   574
            LIAVGLLLYCKARSTPVTLSKDQLSGINNIAFSN
Sbjct  541  LIAVGLLLYCKARSTPVTLSKDQLSGINNIAFSN   574
```

FIG. 10

| Score | Expect | Method | Identities | Positives | Gaps |

1160 bits(3002) 0.0   Compositional matrix adjust.   569/574(99%)   0/574(0%)

```
Query   1    MELPILKANAITTILAAVTFCFASSQNITEEFYQSTCSAVSKGYLSALRTGWYTSVITIE    60
             MELPILKANAITTILAAVTFCFASSQNITEEFYQSTCSAVSKGYLSALRTGWYTSVITIE
Sbjct   1    MELPILKANAITTILAAVTFCFASSQNITEEFYQSTCSAVSKGYLSALRTGWYTSVITIE    60

Query   61   LSNIKKNKCNGTDAKVKLMKQELDKYKNAVTELQLLMQSTPAANNRARRELPRFMNYTLN    120
             LSNIK+NKCNGTDAKVKLMKQELDKYKNAVTELQLLMQSTPAANNRARRELPRFMNYTLN
Sbjct   61   LSNIKENKCNGTDAKVKLMKQELDKYKNAVTELQLLMQSTPAANNRARRELPRFMNYTLN    120

Query   121  NTKKTNVTLSKKRKRRFLGFLLGVGSAIASGIAVSKVLHLEGEVNKIKSALLSTNKAVVS    180
             NTKKTNVTLSKKRKRRFLGFLLGVGSAIASGIAVSKVLHLEGEVNKIKSALLSTNKAVVS
Sbjct   121  NTKKTNVTLSKKRKRRFLGFLLGVGSAIASGIAVSKVLHLEGEVNKIKSALLSTNKAVVS    180

Query   181  LSNGVSVLTSRVLDLKNYIDKQLLPIVNKQSCRISNIETVIEFQQKNNRLLEITREFSVN    240
             LSNGVSVLTS+VLDLKNYIDKQLLPIVNKQSCRISNIETVIEFQQKNNRLLEITREFSVN
Sbjct   181  LSNGVSVLTSKVLDLKNYIDKQLLPIVNKQSCRISNIETVIEFQQKNNRLLEITREFSVN    240

Query   241  AGVTTPVSTYMLTNSELLSLINDMPITNDQKKLMSNNVQIVRQQSYSIMSIIKEEVLAYV    300
              GVTTPVSTYMLTNSELLSLINDMPITNDQKKLMSNNVQIVRQQSYSIMSIIKEEVLAYV
Sbjct   241  VGVTTPVSTYMLTNSELLSLINDMPITNDQKKLMSNNVQIVRQQSYSIMSIIKEEVLAYV    300

Query   301  VQLPLYGVIDTPCWKLHTSPLCTTNTKEGSNICLTRTDRGWYCDNAGSVSFFPQAEKCKV    360
             VQLPLYGVIDTPCWKLHTSPLCTTNTKEGSNICLTRTDRGWYCDNAGSVSFFPQAE CKV
Sbjct   301  VQLPLYGVIDTPCWKLHTSPLCTTNTKEGSNICLTRTDRGWYCDNAGSVSFFPQAETCKV    360

Query   361  QSNRVFCDTMYSLTLPSEVNLCNVDIFNPKYDCKIMTSKTDVSSSVITSLGAIVSCYGKT    420
             QSNRVFCDTM SLTLPSEVNLCNVDIFNPKYDCKIMTSKTDVSSSVITSLGAIVSCYGKT
Sbjct   361  QSNRVFCDTMNSLTLPSEVNLCNVDIFNPKYDCKIMTSKTDVSSSVITSLGAIVSCYGKT    420

Query   421  KCTASNKNRGIIKTFSNGCDYVSNKGVDTVSVGNTLYYVNKQEGKSLYVKGEPIINFYDP    480
             KCTASNKNRGIIKTFSNGCDYVSNKGVDTVSVGNTLYYVNKQEGKSLYVKGEPIINFYDP
Sbjct   421  KCTASNKNRGIIKTFSNGCDYVSNKGVDTVSVGNTLYYVNKQEGKSLYVKGEPIINFYDP    480

Query   481  LVFPSDEFDASISQVNEKINQSLAFIRKSDELLHNVAGKSTTNIMITTIIVIIVILLS     540
             LVFPSDEFDASISQVNEKINQSLAFIRKSDELLHNVAGKSTTNIMITTIIVIIVILLS
Sbjct   481  LVFPSDEFDASISQVNEKINQSLAFIRKSDELLHNVAGKSTTNIMITTIIVIIVILLS     540

Query   541  LIAVGLLLYCKARSTPVTLSKDQLSGINNIAFSN  574
             LIAVGLLLYCKARSTPVTLSKDQLSGINNIAFSN
Sbjct   541  LIAVGLLLYCKARSTPVTLSKDQLSGINNIAFSN  574
```

FIG. 11

RECOMBINANT RSV WITH SILENT MUTATIONS, VACCINES, AND METHODS RELATED THERETO

CROSS REFERENCE TO RELATED APPLICATIONS

This Application claims priority to and is a continuation of U.S. application Ser. No. 17/025,568, filed on Sep. 18, 2020, which is a continuation of U.S. application Ser. No. 16/263,915, filed on Jan. 31, 2019, now U.S. Pat. No. 10,792,356, issued on Oct. 6, 2020, which is divisional of U.S. application Ser. No. 14/775,671, filed on Sep. 12, 2015, now U.S. Pat. No. 10,232,032, issued on Mar. 19, 2019, which is a national stage application filed under 35 USC § 371 of PCT Application No. PCT/US2014/027447, filed on Mar. 14, 2014, which claims the benefit of U.S. Provisional Application No. 61/781,228 filed Mar. 14, 2013, and U.S. Provisional Application No. 61/890,500 filed Oct. 14, 2013, both applications which are incorporated by reference in their entirety.

REFERENCE TO SEQUENCE LISTING

A Sequence Listing conforming to the rules of WIPO Standard ST.26 is hereby incorporated by reference. Said Sequence Listing has been filed as an electronic document via PatentCenter in ASCII format encoded as XML. The electronic document, created on Oct. 14, 2022, is entitled "10029-054US2", and is 110,592 bytes in size.

BACKGROUND

Respiratory syncytial virus (RSV) leads to lower respiratory tract infections. Immunocompromised patients, premature infants, and children are particularly at risk to severe disease. RSV is the leading cause of viral death in infants. RSV treatments are focused on prevention from infection and improving respiration. Palivizumab is a humanized monoclonal antibody that can be given prophylactically. Palivizumab is not effective after RSV infection, and protection ends shortly after treatment stops. Vaccines are not currently available for RSV. Attenuated RSV vaccines candidates have failed because of suboptimal immunogenicity in infants and suboptimal stability that leads to genetic reversion towards undesirable wild-type sequences. See Teng, Infectious Disorders—Drug Targets, 2012, 12(2):129-3. Thus, there is a need to find an attenuated RSV vaccine that is appropriately immunogenic, sufficiently stable, and safe for use in infants.

Due to the redundancy of the genetic code, individual amino acids are encoded by multiple sequences of codons, sometimes referred to as synonymous codons. In different species, synonymous codons are used more or less frequently, sometimes referred to as codon bias. Genetic engineering of under-represented synonymous codons into the coding sequence of a gene has been shown to result in decreased rates of protein translation without a change in the amino acid sequence of the protein. Mueller et al. report virus attenuation by changes in codon bias. See, Science, 2008, 320:1784. See also WO/2008121992, WO/2006042156, Burns et al., J Virology, 2006, 80(7):3259 and Mueller et al., J Virology, 2006, 80(19):9687.

Luongo et al. report increased genetic and phenotypic stability of a live-attenuated respiratory syncytial virus vaccine candidate by reverse genetics. See J. Virol. 2012, 86(19):10792.

Dochow et al. report independent structural domains in paramyxovirus polymerase protein. J Biol Chem, 2012, 287:6878-91.

U.S. Pat. No. 8,580,270 reports RSV F polypeptide sequences. U.S. Pat. No. 7,951,384 reports that it contemplates a VLP RSV vaccine.

References cited herein are not an admission of prior art.

SUMMARY

In certain embodiments, the disclosure relates to the polynucleotide sequences of respiratory syncytial virus (RSV). In certain embodiments, the disclosure relates to isolated or recombinant nucleic acids and polypeptides comprising desirable nucleic acid sequences and mutations disclosed herein. In certain embodiments, isolated or recombinant RSV comprising the nucleic acids and polypeptides disclosed herein (e.g., attenuated recombinant RSV) are also provided, as are immunogenic compositions including such nucleic acids, polypeptides, and RSV genomes that are suitable for use as vaccines. Attenuated or killed RSV containing these nucleic acids and mutation in the form of copied nucleic acids (e.g., cDNAs) are also contemplated.

In certain embodiments, this disclosure relates to isolated nucleic acids, recombinant respiratory syncytial virus (RSV) with codon deoptimization, vaccines produced therefrom, and vaccination methods related thereto. In certain embodiments, the recombinant RSV comprises the genes NS1, NS2, N, P, M, SH, G, F, M2, and L of strain A2, line 19, or Long strain or variants thereof. In certain embodiments, the codon deoptimization is in the nonstructural genes NS1 and NS2 and optionally in a gene G and optionally in a gene L. In further embodiments, the gene SH is deleted. In further embodiments, the gene F is mutated, e.g., an I to V mutation corresponding to residue 557 of RSV strain line 19 F protein.

In certain embodiments, the disclosure relates to isolated nucleic acids encoding deoptimized genes NS1 and/or NS2 and optionally the gene G and optionally the gene L of a wild-type human RSV or variant wherein the nucleotides are substituted such that a codon to produce Gly is GGT, a codon to produce Asp is GAT, a codon to produce Glu is GAA, a codon to produce His is CAT, a codon to produce Ile is ATA, a codon to produce Lys is AAA, a codon to produce Leu is CTA, a codon to produce Asn is AAT, a codon to produce Gln is CAA, a codon to produce Val is GTA, or a codon to produce Tyr is TAT, or combinations thereof. In certain embodiments, a gene in the isolated nucleic acid further comprises a combination of at least two, three, four, five, six, seven, eight nine, ten, or all of the individual codons. In certain embodiment, a gene in the isolated nucleic acid comprises at least 20, 30, 40, or 50 or more of the codons.

In certain embodiment, this disclosure relates to isolated nucleic acid as disclosed herein wherein the nucleotides are substituted such that a codon to produce Ala is GCG, a codon to produce Cys is TGT, a codon to produce Phe is TTT, a codon to produce Pro is CCG, a codon to produce Arg is CGT, a codon to produce Ser is TCG, or a codon to produce Thr is ACG, or combinations thereof. In certain embodiments, a gene containing the nucleic acid comprises a combination of at least two, three, four, five, six, seven, eight nine, ten, eleven, twelve, thirteen, fourteen, fifteen, sixteen, or all of the individual codons. In certain embodiments, a gene in the isolated nucleic acid further comprises at least 20, 30, 40, or 50 or more of the codons.

In certain embodiments, the disclosure relates to nucleic acids disclosed herein encoding an NS1 having SEQ ID NO:

5 MGX$^1$NX$^2$LSX$^3$IKX$^4$RLQNLX$^5$X$^6$NDEVALLKI
TCYX$^7$DKLIX$^8$LTNALAKAX$^9$IHTIKL
NGIVFX$^{10}$HVITSSX$^{11}$X$^{12}$CPX$^{13}$NX$^{14}$IVVKSNF
TTMPX$^{15}$LX$^{16}$NGGYIX$^{17}$EX$^{18}$X$^{19}$ELTH
CSQX$^{20}$NGX$^{21}$X$^{22}$X$^{23}$
DNCEIKFSX$^{24}$X$^{25}$LX$^{26}$DSX$^{27}$MTX$^{28}$YX$^{29}$X$^{30}$
QX$^{31}$SX$^{32}$LLGX$^{33}$DL X$^{34}$X$^{35}$, wherein X$^1$-X$^{35}$ are any amino acid or X$^1$ is S or C; X$^2$ is S or T; X$^3$ is M or V; X$^4$ is V or I; X$^5$ is F or L; X$^6$ is D or N; X$^7$ is T or A; X$^8$ is H, L, or Q; X$^9$ is V or T; X$^{10}$ is V or I; X$^{11}$ is D or E; X$^{12}$ is I, A, or V; X$^{13}$ is N or D; X$^{14}$ is N or S; X$^{15}$ is V, I, or A; X$^{16}$ is Q or R; X$^{17}$ is W or any amino acid; X$^{18}$ is M or L; X$^{19}$ is M or I; X$^{20}$ is P or L; X$^{21}$ is L or V; X$^{22}$ is L, M, or I; X$^{23}$ is D or V; X$^{24}$ is K or R; X$^{25}$ is K or R; X$^{26}$ is S or any amino acid; X$^{27}$ is T or V; X$^{28}$ is N or D; X$^{29}$ is M or I; X$^{30}$ is N or S; X$^{31}$ is L or I; X$^{32}$ is E or D; X$^{33}$ is F or L; X$^{34}$ is N or H; and X$^{35}$ is P or S or deleted.

In certain embodiments, the disclosure relates to nucleic acids disclosed herein encoding an NS1 of RSV as provided in NCBI Accession number NP_044589.1, NP_056856.1, P04544.1, AEQ63513.1, AFM55237.1, AFV32554.1, Q86306.1, AFV32528.1, AFM55248.1, AFM95358.1, AFV32568.1, ACY68428.1, CBW45413.1, AC083290.1, AFM55347.1, CBW45433.1, AEQ63459.1, AFM55204.1, AFV32572.1, AFV32558.1, CBW45429.1, CBW45445.1, AFV32596.1, CBW45481.1, CBW47561.1, P24568.1, AAR14259.1, CBW45451.1, CBW45447.1, CBW45471.1, BAE96914.1, CBW45463.1, CBW45473.1, or CBW45467.1 or variants comprising one, two, or three amino acid insertions, deletions, substitutions, or conserved substitutions.

In certain embodiments, the disclosure relates to an isolated nucleic acid comprising SEQ ID NO: 6 or SEQ ID NO: 7 or a sequence with 60%, 70%, 80%, 90%, 95% or greater sequence identity thereto.

In certain embodiments, the disclosure relates to nucleic acids disclosed herein encoding an NS2 having SEQ ID NO: 8, MX$^1$TX$^2$X$^3$X$^4$X$^5$X$^6$TX$^7$QX$^8$LX$^9$ITDMRPX$^{10}$SX$^{11}$X$^{12}$X$^{13}$X$^{14}$IX$^{15}$SLTX$^{16}$X$^{17}$IITHX$^{18}$FIYLI
NX$^{19}$ECIVX$^{20}$KLDEX$^{21}$QATX$^{22}$X$^{23}$FLVNYEMX$^{24}$
LLHX$^{25}$VGSX$^{26}$X$^{27}$YKKX$^{28}$TEYNTK
YGTFPMPIFIX$^{29}$HX$^{30}$GFX$^{31}$ECIGX$^{32}$KPTKHT
PIIX$^{33}$KYDLNP, wherein X$^1$-X$^{33}$ are any amino acid or X$^1$ is D or S; X$^2$ is T, A, or K; X$^3$ is H, S, or N; X$^4$ is N or P; X$^5$ is D, G, or E; X$^6$ is T or N; X$^7$ is P, M, Q, S, or A; X$^8$ is R or G; X$^9$ is M or I; X$^{10}$ is L or M; X$^{11}$ is L, M, or I; X$^{12}$ is I, D, or E; X$^{13}$ is T or S; X$^{14}$ is I or V; X$^{15}$ is I or T; X$^{16}$ is R or K; X$^{17}$ is D or E; X$^{18}$ is R or K; X$^{19}$ is H or N; X$^{20}$ is R or K; X$^{21}$ is R or K; X$^{22}$ is F or L; X$^{23}$ is T or A; X$^{24}$ is K or N; X$^{25}$ is K or R; X$^{26}$ is T or A; X$^{27}$ is K or I; X$^{28}$ is T or S; X$^{29}$ is N or any amino acid; X$^{30}$ is D or G; X$^{31}$ is L or I; X$^{32}$ is I or V; and X$^{33}$ is Y or H.

In certain embodiments, the disclosure relates to nucleic acids disclosed herein encoding an NS1 having an NS2 of RSV as provided in NCBI Accession number NP_044590.1, NP_056857.1, CBW45420.1, AFM95337.1, CBW45416.1, CBW45430.1, AFV32529.1, Q86305.1, AEQ63383.1, CBW45424.1, AFM55546.1, CBW45444.1, P04543.2, AFM55326.1, AFM55425.1, AFM55381.1, AFM55458.1, AFM55216.1, AAB59851.1, AEQ63372.1, AFM55337.1, CBW45426.1, AFV32515.1, AFV32519.1, AAR14260.1, CBW47562.1, AFV32643.1, P24569.1, AFV32657.1, AFI25256.1, CBW45480.1, AFV32605.1, AEQ63580.1, AFV32627.1, AFV32665.1, CBW45482.1, CBW45478.1, CBW45462.1, AEQ63635.1, CBW45448.1, CBW45464.1, CBW45484.1, or CBW45474.1 or variants comprising one, two or three amino acid insertions, deletions, substitutions, or conserved substitutions.

In certain embodiments, the disclosure relates to an isolated nucleic acid comprising SEQ ID NO: 9 or SEQ ID NO: 10 or a sequence with 60%, 70%, 80%, 90%, 95% or greater sequence identity thereto.

In certain embodiments, the disclosure relates to recombinant vectors comprising a nucleic acid disclosed herein.

In certain embodiments, the disclosure relates to an attenuated recombinant RSV comprising a nucleic acid disclosed herein.

In certain embodiments, the disclosure relates to expression system comprising a vector disclosed herein or an attenuated recombinant RSV disclosed herein.

In certain embodiments, the disclosure relates to vaccines comprising an attenuated recombinant RSV disclosed herein.

In certain embodiments, the disclosure relates to methods of vaccination comprising administering an effective amount of a vaccine disclosed herein to a subject at risk of an RSV infection.

In certain embodiments, the subject is younger than 2 months or 6 months of age, under 1 year of age, born prematurely, have congenital heart or lung disease, having chemotherapy or a transplantation, or diagnosed with asthma, congestive heart failure or chronic obstructive pulmonary disease, leukemia, or HIV/AIDS.

In certain embodiments, vaccine is administered in combination with motavizumab, palivizumab, or another humanized monoclonal antibody directed against an epitope in the antigenic site II of the F protein of RSV.

In certain embodiments, the disclosure relates to vectors disclosed herein comprising a bacterial artificial chromosome (BAC), and a nucleic acid sequence comprising respiratory syncytial virus (RSV), and the BAC contains all genes that are essential for the generation of an infectious viral particle in a host cell. The nucleic acid sequence may be a viral genome or antigenome in operable combination with a regulatory element. Typically, the bacterial artificial chromosome comprises one or more genes selected from the group consisting of oriS, repE, parA, and parB genes of factor F in operable combination with a selectable marker, e.g., a gene that provides resistance to an antibiotic.

The nucleic acid sequence may be the genomic or antigenomic sequence of the virus which is optionally mutated as provided herein, e.g., RSV strain which is optionally mutated. In certain embodiments, the expression vector is a plasmid comprising MluI, ClaI, BstBI, SacI restriction endonuclease cleavage sites and optionally an AvrII restriction endonuclease cleavage site outside the region of the wild-type viral sequence or outside the sequences that encode viral genes or outside the viral genome or antigenome. In certain embodiments, the nucleic acid sequence further comprises a selectable marker or reporter gene in operable combination therewith, e.g., a gene that encodes a fluorescent protein.

In certain embodiments, the disclosure relates to isolated bacteria comprising one or more vectors disclosed herein, and other embodiments, the disclosure relates to an isolated cell comprising one or more vectors disclosed herein. In certain embodiments, the vector comprises an RSV antigenome and one or more vectors selected from the group consisting of: a vector encoding an N protein of RSV, a vector encoding a P protein of RSV, a vector encoding an L protein of RSV, and a vector encoding an M2-1 protein of RSV. Typically, the vector comprises a regulatory element, e.g., promoter, and the isolated eukaryotic cell expresses a nucleic acid or polypeptide that activates the regulatory element, e.g., encodes a polypeptide that activates transcription downstream of the promoter. In certain embodiments, the promoter is T7, and the polypeptide that activates transcription downstream of the promoter is T7 RNA polymerase.

In certain embodiments, the disclosure relates to methods of generating respiratory syncytial virus (RSV) particles comprising inserting a vector with a BAC gene and a RSV antigenome into an isolated eukaryotic cell and inserting one or more vectors selected from the group consisting of: a vector encoding an N protein of RSV, a vector encoding a P protein of RSV, a vector encoding an L protein of RSV, and a vector encoding an M2-1 protein of RSV into the cell under conditions such that RSV virion is formed. Inserting a vector into a cell may occur by physically injecting, electroporating, or mixing the cell and the vector under conditions such that the vector enters the cell.

In certain embodiments, the disclosure relates to the stability of the line 19 F557 mutant virus compared to other strains, and val at 557 making RSV expressing line 19 F even more thermostable. Val at position 557 in other strains is also likely stabilizing; thus the 557 position is important for thermal stability. In certain embodiments, the disclosure contemplates other mutations in line 19 F or other RSV strains at position 557 (any amino acid, e.g., alanine, valine, isoleucine, leucine) in any F strain context, that improves thermostability of the RSV virus.

In certain embodiments, the disclosure contemplates RSV F polypeptide comprising an alanine, valine, or leucine at position 557, e.g., alanine or leucine in position 557 of SEQ ID NO: 17.

In certain embodiments, the disclosure relates to certain desirable sequence of RSV F polypeptides e.g., line 19 sequences comprising a valine at position 557, e.g., SEQ ID NO: 17, and recombinant nucleic acids encoding the same. In certain embodiments, the disclosure contemplates recombinant vectors comprising nucleic acids encoding these polypeptides and cells comprising said vectors.

In certain embodiments, the disclosure relates to immunogenic compositions comprising an immunologically effective amount of a recombinant respiratory syncytial virus (RSV), RSV polypeptide, RSV particle, RSV virus-like particle, and/or nucleic acid disclosed herein. In certain embodiments, the disclosure relates to methods for stimulating the immune system of an individual to produce a protective immune response against RSV. In certain embodiments, an immunologically effective amount of a RSV, polypeptide, and/or nucleic acid disclosed herein is administered to the individual in a physiologically acceptable carrier.

In certain embodiments, the disclosure relates to medicaments and vaccine products comprising nucleic acids disclosed herein for uses disclosed herein.

In certain embodiments, the disclosure relates to uses of nucleic acids or vectors disclosed herein for the manufacture of a medicament for uses disclosed herein.

BRIEF DESCRIPTIONS OF THE FIGURES

Figure 4:
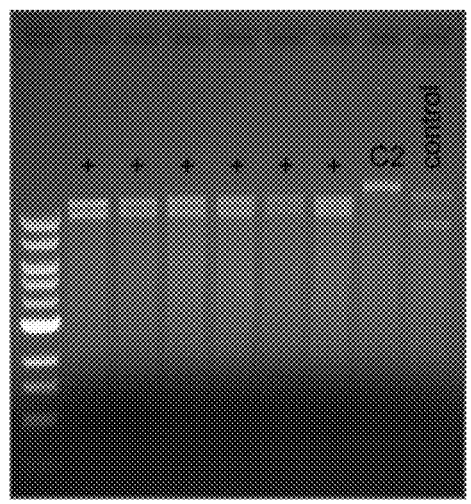

FIG. 4 shows a gel after insertion of galK operon into BAC-RSV by recombineering. MluI digest. Lane 1, ladder marker. Mini-prep BAC DNAs (lanes 2 to 7). Lane 8, parental BAC-RSV "C2" clone. Lane 9, galK-containing plasmid. galK operon has a Mlu I restriction site that serves as a marker for introduction of galK by homologous recombination.

Figure 5:
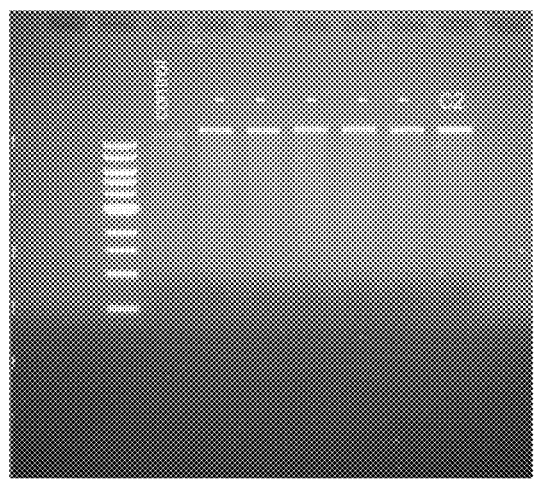
Figure 6A:
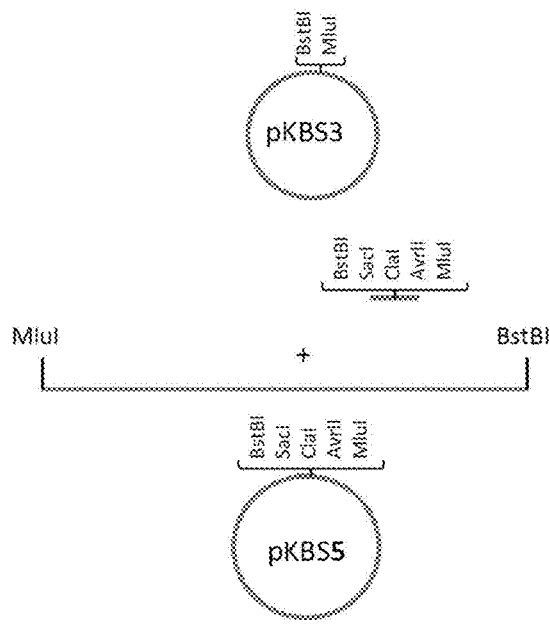
Figure 6B:
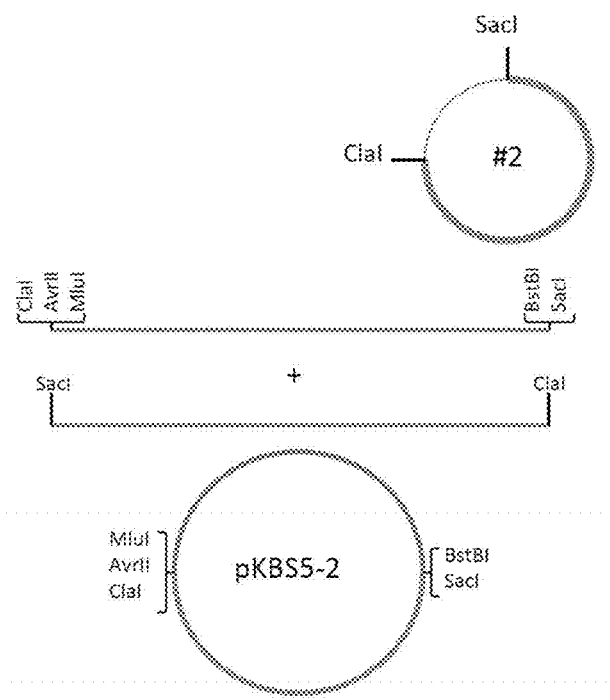
Figure 6C:
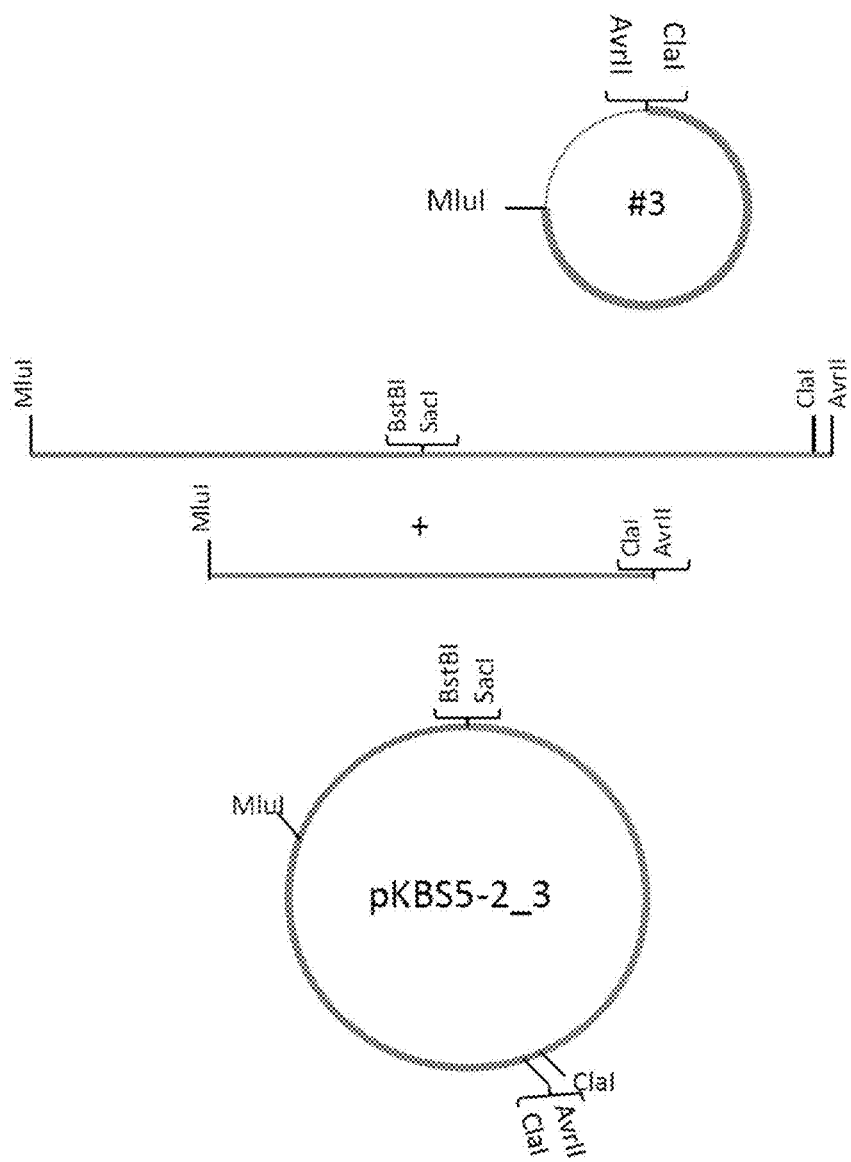
Figure 6D:
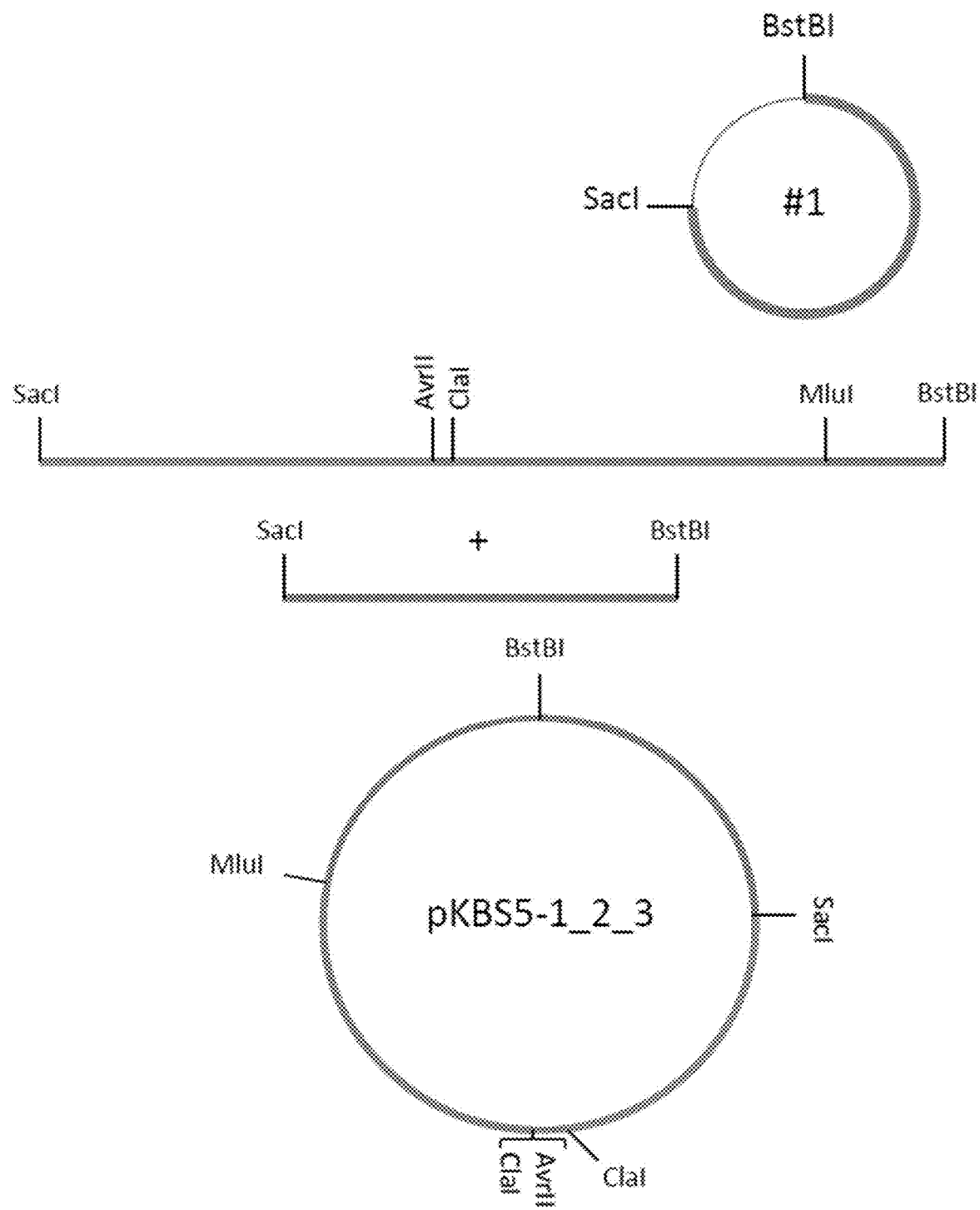
Figure 6E:
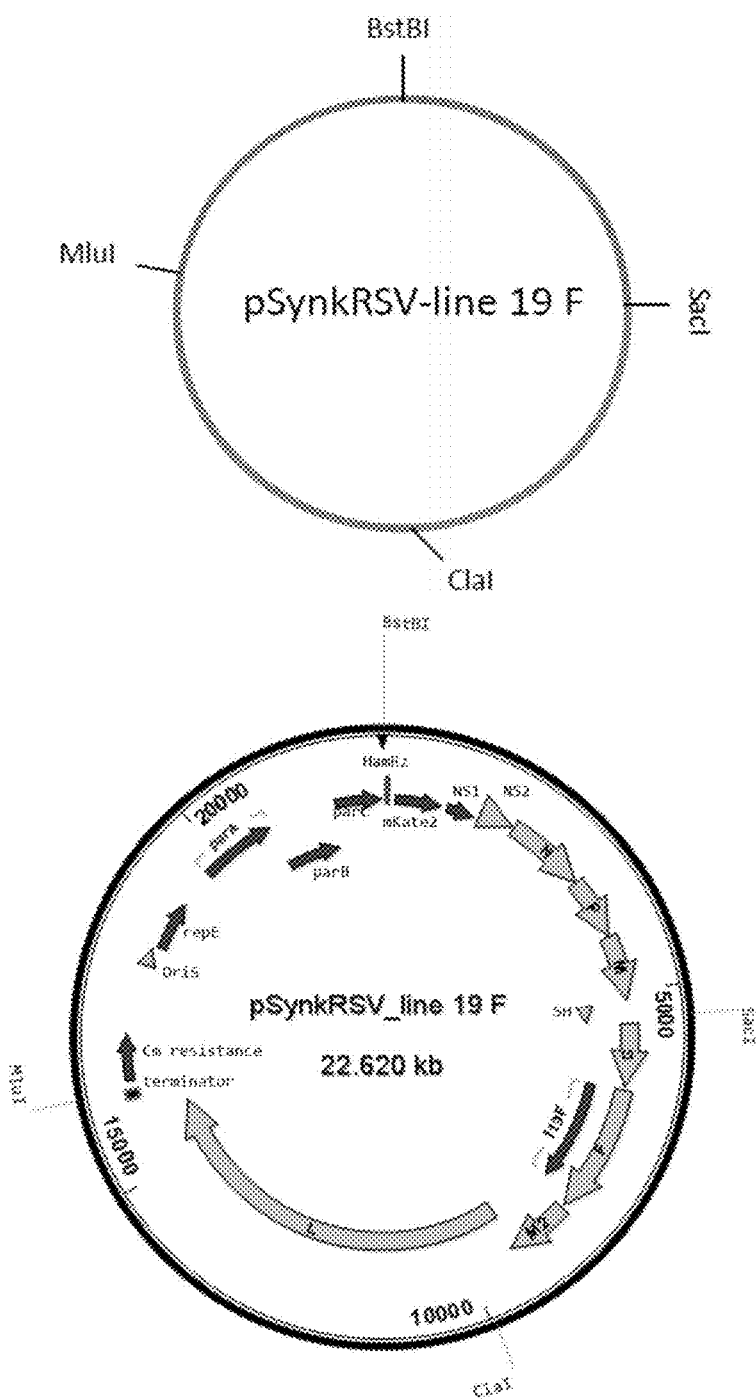

FIG. 5 shows a gel after deletion of galK operon from BAC-RSV by recombineering. MluI digest of galK-containing plasmid (lane 2), BAC mini-prep DNAs (lanes 3-7), and parental BAC-RSV clone C2 (lane 8).

FIGS. 6A-E schematically illustrates steps for creating a BAC-RSV. Three plasmids with RSV segments are generated (see experimental); A) pKBS3 is cut at BstBI and MluI sites to linearize, and is ligated to an oligonucleotide adapter providing pKBS5; B) pSynRSV #2 with SacI and ClaI is cut and ligated to pKBS5 providing pKBS5-2; C) pSynRSV #3 with AvrII and MluI is cut and ligated to pKBS5_2 providing pKBS5_2_3; D) pSynRSV #1 with BstBI and SacI is cut and ligated to pKBS5_2_3 providing pKBS5_1_2_3. E). Recombineering is used to delete nucleotides between two ClaI sites generating pSynRSV-line 19F.

Figure 7A:
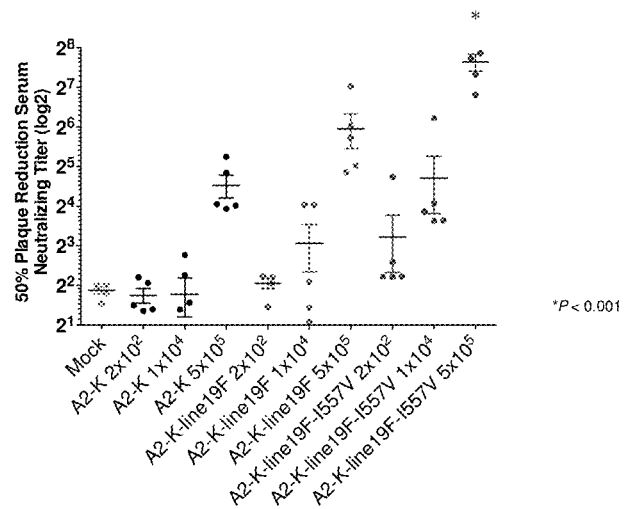
Figure 7B:
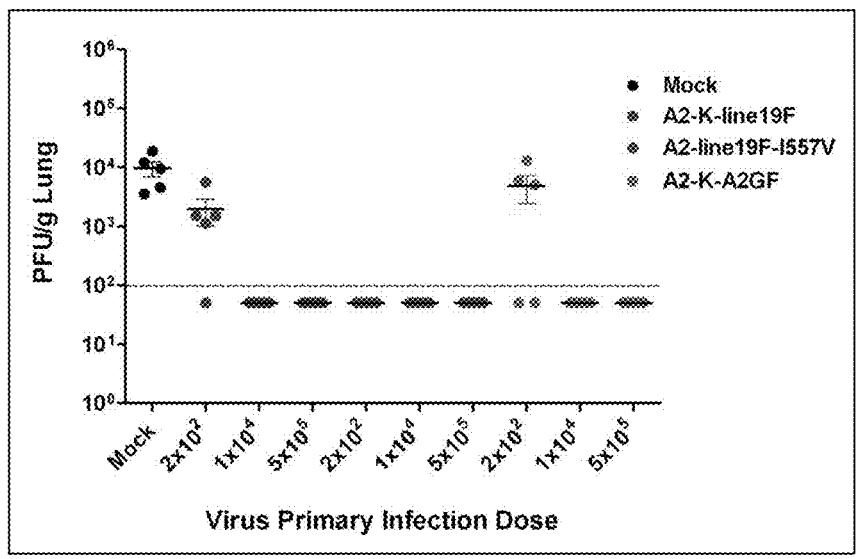

FIGS. 7A and 7B show data showing indicating the immunogenicity of an RSV strain with an F gene I557 to V mutation. Mice were infected with indicated doses of A2-K-line19F, A2-line19F-I557 V, or A2-K-A2GF and 29 days later challenged with RSV strain 12-35. Lung viral load was measured day 4 post-challenge. The dotted line indicates the limit of detection.

Figure 8:
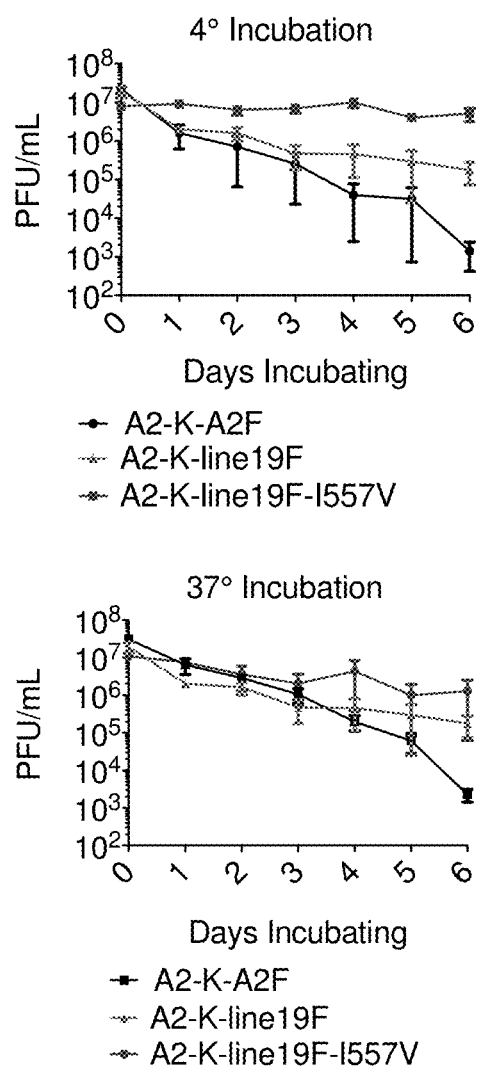

FIG. 8 shows data indicating the superior thermostability of RSV strains with an A2-line 19 F gene I557 to V mutation (SEQ ID NO:17). Viruses were incubated at indicated temperatures and viral titers were measured every day for 6 days. The results at 4° C. are statistically significant between viruses (P<0.01). The results at 37° C. demonstrate the same phenotype.

FIG. 9 illustrates an RSV sequence comparison of strain 19, I557 V mutation (SEQ ID NO:17) (Query) and the typical RSV strain 19 sequence (Sbjct).

FIG. 10 illustrates an RSV sequence comparison of strain 19, I557 V mutation (SEQ ID NO:17) (Query) and sequence 61 from U.S. Pat. No. 7,951,384 (Sbjct).

FIG. 11 illustrates an RSV sequence comparison of strain 19, I557 V mutation (SEQ ID NO:17) (Query) sequence 12 from U.S. Pat. No. 8,580,270 (Sbjct).

Figures 12A, 12B, 12C:
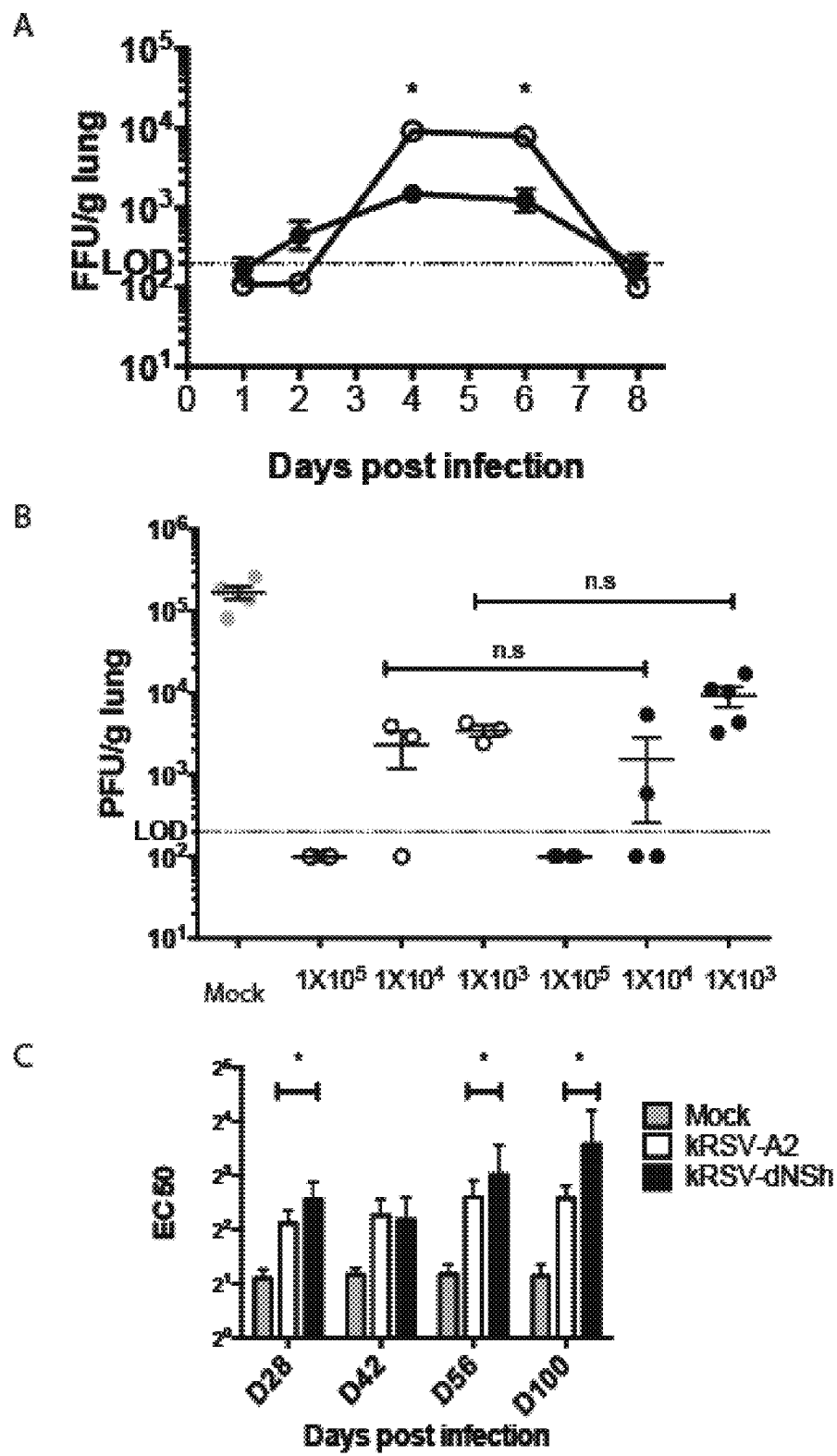

FIGS. 12A-C show data on attenuation, efficacy, and immunogenicity of embodiments disclosed herein. FIG. 12A shows 6-8 week old BALB/c mice (n=5 per group) were infected i.n. with $1.6 \times 10^5$ FFU of kRSV-A2 (open circle) or kRSV-dNSh (closed circle) and lung viral titer was assayed on days 1, 2, 4, 6, and 8 p.i. Data represent one of two replicate experiments with similar results. *P<0.05. FIG. 12B shows BALB/c mice were vaccinated i.n. with varying doses ($10^5$ FFU, $10^4$ FFU, and $10^3$ FFU) of kRSV-A2 (open circle) or kRSV-dNSh (closed circle), or mock-infected, and 100 days after vaccination, mice were challenged with $1.6 \times 10^6$ PFU RSV 12-35 strain. Lung peak viral loads were measured on day 4 after challenge. Each symbol represents one mouse. Dashed lines (A and B) denote the limit of detection for plaque assay. Titers below the limit of detection were assigned half the value of the limit of detection. FIG.

12C shows BALB/c mice (n=5 per group) were mock-infected or infected with 105 FFU of either kRSV-A2 or kRSV-dNSh and serum nAb titers were measured at indicated days after infection. *P<0.05.

Figure 13A:
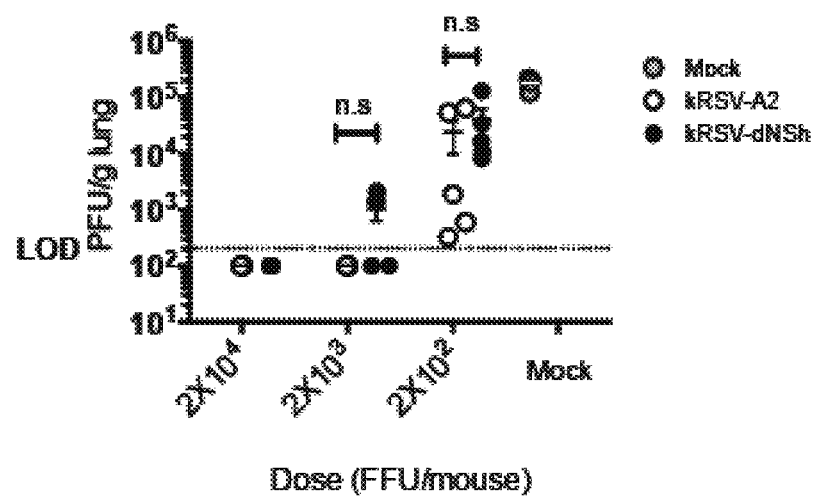
Figure 13B:
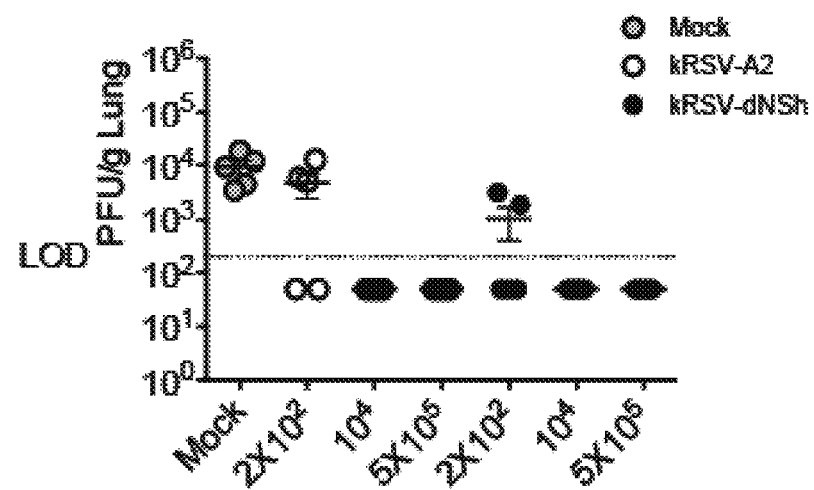

FIGS. 13A and 13B show data on vaccine efficacy for certain embodiments disclosed herein. 6-8 week old BALB/c mice (n=5 per group) were mock-infected or vaccinated with varying indicated doses of kRSV-A2 (open circle) or kRSV-dNSh (closed circle). Mice were challenged 28 days later with (13A) $2\times10^6$ PFU RSV A2-line19 strain or (13B) $5\times10^5$ PFU RSV 12-35. Lung viral loads were measured day 4 after challenge. Each symbol represents one mouse. Dashed lines denote the limit of detection for plaque assay. Titers below the limit of detection were assigned half the value of the limit of detection.

Figures 14A, 14B, 14C:
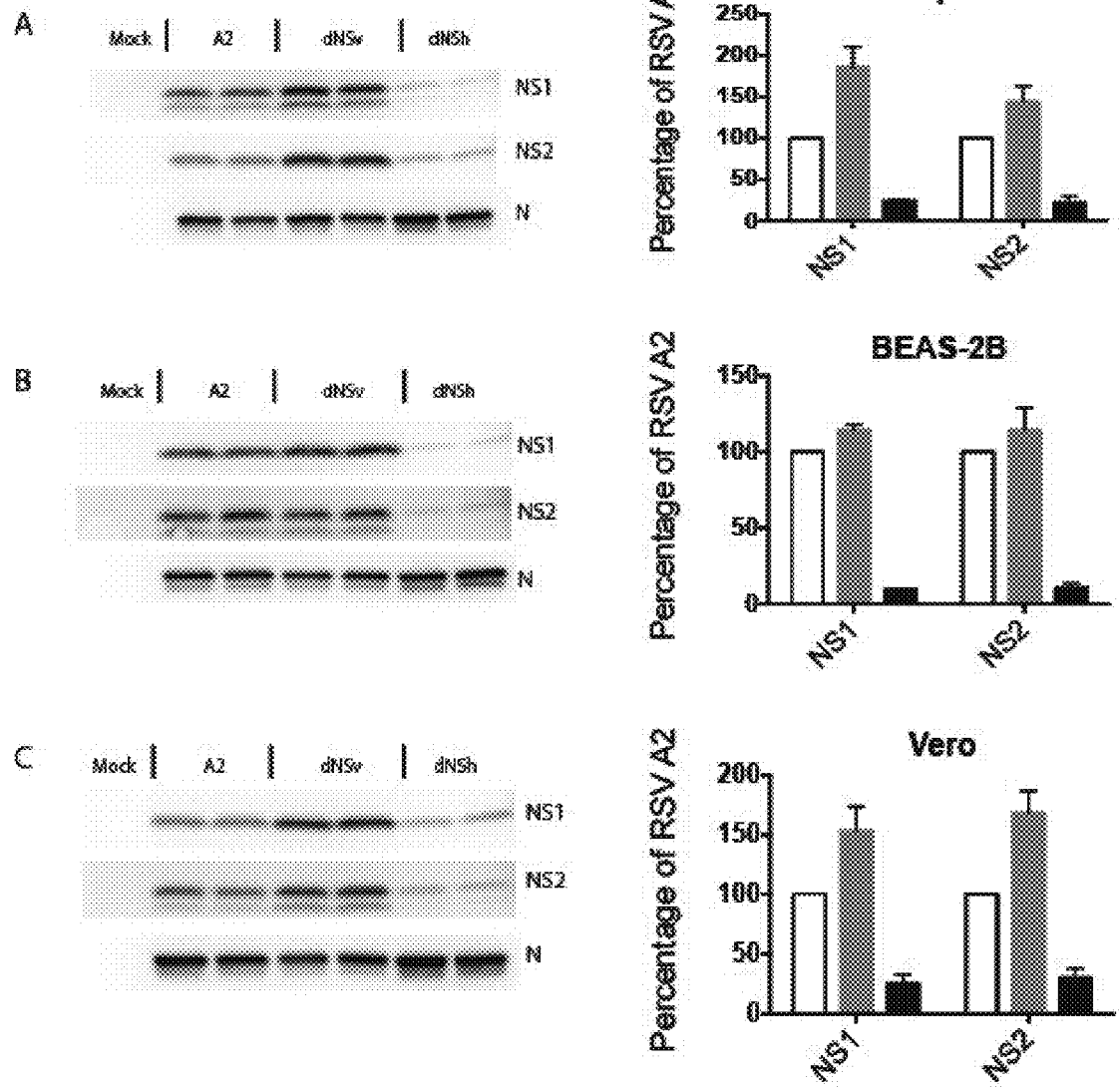

FIGS. 14A-C show data on the expression of NS1 and NS2 proteins during RSV infection in cell lines. HEp-2 (14A), BEAS-2B (14B) and Vero (14C) cells were mock-infected or infected with either kRSV-A2, kRSV-dNSh, or kRSV-dNSv at MOI 5. Twenty hr p.i., NS1 and NS2 protein levels were analyzed by western blot and densitometry. Representative blots are shown on the left. Densitometry from 2-3 independent experiments is shown on the right. After normalizing to RSV N protein levels, NS1 and NS2 protein levels expressed by each virus were normalized to those during kRSV-A2 infection and expressed as percentage±SEM. Unfilled bars represent kRSV-A2, gray bars represent kRSV-dNSv, and black bars represent kRSV-dNSh.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of immunology, medicine, organic chemistry, biochemistry, molecular biology, pharmacology, physiology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

The terms "protein" and "polypeptide" refer to compounds comprising amino acids joined via peptide bonds and are used interchangeably.

The term "portion" when used in reference to a protein (as in "a portion of a given protein") refers to fragments of that protein. The fragments may range in size from four amino acid residues to the entire amino sequence minus one amino acid.

The term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences include those obtained from the same or from different species of organisms.

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferably greater than 75% sequence identity, and still more preferably greater than 90% sequence identity, with a reference sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (mRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

The term "heterologous gene" refers to a gene encoding a factor that is not in its natural environment (i.e., has been altered by the hand of man) For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (e.g., genes expressed in loci where the gene is not normally expressed).

The term "polynucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The polynucleotide may be generated in any manner, including chemical synthesis, DNA replication, reverse transcription, or a combination thereof. The term "oligonucleotide" generally refers to a short length of single-stranded polynucleotide chain usually less than 30 nucleotides long, although it may also be used interchangeably with the term "polynucleotide."

The term "nucleic acid" refers to a polymer of nucleotides, or a polynucleotide, as described above. The term is used to designate a single molecule, or a collection of molecules. Nucleic acids may be single stranded or double stranded, and may include coding regions and regions of various control elements, as described below.

The term "a polynucleotide having a nucleotide sequence encoding a gene" or "a polynucleotide having a nucleotide sequence encoding a gene" or "a nucleic acid sequence encoding" a specified polypeptide refers to a nucleic acid sequence comprising the coding region of a gene or in other words the nucleic acid sequence which encodes a gene product. The coding region may be present in either a cDNA, genomic DNA or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present disclosure may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "complementary" and "complementarity" refer to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (i.e., identity). "Sequence identity" refers to a measure of relatedness between two or more nucleic acids or proteins, and is given as a percentage with reference to the total comparison length. The identity calculation takes into account those nucleotide or amino acid residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence which is completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, Adv. Appl. Math. 2: 482 (1981)) by the homology alignment algorithm of Needleman and Wunsch (Needleman and Wunsch, J. Mol. Biol. 48:443 (1970)), by the search for similarity method of Pearson and Lipman (Pearson and Lipman, Proc. Natl. Acad. Sci. (U.S.) 85:2444 (1988)), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison.

In certain embodiments, term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity.

In certain embodiments, sequence "identity" refers to the number of exactly matching amino acids (expressed as a percentage) in a sequence alignment between two sequences of the alignment calculated using the number of identical positions divided by the greater of the shortest sequence or the number of equivalent positions excluding overhangs wherein internal gaps are counted as an equivalent position. For example the polypeptides GGGGGG and GGGGT have a sequence identity of 4 out of 5 or 80%. For example, the polypeptides GGGPPP and GGGAPPP have a sequence identity of 6 out of 7 or 85%. In certain embodiments, any recitation of sequence identity expressed herein may be substituted for sequence similarity. Percent "similarity" is used to quantify the similarity between two sequences of the alignment. This method is identical to determining the identity except that certain amino acids do not have to be identical to have a match Amino acids are classified as matches if they are among a group with similar properties according to the following amino acid groups: Aromatic—F Y W; hydrophobic—A V I L; Charged positive: R K H; Charged negative—D E; Polar—S T N Q.

The terms "substantial identity" as used herein denotes a characteristic of a polynucleotide sequence, wherein the polynucleotide comprises a sequence that has at least percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present disclosure.

When used in reference to a double-stranded nucleic acid sequence such as a cDNA or genomic clone, the term "substantially homologous" refers to any probe that can hybridize to either or both strands of the double-stranded nucleic acid sequence under conditions of low to high stringency as described above.

When used in reference to a single-stranded nucleic acid sequence, the term "substantially homologous" refers to any probe that can hybridize (i.e., it is the complement of) the single-stranded nucleic acid sequence under conditions of low to high stringency as described above.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and are found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter," or "promoter sequence" as used herein, refer to a DNA sequence that is located at the 5' end (i.e. precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

Promoters may be tissue specific or cell specific. The term "tissue specific" as it applies to a promoter refers to a promoter that is capable of directing selective expression of a nucleotide sequence of interest to a specific type of tissue (e.g., seeds) in the relative absence of expression of the same nucleotide sequence of interest in a different type of tissue (e.g., leaves). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected.

The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining Briefly, tissue sections are embedded in paraffin, and paraffin sections are reacted with a primary antibody which is specific for the polypeptide product encoded by the nucleotide sequence of interest whose expression is controlled by the promoter. A labeled (e.g., peroxidase conjugated) secondary antibody which is specific for the primary antibody is allowed to bind to the sectioned tissue and specific binding detected (e.g., with avidin/biotin) by microscopy.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue.

In contrast, a "regulatable" or "inducible" promoter is one which is capable of directing a level of transcription of an operably linked nucleic acid sequence in the presence of a stimulus (e.g., heat shock, chemicals, light, etc.) which is different from the level of transcription of the operably linked nucleic acid sequence in the absence of the stimulus.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (e.g., the first and second genes can be from the same species, or from different species).

Efficient expression of recombinant DNA sequences in eukaryotic cells typically requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be "heterologous" or "endogenous." An endogenous poly(A) signal is found naturally at the 3' end of the coding region of a given gene in the genome. A heterologous poly(A) signal is one which has been isolated from one gene and positioned 3' to another gene. A commonly used heterologous poly(A) signal is the SV40 poly(A)

signal. The SV40 poly(A) signal is contained on a 237 bp BamHI/BclII restriction fragment and directs both termination and polyadenylation.

The term "vector" refers to nucleic acid molecules that transfer DNA segment(s) from one cell to another. The term "vehicle" is sometimes used interchangeably with "vector."

The terms "expression vector" or "expression cassette" refer to a recombinant nucleic acid containing a desired coding sequence and appropriate nucleic acid sequences used for the expression of the operably linked coding sequence in a particular host organism. Nucleic acid sequences used for expression in prokaryotes typically include a promoter, an operator (optional), and a ribosome binding site, often along with other sequences. Eukaryotic cells are known to utilize promoters, enhancers, and termination and polyadenylation signals.

The term "host cell" refers to any cell capable of replicating and/or transcribing and/or translating a heterologous gene. Thus, a "host cell" refers to any eukaryotic or prokaryotic cell (e.g., bacterial cells such as E. coli, yeast cells, mammalian cells, avian cells, amphibian cells, plant cells, fish cells, and insect cells), whether located in vitro or in vivo. For example, host cells may be located in a transgenic animal.

The term "selectable marker" refers to a gene which encodes an enzyme having an activity that confers antibiotic or drug resistance upon the cell in which the selectable marker is expressed, or which confers expression of a trait which can be detected (e.g., luminescence or fluorescence). Selectable markers may be "positive" or "negative." Examples of positive selectable markers include the neomycin phosphotrasferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term "reporter gene" refers to a gene encoding a protein that may be assayed. Examples of reporter genes include, but are not limited to, modified katushka, mkate and mkate2 (See, e.g., Merzlyak et al., Nat. Methods, 2007, 4, 555-557 and Shcherbo et al., Biochem. J., 2008, 418, 567-574), luciferase (See, e.g., deWet et al., Mol. Cell. Biol. 7:725 (1987) and U.S. Pat. Nos. 6,074,859; 5,976,796; 5,674,713; and 5,618,682; all of which are incorporated herein by reference), green fluorescent protein (e.g., GenBank Accession Number U43284; a number of GFP variants are commercially available from ClonTech Laboratories, Palo Alto, Calif.), chloramphenicol acetyltransferase, beta-galactosidase, alkaline phosphatase, and horse radish peroxidase.

The term "wild-type" when made in reference to a gene refers to a gene which has the characteristics of a gene isolated from a naturally occurring source. The term "wild-type" when made in reference to a gene product refers to a gene product which has the characteristics of a gene product isolated from a naturally occurring source. The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. A wild-type gene is that which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "antisense" or "antigenome" refers to a nucleotide sequence whose sequence of nucleotide residues is in reverse 5' to 3' orientation in relation to the sequence of nucleotide residues in a sense strand. A "sense strand" of a DNA duplex refers to a strand in a DNA duplex which is transcribed by a cell in its natural state into a "sense mRNA." Thus an "antisense" sequence is a sequence having the same sequence as the non-coding strand in a DNA duplex.

The term "isolated" refers to a biological material, such as a virus, a nucleic acid or a protein, which is substantially free from components that normally accompany or interact with it in its naturally occurring environment. The isolated material optionally comprises material not found with the material in its natural environment, e.g., a cell. For example, if the material is in its natural environment, such as a cell, the material has been placed at a location in the cell (e.g., genome or genetic element) not native to a material found in that environment. For example, a naturally occurring nucleic acid (e.g., a coding sequence, a promoter, an enhancer, etc.) becomes isolated if it is introduced by non-naturally occurring means to a locus of the genome (e.g., a vector, such as a plasmid or virus vector, or amplicon) not native to that nucleic acid. Such nucleic acids are also referred to as "heterologous" nucleic acids. An isolated virus, for example, is in an environment (e.g., a cell culture system, or purified from cell culture) other than the native environment of wild-type virus (e.g., the nasopharynx of an infected individual).

An "immunologically effective amount" of RSV is an amount sufficient to enhance an individual's (e.g., a human's) own immune response against a subsequent exposure to RSV. Levels of induced immunity can be monitored, e.g., by measuring amounts of neutralizing secretory and/or serum antibodies, e.g., by plaque neutralization, complement fixation, enzyme-linked immunosorbent, or microneutralization assay.

A "protective immune response" against RSV refers to an immune response exhibited by an individual (e.g., a human) that is protective against serious lower respiratory tract disease (e.g., pneumonia and/or bronchiolitis) when the individual is subsequently exposed to and/or infected with wild-type RSV.

Recombinant Respiratory Syncytial Virus (RSV) with Codon Usage Silent Mutations in the Nonstructural Genes Live-attenuated RSV vaccine candidates have two major hurdles, suboptimal immunogenicity in infants and suboptimal stability that leads to genetic reversion towards wild-type and shedding of revertants by vaccinees. The viral nonstructural (NS) proteins, NS1 and NS2, are unique and inhibit type I interferon and T cell responses. Mutating NS1/NS2 for vaccine enhances immunogenicity. However, previously developed NS1 and NS1/NS2 deletion/null mutant recombinant RSV strains are over-attenuated, and the NS2 null mutant is under-attenuated in vivo.

Figure 2:
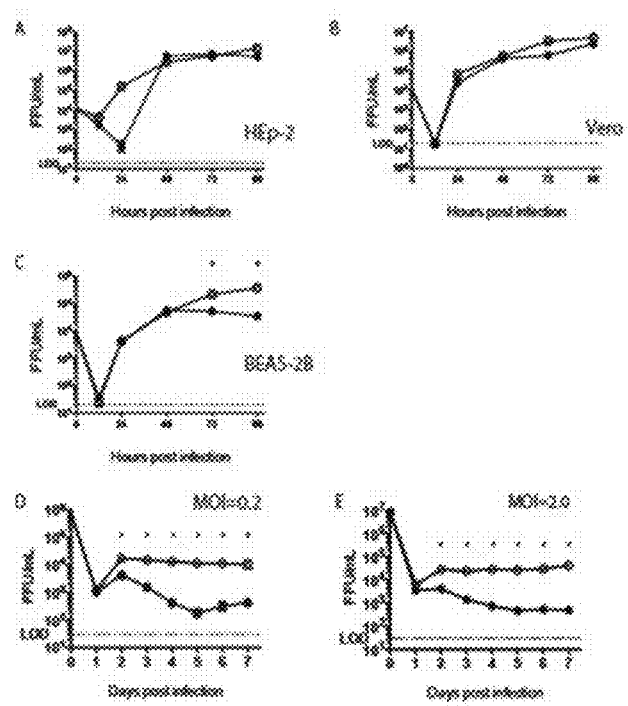
FIG. 2 shows growth data for kRSV-dNS1h in BEAS-2B (top) and Vero cell lines (bottom). Growth curves of kRSV-A2 (open circle) and kRSV-dNSh (closed circle) in HEp-2 (A), Vero (B) and BEAS-2B (C) at 37° C. infected at MOI of 0.01, as well as in differentiated NHBE/ALI cells infected at MOI of 0.2 (D) or 2.0 (E).
Figure 3:
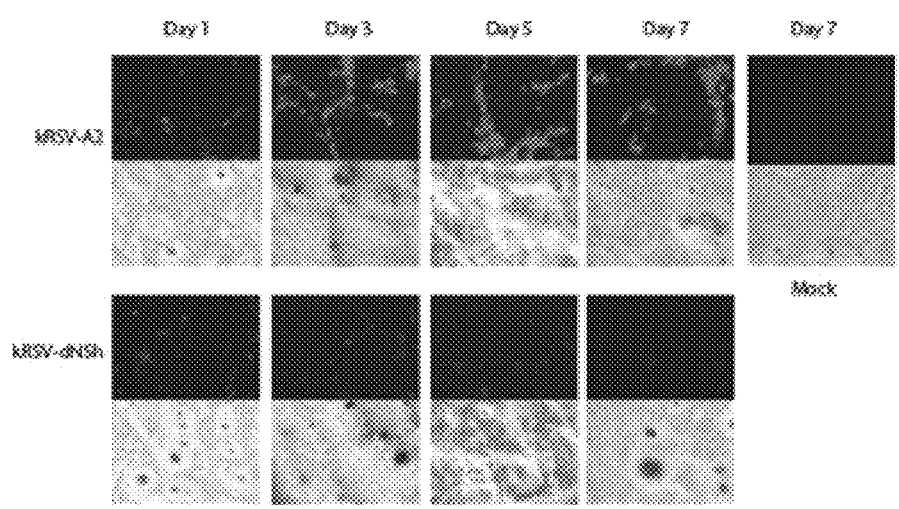
FIG. 3 shows data on viral load experiments using certain embodiments disclosed herein. Time course images for NHBE cells infection at MOI of 0.2, showing mKate2 fluorescence produced by the recombinant viruses. *P<0.05

Mutants disclosed herein overcome the limitations of over-attenuation and instability. Mutants were generated with partial NS1 and NS2 function to bridge the attenuation-immunogenicity gap for a pediatric vaccine. Gene synthesis and the RSV BAC rescue system was used to generate NS1/NS2 mutants by altering codon usage across the NS1 and NS2 genes. Codon de-optimization reduces translation efficiency by multiple mechanisms (e.g., tRNA concentration and mRNA structure). One mutant disclosed herein ("dNSh") has 84/420 nt of NS1 mutated and 82/375 nt of NS2 mutated, reducing human codon preference without altering the amino acid sequences. This virus produces approximately 25% of wt NS1 levels, 25% of wt NS2 levels, 100% of wt nucleoprotein levels, and replicates like wt virus in Vero cells, the cell line commonly used to produce live attenuated RSV under GMP conditions (FIG. 2). In addition to reducing NS expression, this approach likely solves the genetic stability problem because there are too many mutations for reversion.

In certain embodiments, the disclosure relates to a vaccine, recombinant RSV genome, or an isolated recombinant nucleic acid encoding RSV NS1, NS2, N, P, M, G, F, M2-1, M2-2, and L genes comprising codon-deoptimization of the NS1 and NS2 genes, wherein codon-deoptimization is configured such that at least one codon to produce Gly is GGT, a codon to produce Asp is GAT, at least one codon to produce Glu is GAA, at least one codon to produce His is CAT, at least one codon to produce Ile is ATA, at least one codon to produce Lys is AAA, at least one codon to produce Leu is CTA, at least one codon to produce Asn is AAT, at least one codon to produce Gln is CAA, at least one codon to produce Val is GTA, or at least one codon to produce Tyr is TAT, wherein in greater than 25% of the Asp, Glu, His, Ile, Lys, Leu, Asn, Gln, Val, and Tyr amino acids are codon-deoptimized. In certain embodiments, greater than 75% of the amino acids are codon-deoptimized as compared to wild-type sequences, e.g., RSV A2 line 19.

In certain embodiments, the NS1 gene comprises (SEQ ID NO: 6) or variant thereof with greater than 70, 80, 90, 95, 97, 98, or 99% or more sequence identity thereto.

In certain embodiments, the NS2 gene comprises (SEQ ID NO: 9) or variant thereof with greater than 70, 80, 90, 95, 97, 98, or 99% or more sequence identity thereto.

In certain embodiments, the RSV small hydrophobic (SH) glycoprotein gene is deleted.

In certain embodiments, the nucleic acid has further codon-deoptimization of the G gene, wherein codon-deoptimization is configured such that at least one codon to produce Gly is GGT, a codon to produce Asp is GAT, at least one codon to produce Glu is GAA, at least one codon to produce His is CAT, at least one codon to produce Ile is ATA, at least one codon to produce Lys is AAA, at least one codon to produce Leu is CTA, at least one codon to produce Asn is AAT, at least one codon to produce Gln is CAA, at least one codon to produce Val is GTA, or at least one codon to produce Tyr is TAT, wherein in greater than 25% of the Asp, Glu, His, Ile, Lys, Leu, Asn, Gln, Val, and Tyr amino acids are codon-deoptimized.

In certain embodiments, the G gene comprises SEQ ID NO: 18 ATGTCGAAAAACAAAGACCAACGTACCGCGAAGACGTTAGAACGTACCTGGGATACTCTAAATCATTTACTATTCATATCGTCGTGCCTATATAAGCTAAATCTTAAATCGGTAGCACAAATAACACTATCCATACTGGCGATAATAATCTCGACTTCGCTT ATAATAGCAGCGATCATATTTATAGCCTCGGCGAACCATAAAGTCACGCCAACGACTGCGATCATACAAGATGCGACATCGCAGATAAAGAATACAACGCCAACGTA CCTAACCCAAAATCCTCAACTTGGTATCTCGCCCTCGAATCCGTCTGAAATAAC ATCGCAAATCACGACCATACTAGCGTCAACGACACCGGGAGTAAAGTCGACCC TACAATCCACGACAGTAAAGACGAAAAACACGACAACGACTCAAACGCAACCCTCGAAGCCGACCACGAAACAACGCCAAAATAAACCACCGAGCAAACCGAATAA TGATTTTCACTTTGAAGTATTCAATTTTGTACCCTGTAGCATATGTAGCAATAATCCAACGTGCTGGGCGATCTGTAAAAGAATACCGAACAAAAAACCGGGAAAAAA AACCACGACCAAACCCACGAAAAAACCAACGCTCAAAACAACGAAAAAAGATCCCAAACCGCAAACCACGAAATCAAAAGAAGTACCCACGACCAAACCCACGGAAGAGCCGACCATAAACACGACCAAAACGAACATAATAACTACGCTACTCACGT CCAATACCACGGGAAATCCGGAACTCACGAGTCAAATGGAAACGTTTCACTCGACTTCGTCCGAAGGTAATCCATCGCCTTCGCAAGTCTCGACAACGTCCGAATACCCGTCACAACCGTCATCGCCACCGAACACGCCACGTCAGTAG or variant thereof with greater than 70, 80, 90, 95, 97, 98, or 99% or more sequence identity thereto.

In certain embodiments, the G gene comprises SEQ ID NO: 19 ATGTCGAAAAATAAAGACCAACGTACGGCGAAGACGCTAGAACGTACCTGGGA TACGCTAAATCATTTACTATTTATATCGTCGTGCCTATATAAACT AAATCTTAAA TCGGTAGCGCAAATAACACTATCGATACTGGCGATAATAATATCGACTTCGCTA ATAATAGCAGCGATAATATTTATAGCCTCGGCGAATCATAAAGTCACGCCGACG ACTGCGATAATACAAGATGCGACATCGCAAATAAAGAATACGACGCCAACGTA TCTAACCCAAAATCCGCAACTTGGTATATCGCCCTCG AATCCGTCGGAAATAAC ATCGCAAATAACGACCATACTAGCGTCGACGACACCGGGTGTAAAGTCGACGC TACAATCCACGACGGTAAAGACGAAAAATACGACAACGACGCAAACGCAACCG TCGAAACCGACCACGAAACAACGTCAAAATAAACCACCGTCGAAACCGAATAA TGATTTTCACTTTGAAGTATTTAATTTTGTACCCTGTTCGATATGTAGCAATAATCCGACGTGCTGGGCGATATGTAAAAGAATACCGAATAAAAAACCGGGAAAAAA AACGACGACCAAACCGACGAAAAAACCAACGCTAAAAACAACGAAAAAAGATCCGAAACCGCAAACCACGAAATCGAAAGAAGTACCCACGACGAAACCCACGG AAGAACCGACCATAAATACGACCAAAACGAATATAATAACTACGCTACTAACGTCCAATACGACGGGAAATCCGGAACTAACGAGTCAAATGGAAACGTTTCATTC GACTTCGTCGGAAGGTAATCCATCGCCGTCGCAAGTCTCGACGACTTCCGAATA TCCGTCACAACCGTCGTCGCCACCGAATACGCCACGTCAATAG or variant thereof with greater than 70, 80, 90, 95, 97, 98, or 99% or more sequence identity thereto.

In certain embodiments, the G gene comprises SEQ ID NO: 20 ATGTCGAAAAATAAAGATCAACGTACGGCGAAAACGCTAGAACGTACGTGGGATACGCTAAATCATCTACTATTTATATCGTCGTGTCTATATAAACTAAATCTAAAATCGGTAGCGCAAATAACGCTATCGATACTAGCGATAATAATATCGACTTCGCTA ATAATAGCGGCGATAATATTTATAGCGTCGGCGAATCATAAAGTAACGCCGAC GACGGCGATAATACAAGATGCGACTTCGCAAATAAAAAATACGAC GCCGACGT ATCTAACGCAAAATCCGCAACTAGGTA TATCGCCGTCGAATCCGTCGGAAATAA CGTCGCAAATAACGACGATACTAGCGTCGACGACGCCGGGTGTAAAATCGACG CTACAATCGACGACGGTAAAAACGAAAAAT ACGACGACGACGCAAACGCAACC GTCGAAACCGACGACGAAACAACGTCAAAATAAACCGCCGTCGAAACCGAATA ATGATTTTCATTTTGAAGTATTTAATTTTGTACCGTGTTCGATATGTTCGAATAA TCCGACGTGTTGGGCGATATGTAAACGTATACCGAATAAAAAACCGGGTAAAA AAACGACGACGAAACCGACGAAAA AACCGACGCTAAAAACGACGAAAAAAGA TCCGAAACCGCAAACGACGAAATCG AAAGAAGTACCGACGACGAAACCGACG GAAGAACCGACGATAAATACGACGAAAACGAATATAATAACGACGCTACTAAC GTCGAATACGACGGGTAATCCGGAACTAACGTCGCAAATGGAAACGTTTCATTC GACtTCGTCGGAAGGTAATCCGTCGCCGTCGCAAG TATCGACGACtTCGGAATAT CCGTCGCAACCGTCGTCGCCGCCGAATACGCCGCGTCAATAG or variant thereof with greater than 70, 80, 90, 95, 97, 98, or 99% or more sequence identity thereto.

In certain embodiments, F gene encodes a valine at position 557 and lysine at position 66. In certain embodiments, F gene encodes a valine at position 557 and the F gene comprises a sequence that encodes one or more of the follow amino acid sequences F gene comprises two, three, four, five or all of the follow amino acid sequences

```
                              (SEQ ID NO: 11)
TTNIMITTIIIVIIVILLSLIAVGLLLYCK, (SEQ ID NO: 12)
ARSTPVPILKANAITTILAAVTFCFA, (SEQ ID NO: 13)
AVTFCFASSQNITEEFYQST, (SEQ ID NO: 14)
QSTCSAVSKGYLSALRTGWYTSVITIELSNIKK, (SEQ ID NO: 15)
IKK NKCNGTDAKVKLMKQELDKYKNAV,
and (SEQ ID NO: 16)
FPQAEKCKVQSNRVFC DTMYSLTLPSEVNLCNV.
```

In certain embodiments, the F gene comprises two, three, four, five or all of the follow amino acid sequences (SEQ ID NO: 11), (SEQ ID NO: 12), (SEQ ID NO: 13), (SEQ ID NO: 14), (SEQ ID NO: 15), and (SEQ ID NO: 16).

In certain embodiments, the F gene encodes a valine at position 557 and the F gene encodes one or more of the follow amino acids: asparagine at position 8, phenylalanine at position 20, serine at position 35, lysine at position 66, methionine at position 79, lysine at position 124, arginine at position 191, arginine at position 213, glutamic acid at position 354, lysine at position 357, tyrosine at position 371, valine at position 384, asparagine at position at 115, and threonine at position 523.

In certain embodiments, the F gene encodes a valine at position 557 and lysine at position 66 and methionine at position 79.

In certain embodiments, the F gene encodes a valine at position 557 and lysine at position 66 and arginine at position 191.

In certain embodiments, the F gene encodes a valine at position 557, lysine at position 66, arginine at position 191, and lysine at position 357.

In certain embodiments, the F gene encodes a valine at position 557, lysine at position 66, methionine at position 79, and asparagine at position at 115.

In certain embodiments, the F gene encodes SEQ ID NO: 17

```
MELPILKANAITTILAAVTFCFASSQNITEEFYQSTCSAVSKGYLSALRT

GWYTSVITIELSNIKKNKCNGTDAKVKLMKQELDKYKNAVTELQLLMQST

PAANNRARRELPRFMNYTLNNTKKTNVTLSKKRKRRFLGFLLGVGSAIAS

GIAVSKVLHLEGEVNKIKSALLSTNKAVVSLSNGVSVLTSRVLDLKNYID

KQLLPIVNKQSCRISNIETVIEFQQKNNRLLEITREFSVNAGVTTPVSTY

MLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVS

FFPQAEKCKVQSNRVFCDTMYSLTLPSEVNLCNVDIFNPKYDCKIMTSKT

DVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKIN

QSLAFIRKSDELLHNVNAGKSTTNIMITTIIIVIIVILLSLIAVGLLLYC

KARSTPVTLSKDQLSGINNIAFSN
``` or variants that contain one, two, three, four, five, six, seven, eight, nine, or ten amino acid substitutions provided F gene encodes a valine at position 557. In certain embodiments, the amino acid substitutions are conservative substitutions.

In certain embodiments, the disclosure relates to an isolated recombinant nucleic acid comprising an F gene encoding (SEQ ID NO: 17) or variants that contains one or two amino acid substitutions provided F gene encodes a valine at position 557 and lysine at position 66.

In certain embodiments, the F gene encodes a valine at position 557 and the F gene encodes one or more of the follow amino acids: asparagine at position 8, phenylalanine at position 20, serine at position 35, lysine at position 66, methionine at position 79, lysine at position 124, arginine at position 191, arginine at position 213, glutamic acid at position 354, lysine at position 357, tyrosine at position 371, valine at position 384, asparagine at position at 115, and threonine at position 523.

In certain embodiments, the F gene encodes a valine at position 557 and lysine at position 66.

In certain embodiments, the F gene encodes a valine at position 557 and lysine at position 66 and methionine at position 79.

In certain embodiments, the F gene encodes a valine at position 557, lysine at position 66, arginine at position 191, and lysine at position 357.

In certain embodiments, the F gene encodes a valine at position 557, lysine at position 66, methionine at position 79, and asparagine at position 115.

In certain embodiments, the disclosure relates to a recombinant vector comprising a nucleic acid disclosed herein. In certain embodiments, the disclosure relates to a cell comprising the recombinant vector, recombinant RSV, or attenuated recombinant RSV disclosed herein.

In certain embodiments, the disclosure relates to an F gene encoding (SEQ ID NO: 17) or variants that contains one amino acid substitutions provided F gene encodes a valine at position 557.

In certain embodiments, the disclosure relates to an F gene encoding MELPILKANAITTILAAVTFCFASSQNI-TEEFYQSTCSAVS KGYLSALRTGWYTSVITI ELSNI-KENKCNGTDAKVKLMKQELDKYKNAVTELQLL-MQSTPAANNRARRELPRF MNYTLNNTKKTNVTLSKKRKRRFLGFLLGVGSA-IASGIAVSKVLHLEGEVNKIKSA LLSTNKAVVSL-SNGVSVLTSRVLDLKNYIDKQLLPIVNKQSCRISNIET-VIEFQQKNN RLLEITREFSVNAGVTTPVSTYMLTN-SELLSLINDMPITNDQKKLMSNNVQIVRQQS YSIM-SIIKEEVLAYVVQLPLYGVIDTPCWKLHT-SPLCTTNTKEGSNICLTRTDRGWY CDNAGSVSFFPQAEKCKVQSNRVFCDTMYSLTLP-SEVNLCNVDIFNPKYDCKIMTS KTDVSSSVITSL-GAIVSCYGKTKC-TASNKNRGIIKTFSNGCDYVSNKGVDTVSVGNT LYYVNKQEGKSLYVKGEPIINFYDPLVFPSDEFDA-SISQVNEKINQSLAFIRKSDELL HNVNAGKSTTNIMI-TTIIVIIVILLSLIAVGLLLYCKARSTPVTL-SKDQLSGINNIAFSN (SEQ ID NO: 21). In certain embodiments, the F gene encodes a valine at position 557 and glutamic acid at position 66 and arginine at position 191.

In certain embodiments, the disclosure relates to recombinant polypeptides comprising an RSV F protein sequence disclosed herein. In certain embodiments, the disclosure relates to virus particles or virus like particles produced by recombinant methods comprising a RSV F protein sequence disclosed herein.

In certain embodiments, the disclosure relates to an isolated recombinant nucleic acid comprising an RSV genome OE1 of SEQ ID NO: 1 or variant with greater than 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% or more sequence identity thereto.

In certain embodiments, the disclosure relates to an isolated recombinant nucleic acid comprising an RSV genome OE2 of SEQ ID NO: 2 or variant with greater than 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% or more sequence identity thereto.

In certain embodiments, the disclosure relates to an isolated recombinant nucleic acid comprising an RSV genome OE3 of SEQ ID NO: 3 or variant with greater than 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% or more sequence identity thereto.

In certain embodiments, the disclosure relates to an isolated recombinant nucleic acid comprising an RSV genome OE4 of SEQ ID NO: 4 or variant with greater than 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% or more sequence identity thereto.

In certain embodiments, the disclosure contemplates isolated recombinant nucleic acids comprising RSV genomes OE1, OE2, OE3, and OE4, wherein one or both of the NS1 gene and NS2 gene are deleted.

Cultivating RSV in a Bacterial Artificial Chromosome

Cultivating RSV in *E. coli* bacteria may be accomplished by utilizing a bacterial artificial chromosome (BAC). A BAC is disclosed that contains the complete antigenomic sequence of respiratory syncytial virus (RSV) strain A2 except the F gene, which is the antigenomic sequence of RSV strain line 19. Along with helper plasmids, it can be used in the reverse genetics system for the recovery of infectious virus. The antigenome sequence on the plasmid can be mutated prior to virus recovery to generate viruses with desired mutations.

The plasmid is an improvement on current RSV antigenomic plasmids for several reasons. Each RSV gene is flanked by restriction endonuclease cleavage sites to allow for easy manipulation of any gene. As a basis for viral mutagenesis, this plasmid may be used to design attenuated viruses for use in vaccines. An extra gene encoding the monomeric katushka 2, mKate2, protein has been included in the antigenome prior to the first RSV gene. The mKate2 protein is a far-red fluorescent protein which would be expressed in concert with the other RSV genes and would serve as visual evidence of virus replication. Changes have also been made to the ribozyme sequences that flank the RSV antigenome and play a role in the production of infectious virus through reverse genetics.

The disclosed vectors allow for efficient mutagenesis through recombineering. This mutagenesis method requires little to no ligation cloning, but relies on the recombination machinery present in bacteria harboring certain genes from a bacteriophage. Because RSV cDNAs are often unstable in mid-to-high copy number cloning vectors within bacteria predominantly used for cloning, such as *Escherichia coli* (*E. coli*), the single digit copy nature of the bacterial artificial chromosome reduces the instability, and the reduced instability is thought to occur because the single copy nature limits the ability *E coli* to recognize crypic promoters in the RSV cDNA and produce toxic proteins.

Respiratory Syncytial Virus (RSV)

Typically, the RSV particle contains a viral genome within a helical nucleocapsid which is surrounded by matrix proteins and an envelope containing viral glycoproteins. The genome of wild-type RSV encodes the proteins, NS1, NS2, N, P, M, SH, G, F, M2-1, M2-2, and L. G, F, and SH are glycoproteins. The F gene has been incorporated into a number of viral vaccines. RSV polymerase activity consists of the large protein (L) and phosphoprotein (P). The viral M2-1 protein is used during transcription and is likely to be a component of the transcriptase complex. The viral N protein is used to encapsidate the nascent RNA.

The genome is transcribed and replicated in the cytoplasm of a host cell. Host-cell transcription typically results in synthesis of ten methylated and polyadenylated mRNAs. The antigenome is positive-sense RNA complement of the genome produced during replication, which in turn acts as a template for genome synthesis. The viral genes are flanked by conserved gene-start (GS) and gene-end (GE) sequences. At the 3' and 5' ends of the genome are leader and trailer nucleotides. The wild type leader sequence contains a promoter at the 3' end. When the viral polymerase reaches a GE signal, the polymerase polyadenylates and releases the mRNA and reinitiates RNA synthesis at the next GS signal. The L-P complex is believed to be responsible for recognition of the promoter, RNA synthesis, capping and methylation of the 5' termini of the mRNAs and polyadenylation of their 3' ends. It is believed that the polymerase sometimes dissociates from the gene at the junctions. Because the polymerase initiates transcription at the 3' end of the genome, this results in a gradient of expression, with the genes at the 3' end of the genome being transcribed more frequently than those at the 5' end.

To replicate the genome, the polymerase does not respond to the cis-acting GE and GS signals and generates positive-sense RNA complement of the genome, the antigenome. At the 3' end of the antigenome is the complement of the trailer, which contains a promoter. The polymerase uses this promoter to generate genome-sense RNA. Unlike mRNA, which is released as naked RNA, the antigenome and genome RNAs are encapsidated with virus nucleoprotein (N) as they are synthesized.

In certain embodiments, the disclosure relates to vectors and nucleic acids that contain RSV gene(s) such as the wild-type genome or antigenome. An example of an RSV antigenome is provided in U.S. Pat. No. 6,790,449, hereby incorporated by reference. Reference to RSV gene(s) and the genome is contemplated to include certain mutations, deletions, or variant combinations, such as cold-passaged (cp) and temperature sensitive (ts) derivatives of RSV, cpRSV, such as rA2cp248/404/1030ASH. rA2cp248/404ASH contains independent attenuating genetic elements: cp which is based on 5 missense mutations in the N and L proteins and the F glycoprotein that together confer the non-ts attenuation phenotype of cpRSV; ts248, a missense mutation in the L protein; ts404, a nucleotide substitution in the gene-start transcription signal of the M2 gene; and ASH, complete deletion of the SH gene. rA2cp248/404/1030ASH contains 5 independent attenuating genetic elements: those present in rA2cp248/404ASH and ts1030, another missense mutation in the L protein. See Karron et al., J Infect Dis., 2005, 191(7): 1093-1104, hereby incorporated by reference. Within certain embodiments, it is contemplated that the RSV anitgenome may contain deletion or mutations in nonessential genes (e.g., the SH, NS1, NS2, and M2-2 genes) or combinations thereof.

Bacterial Artificial Chromosomes (BACs)

In certain embodiments, the disclosure relates to vectors and nucleic acids that contain bacterial artificial chromosomes. A bacterial cloning system for mapping and analysis of complex genomes has been disclosed in Shizuya et al., Proc. Natl. Acad. Sci., 1992, 89:8794-8797. The BAC system (for bacterial artificial chromosome) is based on *Escherichia coli* and its single-copy plasmid F factor which were described as useful for cloning large fragments of human DNA. The F factor encodes for genes that regulate its own replication including oriS, repE, parA, and parB. The oriS and repE genes mediate the unidirectional replication of the F factor while parA and parB typically maintain copy number at a level of one or two per *E. coli* genome. It is contemplated that the genes and the chromosome may contain mutations, deletions, or variants with desired functional attributes. The BAC vector (pBAC) typically contains these genes as well as a resistance marker and a cloning segment containing promoters for incorporating nucleic acid segments of interest by ligating into restriction enzyme sites. Exemplary BAC systems include those described in Shizuya & Kouros-Hehr, Keio J Med, 2001, 50(1): 26-30, hereby incorporated by reference.

One may reconstitute infectious RSV virus from the RSV BAC plasmids disclosed herein. BAC vectors can be transfected to bacteria such as *E. coli* by electroporation. The RSV-BACs disclosed herein may be stably maintained in bacteria, re-isolated from the bacteria, and inserted into a eukaryotic cell along with one or more vectors that express the N, P, L, and M2-1 proteins. These cells produce infective RSV particles. Production of infectious RSV results from co-transfection of plasmids encoding N, P, L, and M2-1 proteins and the antigenome under control of the T7 promoter into BHK-21 cells that express T7 RNA polymerase (BSR cells). See Buchholz et al., J Virol., 2000, 74(3):1187-1199, hereby incorporated by reference.

Vaccines

A number of attenuated RSV strains as candidate vaccines for intranasal administration have been developed using multiple rounds of chemical mutagenesis to introduce multiple mutations into a virus. Evaluation in rodents, chimpanzees, adults and infants indicate that certain of these candidate vaccine strains are immunogenic, and may be attenuated. Nucleotide sequence analysis of some of these attenuated viruses indicates that each level of increased attenuation is typically associated with two or more new nucleotide and amino acid substitutions.

The disclosure provides the ability to distinguish between silent incidental mutations versus those responsible for phenotype differences by introducing the mutations, separately and in various combinations, into the genome or antigenome of infectious RSV. This process identifies mutations responsible for phenotypes such as attenuation, temperature sensitivity, cold-adaptation, small plaque size, host range restriction, etc. Mutations from this menu can then be introduced in various combinations to calibrate a vaccine virus to an appropriate level of attenuation, etc., as desired. Moreover, the present disclosure provides the ability to combine mutations from different strains of virus into one strain.

The present disclosure also provides for methods of attenuation. For example, individual internal genes of RSV can be replaced with their bovine, murine or other RSV counterpart. This may include part or all of one or more of the NS1, NS2, N, P, M, SH, M2-1, M2-2 and L genes, or parts of the G and F genes. Reciprocally, means are provided to generate a live attenuated bovine RSV by inserting human attenuating genes into a bovine RSV genome or antigenome background. Human RSV bearing bovine RSV glycoproteins provides a host range restriction favorable for human vaccine preparations. Bovine RSV sequences which can be used in the present disclosure are described in, e.g., Pastey et al., J. Gen. Viol. 76:193-197 (1993); Pastey et al., Virus Res. 29:195-202 (1993); Zamora et al., J. Gen. Virol. 73:737-741 (1992); Mallipeddi et al., J. Gen. Virol. 74:2001-2004 (1993); Mallipeddi et al., J. Gen. Virol. 73:2441-2444 (1992); and Zamora et al., Virus Res. 24:115-(1992), each of which is incorporated herein by reference.

The disclosure also provides the ability to analyze other types of attenuating mutations and to incorporate them into infectious RSV for vaccine or other uses. For example, a tissue culture-adapted nonpathogenic strain of pneumonia virus of mice (the murine counterpart of RSV) lacks a cytoplasmic tail of the G protein (Randhawa et al., Virology 207: 240-245 (1995)). By analogy, the cytoplasmic and transmembrane domains of each of the RSV glycoproteins, F, G and SH, can be deleted or modified to achieve attenuation.

Other mutations for use in infectious RSV of the present disclosure include mutations in cis-acting signals identified during mutational analysis of RSV minigenomes. For example, insertional and deletional analysis of the leader and trailer and flanking sequences identified viral promoters and transcription signals and provided a series of mutations associated with varying degrees of reduction of RNA replication or transcription. Saturation mutagenesis (whereby each position in turn is modified to each of the nucleotide alternatives) of these cis-acting signals also has identified many mutations which reduced (or in one case increased) RNA replication or transcription. Any of these mutations can be inserted into the complete antigenome or genome as described herein. Other mutations involve replacement of the 3' end of genome with its counterpart from antigenome, which is associated with changes in RNA replication and transcription. In addition, the intergenic regions (Collins et al., Proc. Natl. Acad. Sci. USA 83:4594-4598 (1986), incorporated herein by reference) can be shortened or lengthened or changed in sequence content, and the naturally-occurring gene overlap (Collins et al., Proc. Natl. Acad. Sci. USA 84:5134-5138 (1987), incorporated herein by reference) can be removed or changed to a different intergenic region by the methods described herein.

In another embodiment, RSV useful in a vaccine formulation can be conveniently modified to accommodate antigenic variation in circulating virus, including antigenic subgroup A and B strains and variations within those subgroups. Typically the modification will be in the G and/or F proteins. The entire G or F gene, or the segment(s) encoding particular immunogenic regions thereof, is incorporated into the RSV genome or antigenome cDNA by replacement of the corresponding region in the infectious clone or by adding one or more copies of the gene such that several antigenic forms are represented. Progeny virus produced from the modified RSV cDNA are then used in vaccination protocols against the emerging strains. Further, inclusion of the G protein gene of RSV subgroup B would broaden the response to cover a wider spectrum of the relatively diverse subgroup A and B strains infecting human populations.

An infectious RSV clone of the disclosure can also be engineered to enhance its immunogenicity and induce a level of protection greater than that provided by natural infection, or vice versa, to identify and ablate epitopes associated with undesirable immunopathologic reactions. Enhanced immunogenicity of the vaccines produced by the present disclosure addresses one of the greatest obstacles to controlling RSV, namely the incomplete nature of immunity induced by natural infection. An additional gene may be inserted into or proximate to the RSV genome or antigenome which is under the control of an independent set of transcription signals. Genes of interest include those encoding cytokines (e.g., IL-2 through IL-15, especially IL-3, IL-6 and IL-7, etc.), gamma-interferon, and proteins rich in T helper cell epitopes. The additional protein can be expressed either as a separate protein or as a chimera engineered from a second copy of one of the RSV proteins, such as SH. This provides the ability to modify and improve the immune response against RSV both quantitatively and qualitatively.

For vaccine use, virus produced according to the present disclosure can be used directly in vaccine formulations, or lyophilized, as desired, using lyophilization protocols well known to the artisan. Lyophilized virus will typically be maintained at about 4 degrees C. When ready for use the lyophilized virus is reconstituted in a stabilizing solution, e.g., saline or comprising SPG, Mg, and HEPES, with or without adjuvant, as further described below.

Thus RSV vaccines of the disclosure contain as an active ingredient an immunogenetically effective amount of RSV produced as described herein. The modified virus may be introduced into a host with a physiologically acceptable carrier and/or adjuvant. Useful carriers are well known in the art, and include, e.g., water, buffered water, 0.4% saline, 0.3% glycine, hyaluronic acid and the like. The resulting aqueous solutions may be packaged for use as is, or lyophilized, the lyophilized preparation being combined with a sterile solution prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like. Acceptable adjuvants include incomplete Freund's adjuvant, aluminum phosphate, aluminum hydroxide, or alum, which are materials well known in the art.

Upon immunization with a RSV composition as described herein, via aerosol, droplet, oral, topical or other route, the immune system of the host responds to the vaccine by producing antibodies specific for RSV virus proteins, e.g., F and G glycoproteins. As a result of the vaccination the host becomes at least partially or completely immune to RSV infection, or resistant to developing moderate or severe RSV infection, particularly of the lower respiratory tract.

The host to which the vaccines are administered can be any mammal which is susceptible to infection by RSV or a closely related virus and which host is capable of generating a protective immune response to the antigens of the vaccinating strain. Thus, suitable hosts include humans, non-human primates, bovine, equine, swine, ovine, caprine, lagamorph, rodents, etc. Accordingly, the disclosure provides methods for creating vaccines for a variety of human and veterinary uses.

The vaccine compositions containing the RSV of the disclosure are administered to a host susceptible to or otherwise at risk of RSV infection to enhance the host's own immune response capabilities. Such an amount is defined to be an "immunogenically effective dose." In this use, the precise amounts again depend on the host's state of health and weight, the mode of administration, the nature of the formulation. The vaccine formulations should provide a quantity of modified RSV of the disclosure sufficient to effectively protect the host patient against serious or life-threatening RSV infection.

The RSV produced in accordance with the present disclosure can be combined with viruses of the other subgroup or strains to achieve protection against multiple RSV subgroups or strains, or protective epitopes of these strains can be engineered into one virus as described herein. Typically the different viruses will be in admixture and administered simultaneously, but may also be administered separately. For example, as the F glycoproteins of the two RSV subgroups differ by only about 11% in amino acid sequence, this similarity is the basis for a cross-protective immune response as observed in animals immunized with RSV or F antigen and challenged with a heterologous strain. Thus, immunization with one strain may protect against different strains of the same or different subgroup.

In some instances it may be desirable to combine the RSV vaccines of the disclosure with vaccines which induce protective responses to other agents, particularly other childhood viruses. For example, the RSV vaccine of the present disclosure can be administered simultaneously with parainfluenza virus vaccine, such as described in Clements et al., J. Clin. Microbiol. 29:1175-1182 (1991), incorporated herein by reference. In another aspect of the disclosure the RSV can be employed as a vector for protective antigens of other respiratory tract pathogens, such as parainfluenza, by incorporating the sequences encoding those protective antigens into the RSV genome or antigenome which is used to produce infectious RSV as described herein.

Single or multiple administrations of the vaccine compositions of the disclosure can be carried out. In neonates and infants, multiple, sequential administrations may be required to elicit sufficient levels of immunity. Administration may begin within the first month of life, or before, about two months of age, typically not later than six months of age, and at intervals throughout childhood, such as at two months, six months, one year and two years, as necessary to maintain sufficient levels of protection against native (wild-type) RSV infection. Similarly, adults who are particularly susceptible to repeated or serious RSV infection, such as, for example, health care workers, day care workers, family members of young children, the elderly (over 55, 60, or 65 years), individuals with compromised cardiopulmonary function, may require multiple immunizations to establish and/or maintain protective immune responses. Levels of induced immunity can be monitored by measuring amounts of neutralizing secretory and serum antibodies, and dosages adjusted or vaccinations repeated as necessary to maintain desired levels of protection. Further, different vaccine viruses may be advantageous for different recipient groups. For example, an engineered RSV strain expressing an additional protein rich in T cell epitopes may be particularly advantageous for adults rather than for infants.

In yet another aspect of the disclosure, RSV is employed as a vector for transient gene therapy of the respiratory tract. According to this embodiment, the recombinant RSV genome or antigenome incorporates a sequence which is capable of encoding a gene product of interest. The gene product of interest is under control of the same or a different promoter from that which controls RSV expression. The infectious RSV produced by coexpressing the recombinant RSV genome or antigenome with the N, P, L and M2-1 proteins and containing a sequence encoding the gene product of interest is administered to a patient. Administration is typically by aerosol, nebulizer, or other topical application to the respiratory tract of the patient being treated. Recombinant RSV is administered in an amount sufficient to result in the expression of therapeutic or prophylactic levels of the desired gene product. Examples of representative gene products which are administered in this method include those which encode, for example, those particularly suitable for transient expression, e.g., interleukin-2, interleukin-4, gamma-interferon, GM-CSF, G-CSF, erythropoietin, and other cytokines, glucocerebrosidase, phenylalanine hydroxylase, cystic fibrosis transmembrane conductance regulator (CFTR), hypoxanthine-guanine phosphoribosyl transferase, cytotoxins, tumor suppressor genes, antisense RNAs, and vaccine antigens.

In certain embodiments, the disclosure relates to immunogenic compositions (e.g., vaccines) comprising an immunologically effective amount of a recombinant RSV of the invention (e.g., an attenuated live recombinant RSV or inactivated, non-replicating RSV), an immunologically effective amount of a polypeptide disclosed herein, and/or an immunologically effective amount of a nucleic acid disclosed herein.

In certain embodiments, the disclosure relates to methods for stimulating the immune system of an individual to produce a protective immune response against RSV. In the methods, an immunologically effective amount of a recombinant RSV disclosed herein, an immunologically effective amount of a polypeptide disclosed herein, and/or an immunologically effective amount of a nucleic acid disclosed herein is administered to the individual in a physiologically acceptable carrier.

Typically, the carrier or excipient is a pharmaceutically acceptable carrier or excipient, such as sterile water, aqueous saline solution, aqueous buffered saline solutions, aqueous dextrose solutions, aqueous glycerol solutions, ethanol, or combinations thereof. The preparation of such solutions ensuring sterility, pH, isotonicity, and stability is effected according to protocols established in the art. Generally, a carrier or excipient is selected to minimize allergic and other undesirable effects, and to suit the particular route of administration, e.g., subcutaneous, intramuscular, intranasal, oral, topical, etc. The resulting aqueous solutions can e.g., be packaged for use as is or lyophilized, the lyophilized preparation being combined with a sterile solution prior to administration In certain embodiments, the RSV (or RSV components) is administered in a quantity sufficient to stimulate an immune response specific for one or more strains of RSV (e.g., an immunologically effective amount of RSV or an RSV component is administered). Preferably, administration of RSV elicits a protective immune response. Dosages and methods for eliciting a protective anti-viral immune response, adaptable to producing a protective immune response against RSV, are known to those of skill in the art. See, e.g., U.S. Pat. No. 5,922,326; Wright et al. (1982) Infect. Immun 37:397-400; Kim et al. (1973) Pediatrics 52:56-63; and Wright et al. (1976) J. Pediatr. 88:931-936. For example, virus can be provided in the range of about $10^3$-$10^6$ pfu (plaque forming units) per dose administered (e.g., $10^4$-$10^5$ pfu per dose administered). Typically, the dose will be adjusted based on, e.g., age, physical condition, body weight, sex, diet, mode and time of administration, and other clinical factors. The prophylactic vaccine formulation can be systemically administered, e.g., by subcutaneous or intramuscular injection using a needle and syringe or a needleless injection device. Preferably, the vaccine formulation is administered intranasally, e.g., by drops, aerosol (e.g., large particle aerosol (greater than about 10 microns)), or spray into the upper respiratory tract. While any of the above routes of delivery results in a protective systemic immune response, intranasal administration confers the added benefit of eliciting mucosal immunity at the site of entry of the virus. For intranasal administration, attenuated live virus vaccines are often preferred, e.g., an attenuated, cold adapted and/or temperature sensitive recombinant RSV, e.g., a chimeric recombinant RSV. As an alternative or in addition to attenuated live virus vaccines, killed virus vaccines, nucleic acid vaccines, and/or polypeptide subunit vaccines, for example, can be used, as suggested by Walsh et al. (1987) J. Infect. Dis. 155:1198-1204 and Murphy et al. (1990) Vaccine 8:497-502.

In certain embodiments, the attenuated recombinant RSV is as used in a vaccine and is sufficiently attenuated such that symptoms of infection, or at least symptoms of serious infection, will not occur in most individuals immunized (or otherwise infected) with the attenuated RSV—in embodiments in which viral components (e.g., the nucleic acids or polypeptides herein) are used as vaccine or immunogenic components. However, virulence is typically sufficiently abrogated such that mild or severe lower respiratory tract infections do not typically occur in the vaccinated or incidental host.

While stimulation of a protective immune response with a single dose is preferred, additional dosages can be administered, by the same or different route, to achieve the desired prophylactic effect. In neonates and infants, for example, multiple administrations may be required to elicit sufficient levels of immunity. Administration can continue at intervals throughout childhood, as necessary to maintain sufficient levels of protection against wild-type RSV infection. Similarly, adults who are particularly susceptible to repeated or serious RSV infection, such as, for example, health care workers, day care workers, family members of young children, the elderly, and individuals with compromised cardiopulmonary function may require multiple immunizations to establish and/or maintain protective immune responses. Levels of induced immunity can be monitored, for example, by measuring amounts of virus-neutralizing secretory and serum antibodies, and dosages adjusted or vaccinations repeated as necessary to elicit and maintain desired levels of protection.

Alternatively, an immune response can be stimulated by ex vivo or in vivo targeting of dendritic cells with virus. For example, proliferating dendritic cells are exposed to viruses in a sufficient amount and for a sufficient period of time to permit capture of the RSV antigens by the dendritic cells. The cells are then transferred into a subject to be vaccinated by standard intravenous transplantation methods.

Optionally, the formulation for prophylactic administration of the RSV also contains one or more adjuvants for enhancing the immune response to the RSV antigens. Suitable adjuvants include, for example: complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, bacille Calmette-Guerin (BCG), Corynebacterium parvum, and the synthetic adjuvant QS-21.

If desired, prophylactic vaccine administration of RSV can be performed in conjunction with administration of one or more immunostimulatory molecules. Immunostimulatory molecules include various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immunostimulatory molecules can be administered in the same formulation as the RSV, or can be administered separately. Either the protein or an expression vector encoding the protein can be administered to produce an immunostimulatory effect.

Although vaccination of an individual with an attenuated RSV of a particular strain of a particular subgroup can induce cross-protection against RSV of different strains and/or subgroups, cross-protection can be enhanced, if desired, by vaccinating the individual with attenuated RSV from at least two strains, e.g., each of which represents a different subgroup. Similarly, the attenuated RSV vaccines can optionally be combined with vaccines that induce protective immune responses against other infectious agents.

EXPERIMENTAL

The A2-line19F-I557V Virus is Immunogenic in BALB/c Mice

This is demonstrated in FIG. 7, which shows that this virus induces higher levels of RSV-neutralizing serum antibodies than RSV A2 and RSV A2-line19F. FIG. 7B demonstrates that, even low input doses, this virus provide complete protection to challenge with a heterologous strain of RSV, when challenged 29 days post-primary infection. This complete protection with low dose immunization is not seen for two other strains of RSV, A2-K-line19F and A2-K-A2GF, which allow for breakthrough reinfection. Those two viruses are similar to A2-line19F-1557V except for the F protein, indicating that the I557V F protein encoded by this virus is important for the phenotype.

In addition to being immunogenic (FIG. 7A), the A2-line19F-1557V virus is thermostable. Thermostability of the virus was measured as the ability of the virus to retain titer over multiple days when incubated at either 4° C. or 37° C. The results indicated indicate that this virus is more thermostable than the A2-K-A2GF virus at both temperatures tested and more stable than A2-line19F at 4° C. As stated above, the F gene is the only difference between these two viruses, indicating this unique F protein is responsible for the phenotype.

The A2-line 19 F RSV strain is more stable than the A2 strain, and Val at 557 in the context of the line 19 F protein makes the virus even more stable. Val at position 557 in other strains is also likely stabilizing—557 position and stability. In certain embodiments, the disclosure contemplates other mutations at position 557 (any amino acid, e.g., alanine, valine, isoleucine, leucine), in any F strain context, that affect thermostability of the virus.

Figure 1:
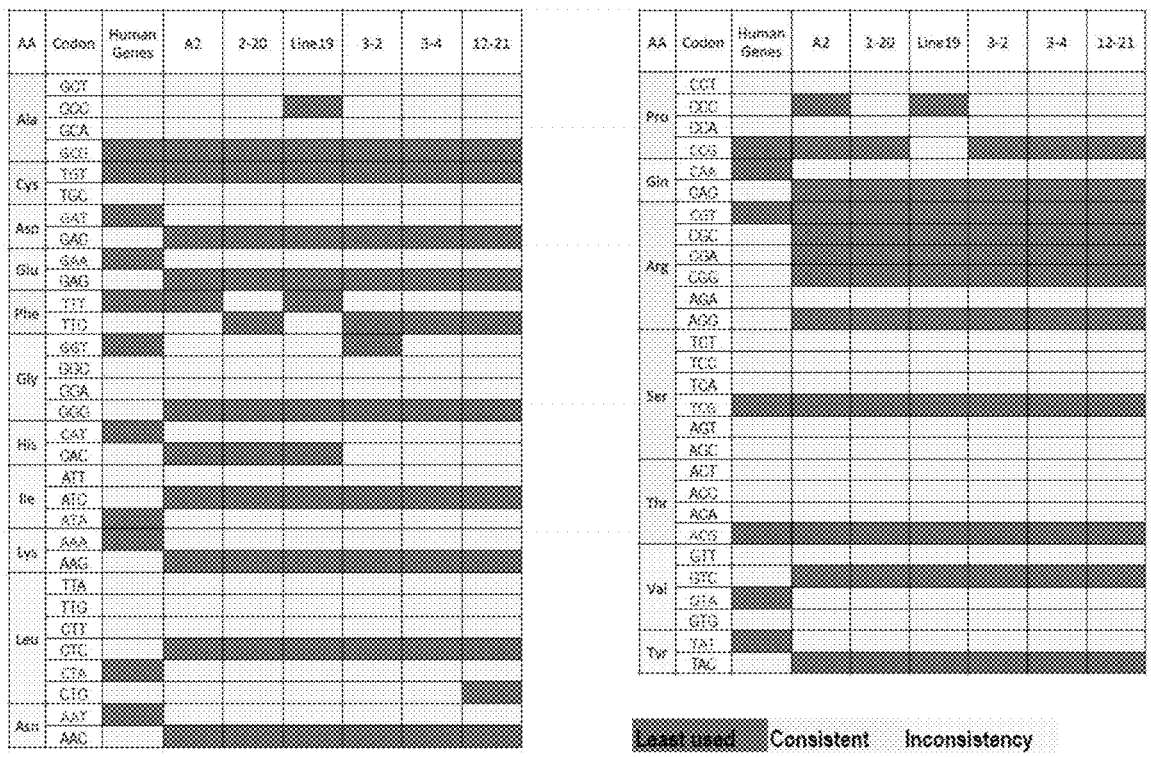
FIG. 1 shows a table with the least used codons in human genes and in specific RSV strains.

Generation of Recombinant RSV with NS1 and NS2 Codon Silent Mutations and Growth Attenuation Codons that are uncommon in humans were used to prepare recombinant RSV with the NS1 and NS2 genes designated dNS1h and dNS2h below. Codons that are uncommon in RSV were used to prepare recombinant RSV with the NS1 and NS2 genes designated dNS1v and dNS2v below. FIG. 1 provides a table used to determine optimal sequences. Recombinant RSV was prepared with the following nucleotide sequences for the NS1 and NS2 gene. It is important to note that prior to testing codons, it was unpredictable if either the uncommon human codons or uncommon RSV codons would produce a desirable RSV vaccine candidate. Experiments using codons uncommon for RSV sequences had the unanticipated and undesirable effect of increased expression. Using codons uncommon for human sequences had the desirable effect of decreased expression. Experiments comparing NS codons uncommon for human sequences and NS codons uncommon for RSV sequences indicated that the codons uncommon for human sequences were preferential for vaccine development.

dNS1h nucleotide sequence (SEQ ID NO: 6) has which as 84 out of 420 nucleotides (20%) different and 68 out of 140 codons (48%) than NS1 in wild-type A2

```
                                                SEQ ID NO: 6
ATGGGTTCGAATTCGCTATCGATGATAAAAGTACGTCTACAAAATCTATT

TGATAATGATGAAGTAGCGCTACTAAAAATAACGTGTTATACGGATAAAC

TAATACATCTAACGAATGCGCTAGCGAAAGCGGTAATACATACGATAAAA

CTAAATGGTATAGTATTTGTACATGTAATAACGTCGTCGGATATATGTCC

GAATAATAATATAGTAGTAAAATCGAATTTTACGACGATGCCGGTACTAC

AAAATGGTGGTTATATATGGGAAATGATGGAACTAACGCATTGTTCGCAA

CCGAATGGTCTACTAGATGATAATTGTGAAATAAAATTTTCGAAAAAACT

ATCGGATTCGACGATGACGAATTATATGAATCAACTATCGGAACTACTAG

GTTTTGATCTAAATCCGTAA
``` dNS1v nucleotide sequence (SEQ ID NO: 7) has which as 145 out of 420 nucleotides (34%) different and 122 out of 140 codons (87%) than NS1 in wild-type A2

SEQ ID NO: 7
ATGGGGTCGAACTCGCTCTCGATGATCAAGGTCCGCCTCCAGAATCTCTT

CGACAACGACGAGGTCGCGCTCCTCAAGATCACGTGTTACACGGACAAGC

TCATCCACCTCACGAACGCGCTCGCGAAGGCGGTCATCCACACGATCAAG

CTCAACGGGATCGTCTTCGTCCACGTCATCACGTCGTCGGACATCTGTCC

GAACAACAACATCGTCGTCAAGTCGAACTTCACGACGATGCCGGTCCTCC

AGAACGGGGGGTACATCTGGGAGATGATGGAGCTCACGCACTGTTCGCAG

CCGAACGGGCTCCTCGACGACAACTGTGAGATCAAGTTCTCGAAGAAGCT

CTCGGACTCGACGATGACGAACTACATGAACCAGCTCTCGGAGCTCCTCG

GGTTCGACCTCAACCCGTAA dNS2h nucleotide sequence (SEQ ID NO: 9) has which as 82 out of 420 nucleotides (21%) different and 73 out of 140 codons (58%) than NS1 in wild-type A2

SEQ ID NO: 9
ATGGATACGACGCATAATGATAATACGCCGCAACGTCTAATGATAACGGA

TATGCGTCCGCTATCGCTAGAAACGATAATAACGTCGCTAACGCGTGATA

TAATAACGCATAAATTTATATATCTAATAAATCATGAATGTATAGTACGT

AAACTAGATGAACGTCAAGCGACGTTTACGTTTCTAGTAAATTATGAAAT

GAAACTACTACATAAAGTAGGTTCGACGAAATATAAAAAATATACGGAAT

ATAATACGAAATATGGTACGTTTCCGATGCCGATATTTATAAATCATGAT

GGTTTTCTAGAATGTATAGGTATAAAACCGACGAAACATACGCCGATAAT

ATATAAATATGATCTAAATCCGTAA dNS2v nucleotide sequence (SEQ ID NO: 10) has which as 103 out of 420 nucleotides (27%) different and 92 out of 140 codons (73%) than NS1 in wild-type A2

SEQ ID NO: 10
ATGGACACGACGCACAACGACAACACGCCGCAGCGCCTCATGATCACGGA

CATGCGCCCGCTCTCGCTCGAGACGATCATCACGTCGCTCACGCGCGACA

TCATCACGCACAAGTTCATCTACCTCATCAACCACGAGTGTATCGTCCGC

AAGCTCGACGAGCGCCAGGCGACGTTCACGTTCCTCGTCAACTACGAGAT

GAAGCTCCTCCACAAGGTCGGGTCGACGAAGTACAAGAAGTACACGGAGT

ACAACACGAAGTACGGGACGTTCCCGATGCCGATCTTCATCAACCACGAC

GGGTTCCTCGAGTGTATCGGGATCAAGCCGACGAAGCACACGCCGATCAT

CTACAAGTACGACCTCAACCCGTAA

BEAS-2B cell lines at 60-70% confluence are infected with the recombinant virus indicated as above at MOI (multiplicity of infection) of 0.01 (i.e., for each 100 cells, there is one infectious virus particle). This is done by first counting the cells before infection, calculating the total number of cells in each well, then calculating the amount of each virus for infection. Infection is done at room temperature for 1 hour, then washed off. The infected cells are left in 37° C. incubator with 5% $CO_2$ for up to 96 hours. Samples are taken at 12, 24, 48, 72, and 96 hours after infection and frozen. After collecting all the time point samples, the amount of virus in each sample is determined by titering on Vero cell lines according to standard protocol and the titer (FFU/mL, meaning Fluorescent Focus-forming Unit per mL) is calculated for each sample. Since viruses used have a red fluorescent gene in the genome, the infected cells are counted under the fluorescent microscope providing fluorescent focus-forming units. Each data point represents duplicate samples from two independent experiments.

As illustrated in FIG. 2, growth of kRSV-dNS1h (human deoptimized NS1+NS2 virus) is attenuated in the BEAS-2B cell line at 72 and 96 hours post infection. It is believed that this is due to lower NS1 and NS2 proteins than wild type virus.

Expression of RSV in Plasmid Designed for Low Copy Number

Infectious recombinant RSV (rRSV) can be recovered from transfected plasmids. Co-expression of RSV N, P, L, and M2 1 proteins as well as the full-length antigenomic RNA is sufficient for RSV replication. Infectious RSV may be produced from the co-transfection of plasmids encoding N, P, L, and M2-1 proteins and the antigenomic cDNA under control of the T7 promoter into BHK-21 cells that stably express T7 RNA polymerase (BSR cells). Currently research labs typically use a RSV antigenomic cDNA cloned in the plasmid pBR322 (mid-range copy number, 15-20 copies per *E coli*). In order to maintain the antigenomic cDNA in this plasmid, the bacteria is grown at 30° C. and low aeration. Nevertheless, plasmid rearrangements and clone loss is frequently experienced.

A fraction of RSV cDNA containing the attachment glycoprotein (G) and fusion (F) genes of the virus was found to be unclonable in pUC-based plasmids (500-700 plasmid copies in *E coli*). This fragment was cloned in a low copy number (approximately 5 copies per *E. coli*) plasmid called pLG338-30.5. The plasmid pLG338-30 was developed to increase the stability of cloned lentivirus glycoproteins. Cunningham et al., Gene, 1993, 124, 93-98. It is hypothesized that cDNA instability in *E coli* results from the presence of cryptic *E coli* transcription promoters within viral glycoprotein sequences. Thus, instability of cDNA in "promoterless" plasmids in bacteria can arise because aberrant proteins are expressed from cryptic promoters, leading to toxicity exacerbated by plasmid copy number.

An antigenomic plasmid was generated containing the RSV strain A2 genome with the strain line 19 F gene in place of the A2 F gene. It had been derived from the antigenome plasmid first disclosed in Collins et al., Proc Natl Acad Sci USA., 1995, 92(25):11563-11567 and U.S. Pat. No. 6,790,449 hereby incorporated by reference. The antigenome was digested out of the plasmid vector and ligated into the pKBS3 BAC.

GalK recombineering reagents were obtained from the NCI and successfully established a BAC-RSV reverse genetics protocol (FIGS. 4 and 5). See http://web.ncifcrf.gov/research/brb/recombineeringInformation.aspx, hereby incorporated by reference. Mutation of RSV cDNA via BAC recombineering has enhanced the ability to manipulate RSV for generation of mutants. An added benefit of the system is enhanced stability of the full-length antigenomic cDNA in the BAC vector.

The BAC-based RSV antigenome vector was propagated at 32° C. and 250 RPM without observing any vector rearrangements or clone loss in *E coli*. Thus, BAC-RSV not only enables manipulations via recombineering but also facilitates RSV reverse genetics in general owing to elimination of cDNA instability.

RSV Antigenome in BAC Vector (pSynkRSV_Line 19 F Construction)

The RSV-BAC pSynkRSV_line 19 F contains the modified katushka gene (mKate2, fluorescent protein), and restriction sites for convenient standard cloning methods. To build pSynkRSV, three nucleic acid pieces were synthesized by Gene Art, a company that synthesizes DNA. These three pieces then have to be put together in the bacterial artificial chromosome (BAC). The three pieces are designated pSynkRSV-BstBI_SacI (#1), pSynkRSV-SacI_ClaI (#2), and pSynkRSV-ClaI_MluI (#3). One uses the plasmid pKBS3 as the backbone for constructing pSynkRSV. See FIGS. 6A-E. pSynkRSV contains the bacterial artificial chromosome sequences needed to regulate copy number and partitioning in the bacteria.

To insert the three synthesized segments, one puts oligonucleotide adapters into pKBS3 between two existing restriction enzyme cut sites, BstBI and MluI.

The overhangs were designed such that the adapter would ligate into pKBS3 at the BstBI and MluI sites. Underlined sequences indicate restriction sites: SacI, ClaI, and AvrII from right to left respectively. This produces a multi-cloning site containing the restriction sites BstBI, SacI, ClaI, AvrII, and MluI, in that order, and a plasmid termed pKBS5. See FIG. 6A. One cuts and ligates the SacI_ClaI segment (#2) from Gene Art into pKBS5. See FIG. 6B. The next one cuts and ligates the #3 segment using the enzymes AvrII and MluI (cannot use ClaI again due to an inactive ClaI restriction site in pSynkRSV-ClaI_MluI). See FIG. 6C. At this point, the plasmid pKBS5 contains the Gene Art sequences from SacI to ClaI, some intervening nucleotides (less than 10), and the Gene Art sequences from AvrII to MluI. One cuts and ligates the #1 segment using BstBI and SacI. See FIG. 6D. This RSV BAC contains about 10 unwanted nucleotides between two ClaI sites (that from segment #2 and segment #3). Recombineering is used to delete those nucleotides, thus generating pSynkRSV_line 19 F. See FIG. 6E. The three segments should be ligated in this order to avoid potential interference from multiple restriction sites.

Recombinant Respiratory Syncytial Virus (RSV) as Live-Attenuated Vaccine (LAV)

Four expression plasmids were generated, one that expresses RSV nucleoprotein (N), one that expresses RSV phosphoprotein (P), one that expresses RSV matrix 2 ORF 1 protein (M2-1), and one that expresses RSV large polymerase (L)-pA2-Nopt, pA2-Popt, pA2-M2-1opt, and pA2-Lopt. The nomenclature reflects the fact that these genes are of the A2 strain of RSV and that these cDNAs are optimized for human codon bias in order to increase expression levels in mammalian cells. Recovery of recombinant RSV from cDNA includes five components: full length RNA (e.g. provided by pSynk-RSV119F), and RSV N, P, M2-1, and L proteins. The four helpers plasmids pA2-Nopt, pA2-Popt, pA2-M2-1opt, and pA2-Lopt useful for driving RSV rescue.

A recombinant respiratory syncytial virus strain A2-line19F was generated with a point mutation at residue F557, at which the isoleucine was changed to a valine (virus name A2-line19F-I557V). A protein expression plasmid was also generated which encodes the line 19 F protein with the same isoleucine to valine mutation at position 557 (protein name—line 19F-I557V). A2-line19F-I557V has higher thermostability, at 4° C. and 37° C., than the A2-line 19F parent virus. This increased stability likely contributes to an increased induction of neutralizing antibodies and protection by A2-line19F-I557V relative to A2-line 19F.

Development of a live-attenuated RSV vaccine has been hindered by low RSV immunogenicity in young infants, which constitute the target population, and limited genomic stability. A desirable vaccine is immunogenic and genetically and thermally stable and safe for vaccination in young infants.

RSV nonstructural (NS) proteins 1 and 2 (NS1 and NS2) are associated with inhibition of host cell interferon pathways and thus potentially limiting the immunogenicity of the virus. The small hydrophobic (SH) glycoprotein forms cationic pores in membranes, modulates the host apoptotic pathways and inhibits tumor necrosis factor-a (TNF-a) signaling. SH, NS1 and NS2 are dispensable for virus replication. However, deletion of NS1 and NS2 together results in an over-attenuation. Deletion of the SH protein has little apparent effect on attenuation in experimental vaccine candidates currently being evaluated. However, deletion of SH enhances RSV replication in vitro and presumably enhances expression of downstream genes, such as the antigenic G and F genes.

RSV vaccine candidates disclosed herein combine multiple technologies to overcome the challenges of poor immunogenicity and limited genetic and thermal stability in a safe viral vaccine candidate. RSV LAV OE1 combines limited expression of immune inhibitory proteins NS1 and NS2 through codon-deoptimization and SH protein through deletion without the potential for rapid reversion in a stable and immunogenic viral background.

Vaccine candidates were generated using BAC-based RSV reverse genetics codon-deoptimization of nonstructural (NS) genes NS1 and NS2 were combined with the A2-line 19F gene containing a mutation at residue 557, as well as deletion of the RSV small hydrophobic (SH) glycoprotein.

OE1 Virus Genome (SEQ ID NO: 1)
RSV vaccine candidate genotype:
A2-mKate2-dNSh-deltaSH-A2G-line19F-I557V (tagged)
and A2-dNSh-deltaSH-A2G-line19F-I557V (untagged)

RSV attachment glycoprotein (G) is a heavily glycosylated protein, which exists in two variant forms: membrane-bound and secreted. Studies evaluating the functional role of RSV G have shown that it plays a role in inhibition of toll-like receptor activation and its secreted form likely acts as an immune antigen decoy. In addition to RSV F, G protein is also immunogenic, however due in part to its extensive glycosylation, it is a poor antigen for generation of neutralizing antibodies. RSV G is indispensible for virus replication, but deletion results in over-attenuation. Thus, G can be considered a non-essential virulence gene.

An RSV A2 G protein sequence was substituted which contains a M48I mutation and has 50% of the codons deoptimized [dGm(50%)] into the background of the RSV LAV OE1 virus genome. The OE2 virus background includes codon-deoptimization of nonstructural (NS) genes NS1 and NS2 with the A2-line 19F gene containing a mutation at amino acid residue 557, as well as deletion of the RSV small hydrophobic (SH) glycoprotein.

OE2 Virus Genome (SEQ ID NO: 2)
RSV vaccine candidate genotype:
A2-mKate2-dNSh-deltaSH-dGm(50%)-line19F-I557V (tagged)
and A2-dNSh-deltaSH-dGm(50%)-line19F-I557V (untagged)

RSV LAV OE2 combines reduced expression of immune inhibitory glycoprotein G through codon-deoptimization of 50% of codons, 100% codondeoptimization of immunomodulatory proteins NS1 and NS2, and deletion of SH protein without the potential for rapid reversion in a stable and immunogenic viral background.

In a third vaccine candidate, an RSV A2 G protein sequence substituted with one which contains a M48I mutation and has 75% of the codons deoptimized [dGm(75%)] into the background of the RSV LAV OE1 virus genome. The OE3 virus background includes codon-deoptimization of nonstructural (NS) genes NS1 and NS2 with the A2-line 19F gene containing a mutation at residue 557, as well as deletion of the RSV small hydrophobic (SH) glycoprotein.

OE3 Virus Genome (SEQ ID NO: 3)
RSV vaccine candidate genotype:
 A2-mKate2-dNSh-deltaSH-dGm(75%)-line19F-I557V (tagged)
 and A2-dNSh-deltaSH-dGm(75%)-line19F-I557V (untagged)

RSV LAV OE3 combines reduced expression of immune inhibitory glycoprotein G through codon-deoptimization of 75% of codons, 100% codon deoptimization of immunomodulatory proteins NS1 and NS2, and deletion of SH protein without the potential for rapid reversion in a stable and immunogenic viral background.

An RSV A2 G protein sequence which contains a M48I mutation and has 100% of the codons deoptimized [dGm (100%)] into the background of the RSV LAV OE1 virus genome was generated. The OE4 virus background includes codon-deoptimization of nonstructural (NS) genes NS1 and NS2 with the A2-line 19F gene containing a mutation at residue 557, as well as deletion of the RSV small hydrophobic (SH) glycoprotein.

OE4 Virus Genome (SEQ ID NO: 4)
RSV vaccine candidate genotype:
 A2-mKate2-dNSh-deltaSH-dGm(100%)-line19F-I557V (tagged)
 and A2-dNSh-deltaSH-dGm(100%)-line19F-I557V (untagged)

What is claimed is:

1. An isolated recombinant nucleic acid comprising a NS1 gene of the RSV genome, wherein the NS1 gene has at least 90% sequence identity to SEQ ID NO: 6; wherein the isolated nucleic acid encodes a NS1 protein having sequence as set forth in SEQ ID NO: 5.

2. A recombinant vector comprising a nucleic acid of claim 1.

3. A recombinant RSV comprising the nucleic acid of claim 1.

4. A recombinant RSV comprising a nucleic acid of claim 1 and further comprising a NS2 gene having at least 90% identity with SEQ ID NO 9 having sequence as set forth in SEQ ID NO: 8.

5. An expression system comprising an attenuated recombinant RSV of claim 3.

6. A vaccine comprising a recombinant RSV of claim 3.

* * * * *

SEQUENCE LISTING

```
Sequence total quantity: 21
SEQ ID NO: 1           moltype = DNA  length = 15573
FEATURE                Location/Qualifiers
source                 1..15573
                       mol_type = genomic DNA
                       organism = respiratory syncytial virus
SEQUENCE: 1
acgcgaaaaa atgcgtacaa caaacttgca taaaccaaaa aaatgggca  aataagaatt   60
tgataagtac cacttaaatt taactccctt gcttagcgat ggtgagcgag ctgattaagg  120
agaacatgca catgaagctg tacatggagg gcaccgtgaa caaccaccac ttcaagtgca  180
catccgaggg cgaaggcaag ccctacgagg gcacccagac catgagaatc aaggcggtcg  240
agggcggcc  tctcccttc  gccttcgaca tcctggctac cagcttcatg tacggcagca  300
aaaccttcat caaccacacc cagggcatcc ccgacttctt taagcagtcc ttccccgagg  360
gcttcacatg ggagagagtc accacatacg aagacggggg cgtgctgacc gctacccagg  420
acaccagcct ccaggacggc tgcctcatct acaacgtcaa gatcagaggg gtgaacttcc  480
catccaacgg ccctgtgatg cagaagaaaa cactcggctg ggaggcctcc accgagaccc  540
tgtaccccgc tgacggcggc ctggaaggca gagccgacat ggccctgaag ctcgtgggcg  600
ggggccacct gatctgcaac ttgaagacca catacagatc caagaaaccc gctaagaacc  660
tcaagatgcc cggcgtctac tatgtggaca aagactgga aagaatcaag gaggccgaca  720
aagagaccta cgtcgagcag cacgaggtgg ctgtggccag atactgcgac ctccctagca  780
aactggggca cagatgagta ttcaattata gttattaaaa acttaacaga agacaaaaat  840
ggggcaaata agaatttgat aagtaccact taaattaac  tcccttgctt agcgatgggt  900
tcgaattcgc tatcgatgat aaaagtacgt ctacaaaatc tatttgataa tgatgaagta  960
gcgctactaa aaataacgtg ttatacggat aaactaatac atctaacgaa tgcgctagcg 1020
aaagcggtaa tacatacgat aaaactaaat ggtatagtat ttgtacatgt aataacgtcg 1080
tcggatatat gtccgaataa taatatagta gtaaaatcga attttacgac gatgccggta 1140
ctacaaaatg gtggttatat atgggaaatg atggaactaa cgcattgttc gcaaccgaat 1200
ggtctactag atgataattg tgaaataaaa ttttcgaaaa aactatcgga ttcgacgatg 1260
acgaattata tgaatcaact atcggaacta ctaggttttg atctaaatcc gtaaattata 1320
attaatatca actagcaaat caatgtcact aacaccatta gttaataaa  aacttaacag 1380
aagacaaaaa tggggcaaat aaatcaattc agccaaccca accatggata cgacgcataa 1440
tgataatacg ccgcaacgtc taatgataac ggatatgcgt ccgctatcgc tagaaacgat 1500
aataacgtcg ctaacgcgtg atataataac gcataaattt atatatctaa taaatcatga 1560
atgtatagta cgtaaactag atgaacgtca agcgacgttt acgtttctag taaattatga 1620
aatgaaacta ctacataaag taggttcgac gaaatataaa aaatatacgg aatataatac 1680
gaaatatggt acgtttccga tgccgatatt tataaatcat gatggttttc tagaatgtat 1740
aggtataaaa ccgacgaaac atacgccgat aatatataaa tatgatctaa atccgtaaat 1800
ttcaacacaa tattcacaca atctaaaaca acaactctat gcataactat actccatagt 1860
ccagatggag cctgaaaatt atagtaattt aaaattaagg agagatataa gatagaagat 1920
ggggcaaata caaagatggc tcttagcaaa gtcaagttga atgatacact caacaaagat 1980
caacttctgt catccagcaa atacaccatc caacggagca caggagatag tattgatact 2040
cctaattatg atgtgcagaa acacatcaat aagttatgtg gcatgttatt aatcacagaa 2100
gatgctaatc ataaattcac tgggttaata ggtatgttat atgcgatgtc taggttagga 2160
agagaagaca ccataaaaat actcagagat gcgggatatc atgtaaaagc aaatggagta 2220
gatgtaacaa cacatcgtca agacattaat ggaaagaaa  tgaaatttga agtgttaaca 2280
ttggcaagct taacaactga aattcaaatc aacattgaga tagaatctag aaaatcctac 2340
aaaaaaatgc taaaagaaat gggagaggta gctccagaat acaggcatga ctctcctgat 2400
tgtgggatga taatattatg tatagcagca ttagtaataa ctaaattagc agcagggac  2460
agatctggtc ttacagccgt gattaggaga gctaataatg tcctaaaaa  tgaaatgaaa 2520
cgttacaaag gcttactacc caaggacata gccaacagct tctatgaagt gtttgaaaaa 2580
catcccact  ttaatgtatt ttttgttcat ttggtatag cacaatcttc taccagaggt 2640
ggcagtagag ttgaagggat ttttgcagga ttgtttatga atgcctatgg tgcagggcaa 2700
gtgatgttac ggtgggagt  cttagcaaaa tcagttaaaa atattatgtt aggacatgct 2760
agtgtgcaag cagaaatgga acaagttgtt gaggtttatg aatatgccca aaaattgggt 2820
ggtgaagcag gattctacca tatattgaac aacccaaaag catcattatt atctttgact 2880
```

```
caatttcctc acttctccag tgtagtatta ggcaatgctg ctggcctagg cataatggga   2940
gagtacagag gtacaccgag gaatcaagat ctatatgatg cagcaaaggc atatgctgaa   3000
caactcaaag aaaatggtgt gattaactac agtgtactag acttgacagc agaagaacta   3060
gaggctatca aacatcagct taatccaaaa gataatgatg tagagctttg agttaataaa   3120
aatggggca aataaatcat catggaaaag tttgctcctg aattccatgg agaagatgca   3180
aacaacaggg ctactaaatt cctagaatca ataaagggca aattcacatc acccaaagat   3240
cccaagaaaa aagatagtat catatctgtc aactcaatag atatagaagt aaccaaagaa   3300
agccctataa catcaaattc aactattatc aacccaacaa atgagacaga tgatactgca   3360
gggaacaagc ccaattatca aagaaaacct ctagtaagtt tcaaagaaga ccctacacca   3420
agtgataatc ccttttctaa actatacaaa gaaaccatag aaacatttga taacaatgaa   3480
gaagaatcca gctattcata cgaagaaata aatgatcaga caaacgataa tataacagca   3540
agattagata ggattgatga aaaattaagt gaaatactag gaatgcttca cacattagta   3600
gtggcaagtg caggacctac atctgctcgg gatggtataa gagatgccat gattggttta   3660
agagagaaa tgatagaaaa aatcagaact gaagcattaa tgaccaatga cagattagaa   3720
gctatggcaa gactcaggaa tgaggaaagt gaaagatgg caaaagacac atcagatgaa   3780
gtgtctctca atccaacatc agagaaattg aacaacctat tggaagggaa tgatagtgac   3840
aatgatctat cacttgaaga tttctgatta gttaccactc ttcacatcaa cacacaatac   3900
caacagaaga ccaacaaact aaccaaccca atcatccaac caaatcatcc tccgccaatc   3960
agccaaacag ccaacaaaac aaccagccaa tccaaaacta accacccgga aaaaatctat   4020
aatatagtta caaaaaaagg aaagggtggg gcaaatatgg aaacatacgt gaacaagctt   4080
cacgaaggct ccacatacac agctgctgtt caatacaatg tcttagaaaa agacgatgac   4140
cctgcatcac ttacaatatg ggtgcccatg ttccaatcat ctatgccagc agatttactt   4200
ataaaagaac tagctaatgt caacatacta gtgaaacaaa tatccacacc caagggacct   4260
tcactaagag tcatgataaa ctcaagaagt gcagtgctag cacaaatgcc cagcaaattt   4320
accatatgcg ctaatgtgtc cttggatgaa agaagcaaac tagcatatga tgtaaccaca   4380
cctgtgaaa tcaaggcatg tagtctaaca tgcctaaaat caaaaaatat gttgactaca   4440
gttaaagatc tcactatgaa gacactcaac cctacacatg atattattgc tttatgtgaa   4500
tttgaaaaca tagtaacatc aaaaaaagtc ataataccaa catacctaag atccatcagt   4560
gtcagaaata aagatctgaa cacacttgaa aatataacaa ccactgaatt caaaaatgct   4620
atcacaaatg caaaaatcat cccttactca ggattactat tagtcatcac agtgactgac   4680
aacaaaggag cattcaaata cataaagcca caaagtcaat tcatagtaga tcttggagct   4740
tacctagaaa agaaagtat atattatgtt accacaaatt ggaagcacac agctacacga   4800
tttgcaatca aacccatgga agattaacct ttttcctcta catcagtgtg ttaattcata   4860
caaactttct acctacattc ttcacttcac catcacaatc acaaacactc tgtggttcaa   4920
ccaatcaaac aaaacttatc tgaagtccca gatcatccca agtcattgtt tatcagatct   4980
agtactcaaa taagttaata aaaaatatac acatggacgt ccatggggca aatgcaaaca   5040
tgtccaaaaa caaggaccaa cgcaccgcta agacattaga aaggacctgg gacactctca   5100
atcatttatt attcatatca tcgtgcttat ataagttaaa tcttaaatct gtagcacaaa   5160
tcacattate cattctggca atgataatct caacttcact tataattgca gccatcatat   5220
tcatagcctc ggcaaaccac aaagtcacac caacaactgc aatcatacaa gatgcaacaa   5280
gccagatcaa gaacacaacc ccaacatacc tcacccagaa tcctcagctt ggaatcagtc   5340
cctctaatcc gtctgaaatt acatcacaaa tcaccaccat actagcttca acaacaccag   5400
gagtcaagtc aaccctgcaa tccacaacag tcaagaccaa acaactcaga   5460
cacaacccag caagcccacc acaaacaac gccaaaacaa accaccaagc aaacccaata   5520
atgattttca ctttgaagtg ttcaactttg taccctgcag catatgcagc aacaatccaa   5580
cctgctgggc tatctgcaaa agaataccaa acaaaaaacc aggaaagaaa accactacca   5640
agcccacaaa aaaaccaacc ctcaagacaa ccaaaaaaga tcccaaacct caaacctacta   5700
aatcaaagga agtacccacc accaagccca cagaagagcc aaccatcaac accaccaaaa   5760
caaacatcat aactacacta ctcacctcca acaccacagg aaatcagaa ctcacaagtc   5820
aaatggaaac cttccactca acttcctccg aaggcaatcc aagcccttct caagtctcta   5880
caacatccga gtacccatca caaccttcat ctccacccaa cacaccacgc cagtagttac   5940
ttaaaaacat attatcacaa aaggccttga ccaccgcgg agaatcaaaa taaactctgg   6000
ggcaaataac aatggagttg ccaatcctca aagcaaatgc aattaccaca atcctcgctg   6060
cagtcacatt ttgctttgct tctagtcaaa acatcactga agaattttat caatcaacat   6120
gcagtgcagt tagcaaaggc tatcttagtg ctctaagaac tggttggtat actagtgtta   6180
taactataga attaagtaat atcaagaaaa ataagtgtaa tggaacagat gctaaggtaa   6240
aattgatgaa acaagaatta gataaatata aaaatgctgt aacagaattg cagttgctca   6300
tgcaaagcac accagcagca aacaatcgag ccagaagaga actaccaagg tttatgaatt   6360
atacactcaa caataccaaa aaaccaatg taacattaag caagaaaagg aaaagaaagat   6420
ttcttggttt tttgttaggt gttggatctg caatcgccag tggcattgct gtatctaagg   6480
tcctgcactt agaaggagaa gtgaacaaga tcaaaagtgc tctactatcc acaaacaagg   6540
ccgtagtcag cttatcaaat ggagttagtg tcttaaccag cagagtgtta gacctcaaaa   6600
actatataga taaacaattg ttaccattg tgaataagca aagctgcaga atatcaaata   6660
tagaaactgt gatagagttc caacaaaaga acaacagact actagagatt accagggaat   6720
ttagtgttaa tgcaggtgta actacacctg taagcactta catgttaact aatagtgaat   6780
tattgtcatt aatcaatgat atgcctaaa caaatgatca gaaaaagtta atgtccaaca   6840
atgttcaaat agttagacag caaagttact ctatcatgtc cataataaaa gaggaagtct   6900
tagcatatgt agtacaatta ccactatgt gtgtgataga tacacccttgt tggaaattac   6960
acacatcccc ctatgtacaa accaacacaa aagaaggtc aaacatctgt ttaacaagaa   7020
ctgacagagg atggtactgt gacaatgcag gatcagtatc tttcttccca caagctgaaa   7080
aatgtaaagt tcaatcgaat cgagtatttt gtgacacaat gtacagttta acattaccaa   7140
gtgaagtaaa tctctgcaat gttgacatat tcaatcccaa atatgattgt aaaattatga   7200
cttcaaaac agatgtaagc agctccgtta tcacatctct aggagccatt gtgtcatgct   7260
atggcaacaa taaatgtaca gcatccaata aaaatcgtga aatcataaag acattttcta   7320
acgggtgtga ttatgtatca aataaggggt ggacactgt gtctgtaggt aacacattat   7380
attatgtaaa taagcaagaa ggcaaaagtc tctatgtaaa aggtgaacca ataataaatt   7440
tctatgaccc attagtattc ccctctgatg aatttgatgc atcaatatct caagtcaatg   7500
agaagattaa ccagagttta gcatttattc gtaaatccga tgaattatta cataatgtaa   7560
atgctggtaa atcaaccaca aatatcatga taactactat aattatagtg attatagtaa   7620
```

-continued

```
tattgttatc attaattgct gttggactgc tcctatactg taaggccaga agcacaccag    7680
tcacactaag caaggatcaa ctgagtggta taaataatat tgcatttagt aactgaataa    7740
aaatagcacc taatcatgtt cttacaatgg tttactatct gctcatagac aacccatcta    7800
tcattggatt ttcttaaaat ctgaacttca tcgaaactct tatctataaa ccatctcact    7860
tacactattt aagtagattc ctagtttata gttatataaa acacaattga atgccagtcg    7920
accttaccat ctgtaaaaat gaaaactggg gcaaatatgt cacgaaggaa tccttgcaaa    7980
tttgaaattc gaggtcattg cttaaatggt aagaggtgtc attttagtca taattatttt    8040
gaatggccac cccatgcact gcttgtaaga caaaacttta tgttaaacag aatacttaag    8100
tctatggata aaagtataga taccttatca gaaataagtg gagctgcaga gttggacaga    8160
acagaagagt atgctcttgg tgtagttgga gtgctagaga gttatatagg atcaataaac    8220
aatataacta aacaatcagc atgtgttgcc atgagcaaac tcctcactga actcaatagt    8280
gatgatatca aaaagctgag ggacaatgaa gagctaaatt cacccaagat aagagtgtac    8340
aatactgtca tatcatatat tgaaagcaac aggaaaaaca ataaacaaac tatcctatctg   8400
ttaaaaagat tgccagcaga cgtattgaag aaaaccatca aaaacacatt ggatatccat    8460
aagagcataa ccatcaacaa cccaaaagaa tcaactgtta gtgatacaaa tgaccatgcc    8520
aaaaataatg atactacctg acaaatatcc ttgtagtata acttccatac taataacaag    8580
tagatgtaga gttactatgt ataatcaaaa gaacacacta tatttcaatc aaaacaaccc    8640
aaataaccat atgtactcac cgaatcaaac attcaatgaa atccattgga cctctcaaga    8700
attgattgac acaattcaaa attttctaca acatctaggg attattgagg atatatatac    8760
aatatatata ttagtgtcat aacactcaat tctaacactc accacatcgt tacattatta    8820
attcaaacaa ttcaagttgt gggacaaaat ggatcccatt attaatggaa attctgctaa    8880
tgtttatcta accgatagtt attaaaagg tgttatctct ttctcagagt gtaatgcttt     8940
aggaagttac atattcaatg gtccttatct caaaaatgat tataccaact taattagtag    9000
acaaaatcca ttaatagaac acatgaatct aagaaactaa atataacac agtccttaat     9060
atctaagtat cataaaggtg aaataaaatt agaagaacct acttattttc agtcattact    9120
tatgcacatac aagagtatga cctcgtcaga acagattgct accactaatt tacttaaaaa   9180
gataatcaaga agagctatag aaataagtga tgtcaaagtc tatgctatat tgaataaact    9240
agggcttaaa gaaaaggaca agattaaatc caacaatgga caagatgaag acaactcagt    9300
tattcgacc ataatcaaag atgatatact ttcagctgtt aaagataatc aatctcatct     9360
taaagcagac aaaatcact ctacaaaaca aaagacaca atcaaaacaa cactcttgaa      9420
gaaattgatg tgttcaatgc aacatcctcc atcatggtta atacattggt ttaacttata    9480
cacaaaatta aacaacatat taacacagta tcgatcaaat gaggtaaaaa accatgggtt    9540
tacattgata gataatcaaa ctcttagtgg atttcaattt attttgaacc aatatgggttg   9600
tatagttat cataaggaac tcaaaagaat tactgtgaca acctatatc aattcttgac      9660
atggaaagat attagcctta gtagattaaa tgtttgttta attacatgga ttagtaactg    9720
cttgaacaca ttaaataaaa gcttaggctt aagatgcgga ttcaataatg ttatcttgac    9780
acaactattc ctttatggag attgtatact aaagctattt cacaatgagg ggttctacat    9840
aataaaagag gtagagggat ttattatgtc tctaatttta aatataacag aagaagatca    9900
attcagaaaa cgattttata acagtagct caacaacatc acagatgctg tctaataaagc    9960
tcagaaaaat ctgctatcaa gagtatgtca tacattatta gataagacag tgtccgataa    10020
tataataaat ggcagatgga taattctatt aagtaagttc cttaaattaa ttaagcttgc   10080
aggtgacaat aaccttaaca atctgagtga actatatttt ttgttcagaa tatttggaca   10140
cccaatggta gatgaaagac aagccatgga tgctgttaaa attaattgca atgagaccaa   10200
attttacttg ttaagcagtc tgagtatgtt aagaggtgcc tttatatata gaattataaa   10260
agggtttgta ataattaca acagatggcc tactttaaga aatgctattg ttttaccctt    10320
aagatggtta acttactata aactaaacac ttatccttct ttgttggaac ttacagaaag   10380
agatttgatt ctgttatcag gactacgttt ctatcgtgag tttcggttgc ctaaaaaagt   10440
ggatcttgaa atgattataa atgataaagc tatatccct cctaaaaatt tgatatggca    10500
tagtttccct agaaattaca tgccatcaca catacaaaac tatatagaac atgaaaaatt   10560
aaaatttcc gagagtgata aatcaagaag agtattagag tattatttaa gagataacaa    10620
attcaatgaa tgtgatttat acaactgtgt agttaatcaa agttatctca acaaccctaa   10680
tcatgtggta tcattgacag gcaaagaaag agaactcagt gtaggtagaa tgtttgcaat   10740
gcaaccggga atgttcagac aggttcaaat attggcagag aaaatgatag ctgaaaacat   10800
tttacaattc tttcctgaaa gtcttacaag atatggtgat ctagaactac aaaaaatatt   10860
agaattgaaa gcaggaataa gtaacaaatc aaatcgctac aatgataatt acaacaatta   10920
cattagtaag tgctctatca tcacagatct cagcaaattc aatcaagcat ttcgatatga   10980
aacgtcatgt atttgtagtg atgtgctgga tgaactgcat ggtgtacaat ctctattttc   11040
ctggttacat ttaactattc ctcatgtcac aataatatgc acatataggc atgcaccccc   11100
ctatatagga gatcatattg tagatctta caatgtagat gaacaaagtg gattatatag   11160
atatcacatg ggtggcatcg aagggtggtg tcaaaactg tggaccatag aagctatatc    11220
actattggat ctaatatctc tcaaagggaa attctcaatt actgctttaa ttaatggtga   11280
caatcaatca atagatataa gcaaccaat cagactcatg gaaggtcaaa ctcatgctca    11340
agcagattat ttgctagcat taaatagcct taaattactg tataaagagt atgcaggcat   11400
aggccacaaa ttaaaggaa ctgagactta tatcaccgat agtatcaat ttatgagtaa     11460
aacaattcaa cataacggtg tatattaccc agctagtata aagaaagtcc taagagtggg   11520
accgtggata aacactatac ttgatgattt caagtgagt ctagaatcta taggtagttt    11580
gacacaagaa ttagaatata gaggtgaaag tctattatgc agtttaatat ttagaaatgt   11640
atggttatat aatcagattg ctctacaatt aaaaaaatcat gcattatgta acaataaact   11700
atatttggac atattaaagg ttctgaaaca cttaaaaacc ttttttaatc ttgataatat   11760
tgatacagca ttaacattgt atatgaattt acccatgtta tttggtggtg gtgatcccaa   11820
cttgttatat cgaagtttct ataagaagaac tcctgacttc ctcacagagg ctatagttca   11880
ctctgtgttc atcttagtt attatacaaa ccatgactta aagataaac ttcaagatct     11940
gtcagatgat agattgaata agttcttaac atgcataatc acgtttgaca aaaacccaa     12000
tgctgaattc gtaactcatt gatgagagatcc tcaagcttga gggtctgaga gacaagctaa  12060
aattactagc gaaatcaata gactggcagt tacagaggtt ttgagtacag ctccaaacaa    12120
aatattctcc aaaagtgcac aacattatac tactacagag atagatcaa atgatatat      12180
gcaaatatata gaacctacat atcctcatgg gctaagagtt gtttatgaaa gttaccctt    12240
ttataaagca gagaaatag taaatcttat atcaggtaca aaatctataa ctaacatact    12300
ggaaaaaact tctgccatag acttaacaga tattgataga gccactgaga tgatgaggaa   12360
```

-continued

```
aaacataact ttgcttataa ggatacttcc attggattgt aacagagata aagagagat   12420
attgagtatg gaaaacctaa gtattactga attaagcaaa tatgttaggg aaagatcttg   12480
gtctttatcc aatatagttg gtgttacatc acccagtatc atgtatacaa tggacatcaa   12540
atatactaca agcactatat ctagtggcat aattatagag aaatataatg ttaacagttt   12600
aacacgtggt gagagaggac ccactaaacc atgggttggt tcatctacac agagaaaaa   12660
aacaatgcca gtttataata gacaagtctt aaccaaaaaa cagagagatc aaatagatc   12720
attagcaaaa ttggattggg tgtatgcatc tatagataac aaggatgaat tcatggaaga   12780
actcagcata ggaaccctg ggttaacata tgaaaaggcc aagaaattat ttccacaata   12840
tttaagtgtc aattatttgc atcgccttac agtcagtagt agaccatgtg aattccctac   12900
atcaataccag gcttatagaa caacaaatta tcactttgac actagcccta ttaatcgcat   12960
attaacagaa aagtatggtg atgaagatat tgacatagta ttccaaaact gtataagctt   13020
tggccttagt ttaatgtcag tagtagaaca atttactaat gtatgtccta acagaattat   13080
tctcatacct aagcttaatg agatacattt gatgaaacct cccatattca caggtgatgt   13140
tgatattcac aagttaaaac aagtgataca aaaacagcat atgtttttac cagacaaaat   13200
aagtttgact caatatgtgg aattattctt aagtaataaa acactcaaat ctggatctca   13260
tgttaattct aattaatat tggcacataa aatatctgac tattttcata atacttacat   13320
tttaagtact aatttagctg acattggat tctgattata caacttatga aagattctaa   13380
aggtatttt gaaaaagatt ggggagaggg atatataact gatcatatgt ttattaattt   13440
gaaagttttc ttcaatgctt ataagaccta tctcttgtgt tttcataaag gttatggcaa   13500
agcaaagctg gagtgtgata tgaacacttc agatcttcta tgtgtattgg aattaataga   13560
cagtagttat tggaagtcta tgtctaaggt attttttaaa caaaaagtta tcaaatacat   13620
tcttagccaa gatgcaagtt tacatagagt aaaaggatgt catagcttca aattatggtt   13680
tcttaaacgt cttaatgtag cagaattcac agtttgccct tgggttgtta acatagatta   13740
tcatccaaca catatgaaag caatattaac ttatatagat cttgttagaa tgggattgat   13800
aaatatagat agaatacaca ttaaaaataa acacaaattc aatgatgaat tttatacttc   13860
taatctcttc tacattaatt ataacttctc agataataact catctattaa ctaaacatat   13920
aaggattgct aattctgaat tagaaaataa ttacaacaaa ttatatcatc ctacaccaga   13980
aaccctagag aatatactag ccaatccgat taaaagtaat gacaaaaaga cactgaatga   14040
ctattgtata ggtaaaaatg ttgactcaat aatgttacca ttgttatcta ataagaagct   14100
tattaaatcg tctgcaatga ttagaaccaa ttacagcaaa caagatttgt ataatttatt   14160
ccctatggtt gtgattgata gaattataga tcattcaggc aatacagcca aatccaacca   14220
acttacact actacttccc accaaaatatc tttagtgcac aatagcacat cactttactg   14280
catgcttcct tggcatcata ttaatagatt caattttgta tttagttcta caggttgtaa   14340
aattagtata gagtatattt taaaagatct taaaattaaa gatcccaatt gtatagcatt   14400
cataggtgaa ggagcaggga atttattatt gcgtacagta gtggaacttc atcctgacat   14460
aagatatatt tacagaagtc tgaaagattg caatgatcat agtttaccta ttgagttttt   14520
aaggctgtac aatggacata tcaacattga ttatggtgaa aatttgacca ttcctgctac   14580
agatgcaacc aacaacattc attggtctta tttacatata aagtttgctg aacctatcag   14640
tcttttgtc tgtgatgccg aattgtctgt aacagtcaac tggagtaaaa ttataataga   14700
atggagcaag catgtaagaa agtgcaagta ctgttcctca gttaataat gtatgttaat   14760
agtaaaatat catgctcaag atgatattga tttcaaatta gacaatataa ctatattaaa   14820
aacttatgta tgcttaggca gtaagttaaa gggatcggag gtttacttag tccttacaat   14880
aggtcctgcg aatatattcc cagtatttaa tgtagtacaa aatgctaaat tgatactatc   14940
aagaaccaaa aatttcatca tgcctaagaa agctgataaa gagtctattg atgcaaatat   15000
taaaagtttg atcccctttc tttgttaccc tataacaaaa aaggaatta atactgcatt   15060
gtcaaaacta aagagtgttg ttagtggaga tatactatca tattctatag ctggacgtaa   15120
tgaagttttc agcaataaac ttataaatca taagcatatg aacatcttaa aatggttcaa   15180
tcatgttttta aatttcagat caacagaact aaactataac catttatata tggtagaatc   15240
tacatatcct tacctaagtg aattgttaaa cagcttgaca accaatgaac ttaaaaaact   15300
gattaaaatc acaggtagtc tgttatacaa ctttcataat gaataatgaa taaagatctt   15360
ataataaaa ttcccatagc tatacactaa cactgtattc aattatagtt attaaaaatt   15420
aaaaatcgta cgatttttta aataactttt agtgaactaa tcctaaagtt atcatttaa   15480
tcttggagga ataaatttaa acccctaatct aattggttta tatgtgtatt aactaaatta   15540
cgagatatta gttttgaca ctttttttct cgt                                15573
```

SEQ ID NO: 2          moltype = DNA   length = 15573
FEATURE               Location/Qualifiers
source                1..15573
                      mol_type = genomic DNA
                      organism = respiratory syncytial virus
SEQUENCE: 2

```
acgcgaaaaa atgcgtacaa caaacttgca taaaccaaaa aaatgggca ataagaatt    60
tgataagtac cacttaaatt taactccctt gcttagcgat ggtgagcgag ctgattaagg   120
agaacatgca catgaagctg tacatggagg gcaccgtgaa caaccaccac ttcaagtgca   180
catccgaggg cgaaggcaag ccctacgagg gcacccagac catgagaatc aaggcggtca   240
agggcggccc tctcccttc gccttcgaca tcctggctac cagcttcatg tacggcagca   300
aaaccttcat caaccacacc cagggcatcc ccgacttctt taagcagtcc ttccccgagg   360
gcttcacatg ggagagagtc accacatacg aagacgggg cgtgctgacg gctaccagg   420
acaccagcct ccaggacggc tgcctcatct acaacgtcaa gatcagaggg gtgaacttca   480
catccaacgg ccctgtgatg cagaagaaaa cactcggctg ggaggcctcc accgagaccc   540
tgtaccccgc tgacgcggc ctggaaggca gccgacat ggccctgaag ctcgtgggcg   600
ggggccacct gatctgcaac ttgaagacca catacagatc caagaaaccc gctaagaacc   660
tcaagatgcc cggcgtctac tatgtggaca gaagactgga agaatcaag gaggccgaca   720
aagagaccta cgtcgagcag cacgagtcg ctgtggccag actgcgcac ctccctaca   780
aactggggca cagatgagta ttcaattata gttattaaaa acttaacaga agacaaaat   840
ggggcaaata gaatttgat aagtaccact taaatttaac tcccttgctt agcgatgggt   900
tcgaattcgc tatcgatgat aaaagtacgt ctacaaaatc tatttgataa tgatgaagta   960
gcgctactaa aataacgtg ttatacggat aaactaaatc atctaacgaa tgcgctagcg  1020
aaagcggtaa tacatacgat aaaactaaat ggtatagtat ttgtacatgt aataacgtcg  1080
```

```
tcggatatat gtccgaataa taatatagta gtaaaatcga attttacgac gatgccggta   1140
ctacaaaatg gtggttatat atgggaaatg atggaactaa cgcattgttc gcaaccgaat   1200
ggtctactag atgataattg tgaaataaaa ttttcgaaaa aactatcgga ttcgacgatg   1260
acgaattata tgaatcaact atcggaacta ctaggttttg atctaaatcc gtaaattata   1320
attaatatca actagcaaat caatgtcact aacaccatta gttaatataa aacttaacag   1380
aagacaaaaa tggggcaaat aaatcaattc agccaaccca accatggata cgacgcataa   1440
tgataatacg ccgcaacgtc taatgataac ggatatgcgt ccgctatcgc tagaaacgat   1500
aataacgtcg ctaacgcgtg atataataac gcataaattt atatatctaa taaatcatga   1560
atgtatagta cgtaaactag atgaacgtca agcgacgttt acgtttctag taaattatga   1620
aatgaaacta ctacataaag taggttcgac gaaatataaa aaatatacgg aatataatac   1680
gaaatatggt acgtttccga tgccgatatt tataaatcat gatggttttc tagaatgtat   1740
aggtataaaa ccgacgaaac atacgccgat aatatataaa tatgatctaa atccgtaaat   1800
ttcaacacaa tattcacaca atctaaaaca acaactctat gcataactat actccatagt   1860
ccagatggag cctgaaaatt atagtaattt aaaattaagg agagatataa gatagaagat   1920
ggggcaaata caaagatggc tcttagcaaa gtcaagttga atgatacact caacaaagat   1980
caacttctgt catccagcaa atacaccatc caacggagca caggagatag tattgatact   2040
cctaattatg atgtgcagaa acacatcaat aagtatgtg gcatgttatt aatcacagaa   2100
gatgctaatc ataaattcac tgggttaata ggtatgttat atgcgatgtc taggttagga   2160
agagaagaca ccataaaaat actcagagat gcgggatatc atgtaaaagc aaatggagta   2220
gatgtaacaa cacatcgtca agacattaat ggaaaagaaa tgaaatttga agtgttaaca   2280
ttggcaagct taacaactga aattcaaatc aacattgaga tagaatctag aaaatcctac   2340
aaaaaaatgc taaaagaaat gggagaggta gctccagaat acaggcatga ctctcctgat   2400
tgtgggatga taatattatg tatagcagca ttagtaataa ctaaattagc agcaggggac   2460
agatctggtc ttacagccgt gattaggaga gctaataatg tcctaaaaaa tgaaatgaaa   2520
cgttacaaag gcttactacc caaggacata gccaacagct ctatgaagt gtttgaaaaa   2580
catccccact ttatagatgt ttttgttcat tttggtatta caccaatcttc taccagaggt   2640
ggcagtagag ttgaagggat ttttcagga ttgtttatga atgcctatgg tgcagggcaa   2700
gtgatgttac ggtggggagt cttagcaaaa tcagttaaaa atattatgtt aggacatgct   2760
agtgtgcaag cagaaatgga acaagttgtt gaggtttatg aatatgccca aaaattgggt   2820
ggtgaagcag gattctacca tatattgaac aacccaaaag catcattatt atctttgact   2880
caatttcctc acttctccag tgtagtatta ggcaatgctg ctggcctagg cataatggga   2940
gagtacagag gtacaccgag gaatcaagat ctatatgatg cagcaaaggc atatgctgaa   3000
caactcaaag aaaatggtgt gattaactac agtgtactag acttgacagc agaagaacta   3060
gaggctatca aacatcagct taatccaaaa gataatgatg tagagctttg agttaataaa   3120
aatggggca aataaatcat catggaaaag tttgctcctg aattccatgg agaagtgca   3180
aacaacaggg ctactaaatt cctagaatca ataagggca aattcacatc acccaaagat   3240
cccaagaaaa aagatagtat catatctgtc aactcaatag atatagaagt aaccaaagaa   3300
agccctataa catcaaattc aactattatc aacccaacaa atgagacaga tgatactgc   3360
gggaacaagc ccaattatca aagaaacct ctagtaagtt tcaaagaaga ccctacacca   3420
agtgataatc ccttttctaa actatacaaa gaaaccatag aaacatttga taacaatgaa   3480
gaagaatcca gctattcata cgaagaaata aatgatcaga caaacgataa tataacagca   3540
agattagata ggattgatga aaattaagt gaaatactag gaatgcttca cacattagta   3600
gtggcaagtg caggacctac atctgctcgg gatggtataa agacgatgac gattggttta   3660
agagaagaaa tgatagaaaa aatcagaact gaagcattaa tgaccaatga cagattagaa   3720
gctatgcaa gactcaggaa tgaggaaagt gaaaagatgg caaaagacac atcagatgaa   3780
gtgtctctca atccaacatc agagaaattg aacaacctat tggaaggaa tgatagtgac   3840
aatgatctat cacttgaaga tttctgatta gttaccactc ttcacatcaa cacacaatac   3900
caacagaaga ccaacaaact aaccaaccca atcatccaac caaacatcca tccgccaatc   3960
agccaaacag ccaacaaaac aaccagccaa tccaaaacta accaccgga aaaaatctat   4020
aatatagtta caaaaaagg aaagggtggg gcaaatatgg aaacatacgt gaacaagctt   4080
cacgaaggct ccacatacac agctgctgtt caatacaatg tcttagaaaa agacgatgac   4140
cctgcatcac ttacaatatg ggtgcccatg ttccaatcat ctatgccagc agatttactt   4200
ataaaagaac tagctaatgt caacatacta gtgaaacaaa tatccacacc caagggacct   4260
tcactaagag tcatgataaa ctcaagaagt gcagtgctag cacaaatgcc cagcaaattt   4320
accatatgcg ctaatgtgtc cttggatgaa agaagcaaac tagcatatga tgtaaccaca   4380
ccctgtgaaa tcaaggcatg tagtctaaca tgcctaaaat caaaaatat gttgactaca   4440
gttaaagatc tcactatgaa gacactcaac cctacacatg atattattgc tttatgtgaa   4500
tttgaaaaca tagtaacatc aaaaaagtc ataataccaa catacctaag atccatcagt   4560
gtcagaaata aagatctgaa cacacttgaa aatataacaa ccactgaatt caaaaatgct   4620
atcacaaatg caaaaatcat cccttactca ggattactat tagtcatcac agtgactgac   4680
aacaaaggag cattcaaata cataaagcca caaagtcaat tcatagtaga tcttggagct   4740
tacctagaaa agaaagtat atattatgtt accacaaatt ggaagcacac agctacacga   4800
tttgcaatca acccatggaa agattaacct ttttcctcta catcagtgtg ttaattcata   4860
caaactttct acctacattc ttcacttcac catcacaatc acaaacactc tgtggttcaa   4920
ccaatcaaac aaaacttatc tgaagtccca gatcatccca agtcattgtt tatcagatct   4980
agtactcaaa taagttaata aaaaatatac acatggacgt ccatgggca aatgcaaaca   5040
tgtcgaaaaa caaagaccaa cgtaccgcga agacgttaga acgtacctgg gatactcaa   5100
atcatttact attcatatcg tcgtgcctat ataagctaaa tcttaaatcg gtagcacaaa   5160
taacactatc catactggcg ataataatct cgacttcgct tataatagca gcgatcatat   5220
ttatagcctc ggcgaaccat aaagtcacgc caacgactgc gatcatacaa gatgcgacat   5280
cgcagataaa gaatacaacg ccaacgtacc taacccaaaa tcctcaactt ggtatctcgc   5340
cctcgaatcc gtctgaaata acatcgcaaa tcacgaccat actagcgtca acgacaccgg   5400
gagtaaagtc gaccctacaa tccacgcacg taaagacgaa aaacacgaca acgactcaaa   5460
cgcaaccctc gaagcgacc acgaaacaac gccaaaataa accccggaa aaccgaata   5520
atgattttca ctttgaagta ttcaattttg taccctgtag catatgtagc aataatccaa   5580
cgtgctggc gatctgtaaa agaataccga acaaaaacc gggaaaaaaa accacgacca   5640
aacccacgaa aaaccaacg ctcaaaacaa cgaaaaaaga tcccaaaccg caaaccacga   5700
aatcaaaaga agtacccacg accaaaccca cggaagagcc gaccataaac acgaccaaaa   5760
cgaacataat aactacgcta ctcacgtcca ataccacggg aaatccggaa ctcacgagtc   5820
```

```
aaatggaaac gtttcactcg acttcgtccg aaggtaatcc atcgccttcg caagtctcga   5880
caacgtccga atacccgtca caaccgtcat cgccaccgaa cacgccacgt cagtagttac   5940
ttaaaaacat attatcacaa aaggccttga ccaaccgcgg agaatcaaaa taaactctgg   6000
ggcaaataac aatggagttg ccaatcctca aagcaaatgc aattaccaca atcctcgctg   6060
cagtcacatt ttgctttgct tctagtcaaa acatcactga agaattttat caatcaacat   6120
gcagtgcagt tagcaaaggc tatcttagtg ctctaagaac tggttggtat actagtgtta   6180
taactataga attaagtaat atcaagaaaa ataagtgtaa tggaacagat gctaaggtaa   6240
aattgatgaa acaagaatta gataaatata aaaatgctgt aacagaattg cagttgctca   6300
tgcaaagcac accagcagca aacaatcgag ccagaagaga actaccaagg tttatgaatt   6360
atacactcaa caataccaaa aaaaccaatg taacattaag caagaaaagg aaaagaagat   6420
ttcttggttt tttgttaggt gttggatctg caatcgccag tggcattgct gtatctaagg   6480
tcctgcactt agaaggagaa gtgaacaaga tcaaagtgc tctactatcc acaaacaagg   6540
```

```
aaaattttcc gagagtgata aatcaagaag agtattagag tattatttaa gagataacaa   10620
attcaatgaa tgtgatttat acaactgtgt agttaatcaa agttatctca acaaccctaa   10680
tcatgtggta tcattgacag gcaaagaaag agaactcagt gtaggtagaa tgtttgcaat   10740
gcaaccggga atgttcagac aggttcaaat attggcagag aaaatgatag ctgaaaacat   10800
tttacaattc tttcctgaaa gtcttacaag atatggtgat ctagaactac aaaaaatatt   10860
agaattgaaa gcaggaataa gtaacaaatc aaatcgctac aatgataatt acaacaatta   10920
cattagtaag tgctctatca tcacagatct cagcaaattc aatcaagcat ttcgatatga   10980
aacgtcatgt atttgtagtg atgtgctgga tgaactgcat ggtgtacaat ctctattttc   11040
ctggttacat ttaactattc ctcatgtcac aataatatgc acatataggc atgcacccct   11100
ctatatagga gatcatattg tagatcttaa caatgtagat gaacaaagtg gattatatag   11160
atatcacatg ggtggcatcg aagggtggtg tcaaaaactg tggaccatag aagctatatc   11220
actattggat ctaatatctc tcaaagggaa attctcaatt actgctttaa ttaatggtga   11280
caatcaatca atagatataa gcaaaccaat cagactcatg gaaggtcaaa ctcatgctca   11340
agcagattat ttgctagcat taaatagcct taaattactg tataaagagt atgcaggcat   11400
aggccacaaa ttaaaaggaa ctgagactta tatatcacga gatatgcaat ttatgagtaa   11460
aacaattcaa cataacggtg tatattaccc agctagtata aagaaagtcc taagagtggg   11520
accgtggata aacactatac ttgatgattt caaagtgagt ctagaatcta taggtagttt   11580
gacacaagaa ttagaatata gaggtgaaag tctattatgc agtttaatat ttagaaatgt   11640
atggttatat aatcagattg ctctacaatt aaaaaatcat gcattatgta acaataaact   11700
atatttggac atattaaagg ttctgaaaca cttaaaaacc tttttaatc ttgataatat   11760
tgatacagca ttaacattgt atatgaattt acccatgtta tttggtggtg gtgatcccaa   11820
cttgttatat cgaagtttct atagaagaac tcctgacttc ctcacagagg ctatagttca   11880
ctctgtgttc atacttagtt attatacaaa ccatgactta aaagataaac ttcaagatct   11940
gtcagatgat agattgaata agtcttaac atgcataatc acgtttgaca aaaaccctaa   12000
tgctgaattc gtaacattga tgagagatcc tcaagcttta gggtctgaga gacaagctaa   12060
aattactagc gaaatcaata gactggcagt tacagaggtt ttgagtacag ctccaaacaa   12120
aatattctcc aaaagtgcac aacattatac tactacagag atagatctaa atgatattat   12180
gcaaaatata gaacctacat atcctcatgg gctaagagtt gtttatgaaa gtttaccctt   12240
ttataaagca gagaaaatag taaatcttat atcaggtaca aaatctataa ctaacatact   12300
ggaaaaaact tctgccatag acttaacaga tattgataga gccactgaga tgatgaggaa   12360
aaacataact ttgcttataa ggatacttcc attggattgt aacagagata aagagagat   12420
attgagtatg gaaaacctaa gtattactga attaagcaaa tatgttaggg aaagatcttg   12480
gtctttatcc aatatagttg gtgttacatc acccagtatc atgtatacaa tggacatcaa   12540
atactacaca agcactatat ctagtggcat aattatagag aaatataatg ttaacagttt   12600
aacacgtggt gagagaggac ccactaaacc atgggttggt tcatctacac aagagaaaaa   12660
aacaatgcca gttataata gacaagtctt aaccaaaaaa cagagagatc aaatagatct   12720
attagcaaaa ttggattggg tgtatgcatc tatagataac aaggatgaat tcatggaaga   12780
actcagcata ggaaccctg ggttaacata tgaaaaggcc aagaaattat ttccacaata   12840
tttaagtgtc aattatttgc atcgccttac agtcagtagt agaccatgtg aattccctgc   12900
atcaatacca gcttatagaa caacaaatta tcactttgac actagcccta ttaatcgcat   12960
attaacagaa aagtatggtg atgaagatat tgacatagta ttccaaaact gtataagctt   13020
tggccttagt ttaatgtcag tagtagaaca atttactaat gtatgtccta acagaattat   13080
tctcataccc aagcttaatg agatacattt gatgaaacct cccatattca caggtgatgt   13140
tgatattcac aagttaaaac aagtgataca aaaacagcat atgtttttac cagacaaaat   13200
aagtttgact caatatgtgg aattattctt aagtaataaa acactcaaat ctggatctca   13260
tgttaattct aatttaatat tggcacataa aatatctgac tattttcata atacttacat   13320
tttaagtact attttagctg gacattggat tctgattata caacttatga aagattctaa   13380
aggtattttt gaaaaagatt gggaagaggg atatatacct gatcatatgt ttattaattt   13440
gaaagttttc ttcaatgctt ataagaccta tctcttgtgt tttcataaag gttatggcaa   13500
agcaaagctg gagtgtgata tgaacacttc agatcttcta tgtgtattgg aattaataga   13560
cagtagttat tggaagtcta tgtctaaggt atttttagaa caaaagtta tcaaatacat   13620
tcttagccaa gatgcaagtt tacatagagt aaaaggatgt catagcttca aattatggtt   13680
tcttaaacgt cttaatgtag cagaattcac agtttgccct tgggttgtta acatagatta   13740
tcatccaaca catatgaaag caatattaac ttatatagat cttgttagaa tgggattgat   13800
aaatatagat agaataacaa acactaaatt caagtgatgat tttatcttc   13860
taatctcttc tacattaatt ataacttctc agataatact catctattaa ctaaacatat   13920
aaggattgct aattctgaat tagaaaataa ttacaacaaa ttatatcatc ctacaccaga   13980
aaccctagag aatatactag ccaatccgat taaaagtaat gacaaaaaga cactgaatga   14040
ctattgtata ggtaaaaatg ttgactcaat aatgttacca ttgttatcta ataagaagct   14100
tattaaatcg tctgcaatga ttagaaccaa ttacagcaaa caagatttgt ataattatt   14160
ccctatggtt gtgattgata gaattataga tcattcaggc aatacagcca atccaacca   14220
acttacact actacttccc accaaatatc tttagtgcac aatagcacat cactttactg   14280
catgcttcct tggcatcata ttaatagatt caatttttgta tttagttcta caggttgtaa   14340
aattagtata gagtatattt taaagatct taaattaaa gatcccaatt gtatgcatt   14400
cataggtgaa ggagcaggga atttattatt gcgtacagta gtggaacttc atcctgacat   14460
aagatatatt tacagaagtc tgaaagattg caatgatcat agtttaccta ttgagttttt   14520
aaggctgtac aatggacata tcaacattga ttatggtgaa aatttgacca ttcctgctac   14580
agatgcaacc aacaacattc attggtctta tttacatata aagtttgctg aacctatcag   14640
tctttttgtc tgtgatgccg aattgtctgt aacagtcaac aggtggagtaa ttataatgag   14700
atggagcaag catgtaagaa agtgcaagta ctgttcctca gttaataaat gtatgttaat   14760
agtaaaatat catgctcaag atgatattga tttcaaatta gacaatataa ctatattaaa   14820
aacttatgta tgcttaggca gtaagttaaa gggatcggag gtttacttag tccttacaat   14880
aggtcctgcg aatatattcc cagtatttaa tgtagtacaa aatgctaaat tgatactatc   14940
aagaaccaaa aatttcatca tgcctaagaa agctgataaa gagtctattg atgcaaatat   15000
taaaagtttg ataccctttc tttgttaccc tataacaaaa aaggaatta atactgcatt   15060
gtcaaaacta aagagtgttg ttagtggaga tatactatca tattcatag ctggacgtaa   15120
tgaagttttc agcaataaac ttataaatca taagcatatg aacatcttaa aatggttcaa   15180
tcatgtttta aatttcagat caacagaact aaactataac catttatata tggtagaatc   15240
tacatatcct tacctaagtg aattgttaaa cagcttgaca accaatgaac ttaaaaaact   15300
```

```
gattaaaatc acaggtagtc tgttatacaa ctttcataat gaataatgaa taaagatctt 15360
ataataaaaa ttcccatagc tatacactaa cactgtattc aatttatagtt attaaaaatt 15420
aaaaatcgta cgatttttta aataactttt agtgaactaa tcctaaagtt atcattttaa 15480
tcttggagga ataaatttaa accctaatct aattggttta tatgtgtatt aactaaatta 15540
cgagatatta gttttttgaca cttttttttct cgt                              15573

SEQ ID NO: 3           moltype = DNA   length = 15573
FEATURE                Location/Qualifiers
source                 1..15573
                       mol_type = genomic DNA
                       organism = respiratory syncytial virus
SEQUENCE: 3
acgcgaaaaa atgcgtacaa caaacttgca taaaccaaaa aaatgggggca aataagaatt    60
tgataagtac cacttaaatt taactcccctt gcttagcgat ggtgagcgag ctgattaagg   120
agaacatgca catgaagctg tacatggagg gcaccgtgaa caaccaccac ttcaagtgca   180
catccgaggg cgaaggcaag ccctacgagg gcacccagac catgagaatc aaggcggtcg   240
agggcggccc tctccccttc gccttcgaca tcctggctac cagcttcatg tacggcagca   300
aaaccttcat caaccacacc cagggcatcc ccgacttctt taagcagtcc ttcccccgagg  360
gcttcacatg ggagagagtc accacatacg aagacggggg cgtgctgacc gctacccagg   420
acaccagcct ccaggacggc tgcctcatct acaacgtcaa gatcagaggg gtgaacttcc   480
catccaacgg ccctgtgatg cagaagaaaa cactcggctg ggaggcctcc accgagaccc   540
tgtaccccgc tgacggcggc ctggaaggca gagccgacat ggccctgaag ctcgtgggcg   600
ggggccacct gatctgcaac ttgaagacca catacagatc caagaaaccc gctaagaacc   660
tcaagatgcc cggcgtctac tatgtggaca aagactgga aagaatcaag gaggccgaca   720
aagagaccta cgtcgagcag cacgaggtgg ctgtggccag atactgcgac ctccctgcca   780
aactggggca cagatgagta ttcaattata gttattaaaa acttaacaga agacaaaaat   840
ggggcaaata agaatttgat aagtaccact taaatttaac tccccttgctt agcgatgggt   900
tcgaattcgc tatcgatgat aaaagtacgt ctacaaaatc tatttgataa tgatgaagta   960
gcgctactaa aaataacgtg ttatacggat aaactaatac atctaacgaa tgcgctagcg  1020
aaagcggtaa tacatacgat aaaactaaat ggtatagtat ttgtacatgt aataacgtcg  1080
tcggatatat gtccgaataa taatatagta gtaaaatcga attttacgac gatgccggta  1140
ctacaaaatg tgtggtatat atgggaaatg atggaactaa cgcattgttc gcaaccgaat  1200
ggtctactag atgataattg tgaaataaaa ttttcgaaaa aactatcgga ttcgacgatg  1260
acgaattata tgaatcaact atcggaacta ctaggttttg atctaaatcc gtaaattata  1320
attaatatca actagcaaat caatgtcact aacaccatta gttaatataa aacttaacag  1380
aagacaaaaa tggggcaaat aaatcaattc agccaaccca accatggata cgacgcataa  1440
tgataatacg ccgcaacgtc taatgataac ggatatgcgt ccgctatcgc tagaaacgat  1500
aataacgtcg ctaacgcgtg atataataac gcataaattt atatatctaa taaatcatga  1560
atgtatagta cgtaaactag atgaacgtca agcgacgttt acgtttctag taaattatga  1620
aatgaaacta ctacataaag taggttcgac gaaatataaa aaatatacgg aatataatac  1680
gaaatatggt acgtttccga tgccgatatt tataaatcat gatggttttc tagaatgtat  1740
aggtataaaa ccgacgaaac atacgccgat aatatataaa tatgatctaa atccgtaaat  1800
ttcaacacaa tattcacaca atctaaaaca acaactactat cgataactat actccatagt  1860
ccagatggag cctgaaaatt atagtaattt aaaattaagg agagatataa gatagaagat  1920
ggggcaaata caaagatggc tcttagcaaa gtcaagttga atgatacact caacaaagat  1980
caacttctgt catccagcaa atacaccatc caacggagca caggagatag tattgatact  2040
cctaattatg atgtgcagaa acacatcaat aagttatgtg gcatgttatt aatcacagaa  2100
gatgctaatc ataaattcac tgggttaata ggtatgttat atgcgatgtc taggttagga  2160
agagaagaca cctataaaaat actcagagat gcgggatatc atgtaaaagc aaatggagta  2220
gatgtaacaa cacatcgtca agacattaat ggaaagaaaa tgaaatttga agtgttaaca  2280
ttggcaagct taacaactga aattcaaatc aacattgaga tagaatctag aaaatcctac  2340
aaaaaaatgc taaaagaaat gggagaggta gctccagaat acaggcatga ctctcctgat  2400
tgtgggatga taatattatg tatagcagca ttagtaataa ctaaattagc agcaggggac  2460
agatctggtc ttacagccgt gattaggaga gctaataatg tcctaaaaaa tgaaatgaaa  2520
cgttacaaag gcttactacc caaggacata gccaacagct tctatgaagt gtttgaaaaa  2580
catccccact ttatgatgct ttttgttcat tttggtatag cacaatcctc taccagaggt  2640
ggcagtagag ttgaagggat ttttgcagga ttgtttatga atgccatggt gcagggcaa   2700
gtgatgttac ggtggggagt cttagcaaaa tcagttaaaa atattatgtt aggacatgct  2760
agtgtgcaag cagaaatgga acaagttgtt gaggtttatg aatatgccca aaaattgggt  2820
ggtgaagcag gattctacca tatattgaac aacccaaaag catcattatt atctttgact  2880
caatttcctc acttctccag tgtagtatta ggcaatgctg ctggcctagg cataatggga  2940
gagtacagag gtacaccgag gaatcaagat ctatatgatg cagcaaaggc atatgctgaa  3000
caactcaaag aaaatggtgt gattaactac agtgtactag acttgacagc agaagaacta  3060
gaggctatca aacatcagct taatccaaaa gataatgatg agtaataaa                3120
aaatggggca aataaatcat catggaaaag tttgctcctg aattccatgg agaagatgca  3180
aacaacaggg ctactaaatt cctagaatca ataagggca aattcacatc acccaaagat  3240
cccaagaaaa aagatagtat catatctgtc aactcaatag atatagaagt aaccaaagaa  3300
agccctataa catcaaattc aactattatc aacccaacaa atgagacaga tgatactgca  3360
gggaacaagc ccaattatca aagaaaaccct ctagtaagtt tcaaagaaga ccctacacca  3420
agtgataatc cctttttctaa actatacaaa gaaaccatag aaacatttga taacaatgaa  3480
gaagaatcca gctattcata cgaagaaata aatgatcaga caaacgataa tataacagca  3540
agattagata ggattgatga aaattaagt gaaaactag gaatgcttca cacattagta  3600
gtggcaagtg caggacctac atctgctcgg gatggtataa gagatgccat gattggttta  3660
agagaaagaa tgatagaaaa aatcagaact gaaccaatag cagaattagaa                3720
gctatggcaa gactcaggaa tgaggaaagt gaaagatgg caaaagacac atcagatgaa  3780
gtgtctctca atccaacatc agagaaattg aacaacctat ggaagggaa tgatagtgac  3840
aatgatctat cacttgaaga tttctgatta gttaccactc ttcacatcaa cacacaatac  3900
caacagaaga ccaacaaact aaccaaccca atcatccaac aaacatcca tccgccaatc  3960
agccaaacag ccaacaaaac aaccagccaa tccaaaacta accacccgga aaaaatctat  4020
```

```
aatatagtta caaaaaaagg aaagggtggg gcaaatatgg aaacatacgt gaacaagctt   4080
cacgaaggct ccacatacac agctgctgtt caatacaatg tcttagaaaa agacgatgac   4140
cctgcatcac ttacaatatg ggtgcccatg ttccaatcat ctatgccagc agatttactt   4200
ataaagaac tagctaatgt caacatacta gtgaaacaaa tatccacacc caagggacct    4260
tcactaagag tcatgataaa ctcaagaagt gcagtgctag cacaaatgcc cagcaaattt   4320
accatatgcg ctaatgtgtc cttggatgaa agaagcaaac tagcatatga tgtaaccaca   4380
ccctgtgaaa tcaaggcatg tagtctaaca tgcctaaaat caaaaatat gttgactaca    4440
gttaaagatc tcactatgaa gacactcaac cctacacatg atattattgc tttatgtgaa   4500
tttgaaacca tagtaacatc aaaaaaagtc ataataccaa catacctaag atccatcagt   4560
gtcagaaata aagatctgaa cacacttgaa aatataacaa ccactgaatt caaaaatgct   4620
atcacaaatg caaaaatcat cccttactca ggattactat tagtcatcac agtgactgac   4680
aacaaaggag cattcaaata cataaagcca caaagtcaat tcatagtaga tcttggagct   4740
tacctagaaa aagaaagtat atattatgtt accacaaatt ggaagcacac agctacacga   4800
tttgcaatca aacccatgga agattaacct ttttcctcta catcagtgtg ttaattcata   4860
caaactttct acctacattc ttcacttcac catcacaatc acaaacactc tgtggttcaa   4920
ccaatcaaac aaaacttatc tgaagtccca gatcatccca agtcattgtt tatcagatct   4980
agtactcaaa taagttaata aaaaatatac acatggacgt ccatgggca aatgcaaaca    5040
tgtcgaaaaa taaagaccaa cgtacggcga agacgctaga acgtacctgg gatacgctaa   5100
atcatttact atttatatcg tcgtgcctat ataaactaaa tcttaaatcg gtagcgcaaa   5160
taacactatc gatactggcg ataataatat cgacttcgct aataatagca gcgataatat   5220
ttatagcctc ggcgaatcat aaagtcacgc cgacgactgc gataatacaa gatgcgacat   5280
cgcaaataaa gaatacgacg ccaacgtatc taacccaaaa tccgcaactt ggtatatcgc   5340
cctcgaatcc gtcggaaata acatcgcaaa taacgaccat actagcgtcg acgacaccgg   5400
gtgtaaagtc gacgctacaa tccacgacgg taaagacgaa aaatacgaca acgacgcaaa   5460
cgcaaccgtc gaaaccgacc acgaaacaac gtcaaaataa accaccgtcg aaaccgaata   5520
atgattttca cttttgaagta tttaattttg taccctgttc gatatgtagc aataatccga   5580
cgtgctgggc gatatgtaaa agaataccga ataaaaaacc gggaaaaaaa acgacgacca   5640
aaccgacgaa aaaccaacg ctaaaaacaa cgaaaaaaga tccgaaaccg caaaccacga    5700
aatcgaaaga agtacccacg acgaaaccca cggaagaacc gaccataaat acgaccaaaa   5760
cgaatataat aactacgcta ctaacgtcca atacgacggg aaatccggaa ctaacgagtc   5820
aaatggaaac gtttcattcg acttcgtcgg aaggtaatcc atcgccgtcg caagtctcga   5880
cgacttccga atatccgtca caaccgtcgt cgccaccgaa tacgccacgt caatagttac   5940
ttaaaaacat attatcacaa aaggccttga ccaaccgcgg agaatcaaaa taaactctgg   6000
ggcaaataac aatggagttg ccaatcctca aagcaaatgc aattaccaca atcctcgctg   6060
cagtcacatt ttgctttgct tctagtcaaa acatcactga agaattttat caatcaacat   6120
gcagtgcagt tagcaaaggc tatcttagtg ctctcaagaac tggttggtat actagtgtta   6180
taactataga attaagtaat atcaagaaaa ataagtgtaa tggaacagat gctaaggtaa   6240
aattgatgaa acaagaatta gataaatata aaaatgctgt aacagaattg cagttgctca   6300
tgcaaagcac accagcagca aacaatcgag ccagaaggaa actccaagg tttatgaatt    6360
atacactcaa caataccaaa aaaaccaatg taacattaag caagaaaagg aaaagaagat   6420
ttcttggttt tttgttaggt gttggatctg caatcgccag tggcattgct gtatctaagg   6480
tcctgcactt agaaggagaa gtgaacaaga tcaaagtgc tctactatcc acaaacaagg    6540
ccgtagtcag cttatcaaat ggagttagtg tcttaaccag cagagtgtta gacctcaaaa   6600
actatataga taaacaattg ttacctattg tgaataagca aagctgcaga atatcaaata   6660
tagaaactgt gatagagttc caacaaaaga acaacagact actagagatt accagggaat   6720
ttagtgttaa tgcaggtgta actacacctg taagcactta catgttaact aatagtgaat   6780
tattgtcatt aatcaatgat atgcctataa caaatgatca gaaaaagtta atgtccaaca   6840
atgttcaaat agttagacag caaagttact ctatcatgtc cataataaaa gaggaagtct   6900
tagcatatgt agtacaatta ccactatatg gtgtgataga tacacttgtt tggaaattac   6960
acacatcccc tctatgtaca accaacacaa agaagggtc aaacatcgtt ttaacaagaa    7020
ctgacagagg atggtactgt gacaatgcag gatcagtatc tttcttccca caagctgtaa   7080
aatgtaaagt tcaatcgaat cgagtatttt gtgacacaat gtacagttta acattaccaa   7140
gtgaagtaaa tctctgcaat gttgacatat tcaatcccaa atatgattgt aaaattatga   7200
cttcaaaaac agatgtaagc agctccgtta tcacatctct aggagccatt gtgtcatgct   7260
atggcaaaac taaatgtaca gcatccaata aaaatcgtgg aatcataaag acattttcta   7320
acgggtgtga ttatgtatca aataaagggg tggacactgt gtctgtaggt aacacattat   7380
attatgtaaa taagcaagaa ggcaaaagtc tctatgtaaa aggtgaacca ataataaatt   7440
tctatgaccc attagtattc ccctctgatg aatttgatgc atcaatatct caagtcaatg   7500
agaagattaa ccagagttta gcatttattc gtaaatccga tgaattatta cataatgtaa   7560
atgctggtaa atcaaccaca aatatcatga taactactat aattatagtg attatagtaa   7620
tattgttatc attaattgct gttggactgc tcctatactg taaggccaga agcacaccag   7680
tcacactaag caaggatcaa ctgagtggta taaataatat tgcatttagt aactgaataa   7740
aaatagcacc taatcatgtt cttacaatgg tttactatct gctcatagac aacccatcat   7800
tcattggatt ttcttaaaat ctgaacttca tcgaaactct tatctataaa ccatctcact   7860
tacactattt aagtagattc ctagtttata gttatataaa acacaattga atgccagtcg   7920
accttaccat ctgtaaaaat gaaactgggg caaatatgt cacgaaggaa tccttgcaaa    7980
tttgaaattc gaggtcattg cttaaatggt aagaggtgtc attttagtca aattattttt   8040
gaatggccac cccatgcact gcttgtaaga caaaactta tgttaaacag aatacttaag   8100
tctatggata aagtataga taccttatcca gaaataagtg gagctgcaga gttggacaga   8160
acagaagagt atgctcttgg tgtagttgga gtgctagaga gttatatagg atcaataaac   8220
aatataacta aacaatcagc atgtgttgcc atgagcaaac tcctcactga actcaatagt   8280
gatgatatca aaaagctgag ggacaatgaa gagctaaatt cacccaagat aagagtgtac   8340
aatactgtca tatcatatat tgaaagcaac aggaaaaaca ataaacaaac tatccatctg   8400
ttaaaaagat tgccagcaga cgtattgaag aaaaccatca ggatatccat   8460
aagagcataa ccatcaacaa cccaaaagaa tcaactgtta gtgatacaaa tgaccatgcc   8520
aaaaataatg atactacctg acaaatatcc ttgtagtata acttcctac taataacaag   8580
tagatgtaga gttactatgt ataatcaaaa gaacacacta tatttcaatc aaaacaaccc   8640
aaataaccat atgtactcac cgaatcaaac attcaatgaa atccattgga cctctcaaga   8700
attgattgac acaattcaaa attttctaca acatctaggt attattgagg atatatatac   8760
```

```
aatatatata ttagtgtcat aacactcaat tctaacactc accacatcgt tacattatta  8820
attcaaacaa ttcaagttgt gggacaaaat ggatcccatt attaatgaaa attctgctaa  8880
tgtttatcta accgatagtt atttaaaagg tgttatctct ttctcagagt gtaatgcttt  8940
aggaagttac atattcaatg gtccttatct caaaaatgat tataccaact taattagtag  9000
acaaaatcca ttaatagaac acatgaatct aaagaaacta aatataacac agtccttaat  9060
atctaagtat cataaaggtg aaataaaatt agaagaacct acttattttc agtcattact  9120
tatgacatac aagagtatga cctcgtcaga acagattgct accactaatt tacttaaaaa  9180
gataataaga agagctatag aaataagtga tgtcaaagtc tatgctatat tgaataaaact  9240
agggcttaaa gaaaaggaca agattaaatc caacaatgga caagatgaag acaactcagt  9300
tattacgacc ataatcaaag atgatatact ttcagctgtt aaagataatc aatctcatct  9360
taaagcagac aaaaatcact ctacaaaaca aaaagacaca atcaaaacaa cactcttgaa  9420
gaaattgatg tgttcaatgc aacatcctcc atcatggtta atacattggt ttaacttata  9480
cacaaaatta aacaacatat taacacagta tcgatcaaat gaggtaaaaa accatgggtt  9540
tacattgata gataatcaaa ctcttagtgg atttcaattt attttgaacc aatatggttg  9600
tatagtttat cataaggaac tcaaaagaat tactgtgaca acctataatc aattcttgac  9660
atggaaagat attagcctta gtagattaaa tgtttgttta attacatgga ttagtaactg  9720
cttgaacaca ttaaataaaa gcttaggctt aagatgcgga ttcaataatg ttatcttgac  9780
acaactattc ctttatggag attgtatact aaagctattt cacaatgagg ggttctacat  9840
aataaaagag gtagagggat ttattatgtc tctaatttta aatataacag aagaagatca  9900
attcagaaaa cgattttata atagtatgct caacaacatc acagatgctg ctaataaagc  9960
tcagaaaaat ctgctatcaa gagtatgtca tacattatta gataagacag tgtccgataa 10020
tataataaat ggcagatgga taattctatt aagtaagttc cttaaattaa ttaagcttgc 10080
aggtgacaat aaccttaaca atctgagtga actatatttt ttgttcagaa tatttggaca 10140
cccaatggta gatgaaagac aagccatgga tgctgttaaa attaattgca atgagaccaa 10200
attttacttg ttaagcagtc tgagtatgtt aagaggtgcc tttatatata gaattataaa 10260
agggtttgta aataattaca acagatggcc tactttaaga aatgctattg ttttaccctt 10320
aagatggtta acttactata aactaaacac ttatccttct ttgttggaac ttacagaaag 10380
agatttgatt gtgttatcag gactacgttt ctatcgtgag tttcggttgc ctaaaaaagt 10440
ggatcttgaa atgattataa atgataaagc tatatcacct cctaaaaatt tgatatggac 10500
tagtttccct agaaattaca tgccatcaca catacaaaac tatatagaac atgaaaaatt 10560
aaaattttcc gagagtgata aatcaagaag agtattagag tattatttaa gagataacaa 10620
attcaatgaa tgtgatttat acaactgtgt agttaatcaa agttatctca acaaccctaa 10680
tcatgtggta tcattgacag gcaaagaaag agaactcagt gtaggtagaa tgtttgcaat 10740
gcaaccggga atgttcagac aggttcaaat attggcaggg aaaatgatag ctgaaaacat 10800
tttacaattc tttcctgaaa gtcttacaag atatggtgat ctagaactac aaaaaaatatt 10860
agaattgaaa gcaggaataa gtaacaaatc aaatcgctac aatgataatt acaacaatta 10920
cattagtaag tgctctatca tcacagatct cagcaaattc aatcaagcat tcgatgatga 10980
aacgtcatgt atttgtagtg atgtgctgga tgaactgcat ggtgtacaat ctctattttc 11040
ctggttacat ttaactattc ctcatgtcac aataatatgc acatatagc atgcaccccc 11100
ctatatagga gatcatattg tagatcttaa caatgtagat gaacaaagtg gattatatag 11160
atatcacatg ggtggcatcg aagggtggtg tcaaaaactg tggaccatag aagctatatc 11220
actattggat ctaatatctc tcaaagggaa attctcaatt actgctttaa ttaatggtga 11280
caatcaatca atagatataa gcaaaccaat cagactcatg gaaggtcaaa ctcatgctca 11340
agcagattat ttgctagcat taaatagcct taaattactg tataaagagt atgcaggcat 11400
aggccacaaa ttaaaaggaa ctgagactta tatatcacga gatatgcaat ttatgagtaa 11460
aacaattcaa cataacggtg tatattaccc agctagtata aagaaagtcc taagagtggg 11520
accgtggata aacactatac ttgatgattt caaagtgagt ctagaatcta taggtagttt 11580
gacacaagaa ttagaatata gaggtgaaag tctattatgc agtttaatat ttagaaatgt 11640
atggttatat aatcagattg ctctacaatt aaaaaaatcat gcattatgta acaataaact 11700
atatttggac atattaaagg ttctgaaaca cttaaaaacc tttttttaatc ttgataatat 11760
tgatacagca ttaacattgt atatgaattt acccatgtta tttggtggtg gtgatcccaa 11820
cttgttatat cgaagtttct atagaagaac tcctgacttc ctcacagagg ctatagttca 11880
ctctgtgttc atacttagtt attatacaaa ccatgactta aaagataaac ttcaagatct 11940
gtcagatgat agattgaata agttcttaac atgcataatc acgttgaca aaaaccctaa 12000
tgctgaattc gtaaccattga tgagagatcc tcaagcttta gggtctgaga gacaagctaa 12060
aattactagc gaaatcaata gactggcagt tacagaggtt ttgagtacag ctccaaacaa 12120
aatattctcc aaaagtgcac aacattatac tactacagag atagatctaa atgatattat 12180
gcaaaatata gaacctacat atcctcatgg gctaagagtt gtttatgaaa gtttacccct 12240
ttataaagca gagaaaatag taaatcttat atcaggtaca aaatctataa ctaacatact 12300
ggaaaaaact tctgccatag acttaacaga tattgataga gccactgaga tgatgaggaa 12360
aaacataact ttgctttataa ggatacttcc attggattgt aacagagata aaagagagat 12420
attgagtatg gaaaacctaa gtattactga attaagcaaa tatgttaggg aaagatcttg 12480
gtctttatcc aatatagttg gtgttacatc acccagtatc atgtatacaa tggacatcaa 12540
atatactaca agcactatat ctagtggcat aattataga aaatataatg ttaacagttt 12600
aacacgtggt gagagaggac ccactaaacc atgggttggt tcatctacac aagagaaaaa 12660
aacaatgcca gttataaata gacaagtctt aaccaaaaaa cagagagatc aaatagatct 12720
attagcaaaa ttggattggg tgtatgcatc tatagataac aaggatgaat tcatggaaga 12780
actcagcata ggaaccccttg ggttaacata tgaaaaggcc aagaaaattat ttccacaata 12840
tttaagtgtc aattatttgc atcgccttac agtcagtagt agaccatgtg aattccctgc 12900
atcaatacca gcttatagaa caacaaatta tcactttgac actagcccta ttaatcgcat 12960
attaacagaa aagtatggtg atgaagatat tgacatagta ttccaaaact gtataagctt 13020
tggccttagt ttaatgtcag tagtagaaca atttactaat gtatgtccta acagaattat 13080
tctcatacct aagcttaatg agatacattt gatgaaacct cccatattca caggtgatgt 13140
tgatattcac aagttaaaac aagtgataca aaaacagcat atgttttac cagacaaaat 13200
aagtttgact caatatgtgg aattattctt aagtaataaa acactcaaat ctggatctca 13260
tgttaattct aatttaatat tggcacataa aatatctgac tattttcata atacttacat 13320
tttaagtact aatttagctg gacattggat tctgattata caacttatga aagattctaa 13380
aggtattttt gaaaaagatt ggggagaggg atatataact gatcatatgt ttattaattt 13440
gaaagttttc ttcaatgctt ataagaccta tctcttgtgt tttcataaag gttatggcaa 13500
```

```
agcaaagctg gagtgtgata tgaacacttc agatcttcta tgtgtattgg aattaataga  13560
cagtagttat tggaagtcta tgtctaaggt attttagaa caaaagtta tcaaatacat  13620
tcttagccaa gatgcaagtt tacatagagt aaaaggatgt catagcttca aattatggtt  13680
tcttaaacgt cttaatgtag cagaattcac agtttgccct tgggttgtta acatagatta  13740
tcatccaaca catatgaaag caatattaac ttatatagat cttgttagaa tgggattgat  13800
aaatatagat agaatacaca ttaaaaataa acacaaattc aatgatgaat tttatacttc  13860
taatctcttc tacattaatt ataacttctc agataatact catctattaa ctaaacatat  13920
aaggattgct aattctgaat tagaaaataa ttacaacaaa ttatatcatc ctacaccaga  13980
aaccctagag aatatactag ccaatccgat taaaagtaat gacaaaaaga cactgaatga  14040
ctattgtata ggtaaaaatg ttgactcaat aatgttacca ttgttatcta ataagaagct  14100
tattaaatcg tctgcaatga ttagaaccaa ttacagcaaa caagatttgt ataatttatt  14160
ccctatggtt gtgattgata gaattataga tcattcaggc aatacagcca aatccaacca  14220
actttacact actacttccc accaaatatc tttagtgcaa aatagcacat cactttactg  14280
catgcttcct tggcatcata ttaatagatt caatttgta tttagttcta caggttgtaa  14340
aattagtata gagtatattt taaaagatct taaaattaaa gatcccaatt gtatagcatt  14400
cataggtgaa ggagcaggga atttattatt gcgtacagta gtggaacttc atcctgacat  14460
aagatatatt tacagaagtc tgaaagattg caatgatcat agtttaccta ttgagttttt  14520
aaggctgtac aatggacata tcaacattga ttatggtgaa aatttgacca ttcctgctac  14580
agatgcaacc aacaacattc attggtctta tttacatata aagtttgctg aacctatcag  14640
tcttttgtc tgtgatgccg aattgtctgt aacagtcaac tggagtaaaa ttataataga  14700
atggagcaag catgtaagaa agtgcaagta ctgttcctca gttaataaat gtatgttaat  14760
agtaaaatat catgctcaag atgatattga tttcaaatta gacaatataa ctatattaaa  14820
aacttatgta tgcttaggca gtaagttaaa gggatcggag gtttacttag tccttacaat  14880
aggtcctgcg aatatattcc cagtatttaa tgtagtacaa aatgctaaat tgatactatc  14940
aagaaccaaa aatttcatca tgcctaagaa agctgataaa gagtctattg atgcaaatat  15000
taaaagtttg atacccttc ttttgttaccc tataacaaaa aaaggaatta atactgcatt  15060
gtcaaaacta aagagtgttg ttagtggaga tatactatca tattcctatag ctggacgtaa  15120
tgaagtttc agcaataaac ttataaatca taagcatatg aacatcttaa aatggttcaa  15180
tcatgtttta aatttcagat caacagaact aaactataac catttatata tggtagaatc  15240
tacatatcct tacctaagtg aattgttaaa cagcttgaca accaatgaac ttaaaaaact  15300
gattaaaatc acaggtagtc tgttatacaa ctttcataat gaataatgaa taaagatctt  15360
ataataaaaa ttcccatagc tatacactaa cactgtattc aattatagtt attaaaaatt  15420
aaaaatcgta cgatttttta aataacttttt agtgaactaa tcctaaagtt atcattttaa  15480
tcttggagga ataaatttaa accctaatct aattggttta tatgtgtatt aactaaatta  15540
cgagatatta gttttttgaca ctttttttct cgt                              15573
```

SEQ ID NO: 4        moltype = DNA  length = 15573
FEATURE               Location/Qualifiers
source                1..15573
                        mol_type = genomic DNA
                        organism = respiratory syncytial virus
SEQUENCE: 4

```
acgcgaaaaa atgcgtacaa caaacttgca taaaccaaaa aaatgggggca aataagaatt   60
tgataagtac cacttaaatt taactcccctt gcttagcgat ggtgagcgag ctgattaagg  120
agaacatgca catgaagctg tacatggagg gcaccgtgaa caaccaccac ttcaagtgca  180
catccgaggg cgaaggcaag ccctacgagg gcacccagac catgagaatc aaggcggtcg  240
agggcgccc tctcccttc gccttcgaca tcctggctac cagctcatg tacggcagca  300
aaaccttcat caaccacacc cagggcatcc ccgacttctt taagcagtcc ttccccgagg  360
gcttcacatg ggagagagtc accacatacg aagacggggg cgtgctgacc gctacccagg  420
acaccagcct ccaggacggc tgcctcatct acaacgtcaa gatcagaggg gtgaacttcc  480
catccaacgg ccctgtgatg cagaagaaaa cactcggctg ggaggcctcc accgagaccc  540
tgtaccccgc tgacggcggc ctggaaggca gagccgacat ggccctgaag ctcgtgggcg  600
ggggccacct gatctgcaac ttgaagacca catacagatc caagaaaccc gctaagaacc  660
tcaagatgcc cggcgtctac tatgtggaca agactggaa gaatcaag gaggccgaca  720
aagagaccta cgtcgagcag cacgagtggg ctgtgggcaa atactgcgac ctccctagca  780
aactggggca cagatgagta ttcaattata gttattaaaa acttaacaga agacaaaaat  840
ggggcaaata agaatttgat aagtaccact taaatttaac tccccttgctt agcgatgggt  900
tcgaattcgc tatcgatgat aaaagtacgt ctacaaaatc tatttgataa tgatgaagta  960
gcgctactaa aaataacgtg ttatacggat aaactaatac atctaacgaa tgcgctagcg 1020
aaagcggtaa tacatacgat aaaactaaat ggtatagtat ttgtacatgt aataacgtcg 1080
tcggatatat gtccgaataa taatatagta gtaaaatcga attttacgac gatgccggta 1140
ctacaaaatg gtggtatat atgggaaatg atggaactaa cgcattgttc gcaaccgaat 1200
ggtctactag atgataattg tgaaataaaa ttttcgaaaa aactatcgga ttcgacgatg 1260
acgaattata tgaatcaact atcggaacta ctaggttttg atctaaatcc gtaaattata 1320
attaatatca actagcaaat caatgtcact aacaccatta gttaatataa aacttaacag 1380
aagacaaaaa tggggcaaat aaatcaattc agccaaccca accatggata cgacgcataa 1440
tgataatacg ccgcaacgtc taatgataac ggatatgcgt ccgctatcgc tagaaacgat 1500
aatacgtcg ctaacgcgtg atataataac gcataaattt atatatctaa taaatcatga 1560
atgtatagta cgtaaactag atgaacgtca agcgacgttt acgtttctag taaattatga 1620
aatgaaacta ctacataaag taggttcgac gaaatataaa aaatatacgg aatataatac 1680
gaaatatggt acgtttccga tgccgatatt tataaatcat gatggttttc tagaatgtat 1740
aggtataaaa ccgacgaaac atacgccgat aatatataaa tatgatctaa atccgtaaat 1800
ttcaacacaa tattcacaca atctaaaaca acaactctat gcataactat actccatgt 1860
ccagatggag cctgaaaatt taagtaaattt aaaattaagg agagatataa gataagaat 1920
ggggcaaata caaagatggc tcttagcaaa gtcaagttga atgatacact caacaaagat 1980
caacttctgt catccagcaa ataccatc aacggagca caggagatag tattgatact 2040
cctaattatg atgtgcagaa acacatcaat aagttatgtg gcatgttatt aatcacagaa 2100
gatgctaatc ataaattcac tgggttaata ggtatggttat atgcgatgtc taggttagga 2160
agagaagaca ccataaaat actcagagat gcgggatatc atgtaaaagc aaatggagta 2220
```

```
gatgtaacaa cacatcgtca agacattaat ggaaaagaaa tgaaatttga agtgttaaca    2280
ttggcaagct taacaactga aattcaaatc aacattgaga tagaatctag aaaatcctac    2340
aaaaaaatgc taaagaaat gggagaggta gctccagaat acaggcatga ctctcctgat     2400
tgtgggatga taatattatg tatagcagca ttagtaataa ctaaattagc agcagggac     2460
agatctggtc ttacagccgt gattaggaga gctaataatg tcctaaaaaa tgaaatgaaa    2520
cgttacaaag gcttactacc caaggacata gccaacagct tctatgaagt gtttgaaaaa    2580
catccccact ttatagatgt tttttgttcat tttggtatag cacaatcttc taccagaggt   2640
ggcagtagag ttgaagggat ttttgcagga ttgtttatga atgcctatgg tgcagggcaa    2700
gtgatgttac ggtggggagt cttagcaaaa tcagttaaaa atattatgtt aggacatgct    2760
agtgtgcaag cagaaatgga acaagttgtt gaggtttatg aatatgccca aaaattgggt    2820
ggtgaagcag gattctacca tatattgaac aacccaaaag catcattatt atctttgact    2880
caatttcctc acttctccag tgtagtatta ggcaatgctg ctggcctagg cataatggga    2940
gagtacagag gtacaccgag gaatcaagat ctatatgatg cagcaaaggc atatgctgaa    3000
caactcaaag aaaatggtgt gattaactac agtgtactag acttgacagc agaagaacta    3060
gaggctatca aacatcagct taatccaaaa gataatgatg tagagctttg agttaataaa    3120
aaatggggca aataaatcat catggaaaag tttgctcctg aattccatgg agaagatgca    3180
aacaacaggg ctactaaatt cctagaatca ataaagggca aattcacatc acccaaagat    3240
cccaagaaaa aagatagtat catatctgtc aactcaatag atatagaagt aaccaaagaa    3300
agccctataa catcaaattc aactattatc aacccaacaa atgagacaga tgatactgca    3360
gggaacaagc ccaattatca agaaaaacct ctagtaagtt tcaaagaaga ccctacacca    3420
agtgataatc ccttttctaa actatacaaa gaaaccatag aaacatttga taacaatgaa    3480
gaagaatcca gctattcata cgaagaaata aatgatcaga aaacgataa tataacagca    3540
agattagata ggattgatga aaaattaagt gaaatactag aatgcttca cacattagta    3600
gtggcaagtg caggacctac atctgctcgg gatggtataa gagatgccat gattggttta    3660
agagaagaaa tgatagaaaa aatcagaact gaagcattaa tgaccaatga cagattagaa    3720
gctatggcaa gactcaggaa tgaggaaagt gaaaagatgg caaaagacac atcagatgaa    3780
gtgtctctca atccaacatc agagaaattg aacaacctat ggaagggaa tgatagtgac    3840
aatgatctat cacttgaaga tttctgatta gttaccactc ttcacatcaa cacacaatac    3900
caacagaaga ccaacaaact aaccaaccca atcatccaac aaacatcca tccgccaatc    3960
agccaaacag ccaacaaaac aaccagccaa tccaaaacta accacccgga aaaaatctat    4020
aatatagtta caaaaaagg aaagggtggg gcaaatatgg aaacatacgt gaacaagctt    4080
cacgaaggct ccacatacac agctgctgtt caatacaatg tcttagaaaa agacgatgac    4140
cctgcatcac ttacaatatg ggtgcccatg ttccaatcat ctatgccagc agatttactt    4200
ataaaagaac tagctaatgt caacatacta gtgaaacaaa tatccacacc caagggacct    4260
tcactaagag tcatgataaa ctcaagaagt gcagtgctag cacaaatgcc cagcaaattt    4320
accatatgcg ctaatgtgtc cttggatgaa agaagcaaac tagcatatga tgtaaccaca    4380
ccctgtgaaa tcaaggcatg tagtctaaca tgcctaaaat caaaaaatat gttgactaca    4440
gttaaagatc tcactatgaa gacactcaac cctcacacatg atattattgc tttatgtgaa    4500
tttgaaaaca tagtaacatc aaaaaaagtc ataataccaa catacctaag atccatcagt    4560
gtcagaaata aagatctgaa cacacttgaa aatataacaa ccactgaatt caaaaatgct    4620
atcacaaatg caaaaatcat cccttactca ggattactat tagtcatcac agtgactgac    4680
aacaaggag cattcaaata cataaagcca caaagtcaat tcatagtaga tcttggagct    4740
tacctagaaa aagaaagtat atattatgtt accacaaatt ggaagcacac agctacacga    4800
tttgcaatca aacccatgga agattaacct ttttcctcta catcagtgtg ttaattcata    4860
caaactttct acctacattc ttcacttcac catcacaatc acaaacactc tgtgtttcaa    4920
ccaatcaaac aaaacttatc tgaagtccca gatcatccca agtcattgtt tatcagatct    4980
agtactcaaa taagttaata aaaaatatac acatggatgc ccatggggca aatgcaaaca    5040
tgtcgaaaaa taaagatcaa cgtacggcga aaacgctaga acgtacgtgg gatacgctaa    5100
atcatctact atttatatcg tcgtgtctat ataaactaaa tctaaaatcg gtagcgcaaa    5160
taacgctatc gatactagcg ataataatat cgacttcgct aataatagcg gcgataatat    5220
ttatagcgtc ggcgaatcat aaagtaacgc cgacgacgcg gataatacaa gatgcgactt    5280
cgcaaataaa aaatacgacg ccgacgtatc taacgcaaaa tccgcaacta ggtatatcgc    5340
cgtcgaatcc gtcggaaata acgtcgcaaa taacgacgat actagcgtcg acgacgccgg    5400
gtgtaaaatc gacgctacaa tcgacgacgg taaaaacgaa aaatacgacg acgacgcaaa    5460
cgcaaccgtc gaaaccgacg acgaaacaac gtcaaaataa accgccgtcg aaaccgaata    5520
atgattttca ttttgaagta tttaattttg taccgtgttc gatatgttcg aataatccga    5580
cgtgttgggc gatatgtaaa cgtataccga ataaaaaacc gggtaaaaaa acgacgacga    5640
aaccgacgaa aaaccgacg ctaaaaacga cgaaaaaaga tccgaaaccg caaacgacga    5700
aatcgaaaga agtaccgacg acgaaaccga cggaagaacc gacgataaat gacgacgaaa    5760
cgaatataat aacgacgcta ctaacgtcga atacgacggg taatccgaa ctaacgtcgc    5820
aaatggaaac gtttcattcg acttcgtcgg aaggtaatcc gtcgccgtcg caagtatcga    5880
cgacttcgga atatccgtcg caaccgtcgt cgccgccgaa tacgccgcgt caatagttac    5940
ttaaaaacat attatcacaa aaggccttga ccaaccgcgg agaatcaaaa taaactctgg    6000
ggcaaataac aatggagttg ccaatcctca agcaaatgca aattaccaca atcctcgctg    6060
cagtcacatt ttgctttgct tctagtcaaa acatcactga agaattttat caatcaacat    6120
gcagtcagt tagcaaaggc tatcttagtg ctctaagaac tggttggtat actagtgtta    6180
taactataga attaagtaat atcaagaaaa ataagtgaa tggaacagat gctaaggtaa    6240
aattgatgaa acaagcagca aacaatcgag ccagagaact accaaggt ttatgaatt     6300
tgcaaagcac accagcagca aacaatcgag ccagagaact accaaggt tttatgaatt     6360
atacactcaa caataccaaa aaaccaatg taacattaag caagaaaagg aaaagaagat    6420
ttcttggttt tttgttaggt gttggatctg caatcgccag tggcattgct gtatctaagg    6480
tcctgcactt agaaggagaa gtgaacaaga tcaaagtgc tctactatcc acaaacaagg    6540
ccgtagtcag cttatcaaat ggagttagtg tcttaaccag cagagtgtta gacctcaaaa    6600
actatataga taaacaattg ttacctattg gaataagctg caaggatcta atatcaaata    6660
tagaaactgt gatagagttc caacaaaaga acaacagact actagagatt accagggaat    6720
ttagtgttaa tgcaggtgta actacacctg taagcactta catgttaact aatagtgaat    6780
tattgtcatt aatcaatgat atgcctaaa caaatgatca gaaaaagtta atgtccaaca    6840
atgttcaaat agttagacag caaagttact ctatcatgtc cataataaaa gaggaagtct    6900
tagcatatgt agtacaatta ccactatatg gtgtgataga tacccttgt tggaaattac    6960
```

```
acacatcccc tctatgtaca accaacacaa aagaagggtc aaacatctgt ttaacaagaa  7020
ctgacagagg atggtactgt gacaatgcag gatcagtatc tttcttccca caagctgaaa  7080
aatgtaaagt tcaatcgaat cgagtatttt gtgacacaat gtacagttta acattaccaa  7140
gtgaagtaaa tctctgcaat gttgacatat tcaatcccaa atatgattgt aaaattatga  7200
cttcaaaaac agatgtaagc agctccgtta tcacatctct aggagccatt gtgtcatgct  7260
atggcaaaac taaatgtaca gcatccaata aaaatcgtgg aatcataaag acattttcta  7320
acgggtgtga ttatgtatca aataaagggg tggacactgt gtctgtaggt aacacattat  7380
attatgtaaa taagcaagaa ggcaaaagtc tctatgtaaa aggtgaacca ataataaatt  7440
tctatgaccc attagtattc ccctctgatg aatttgatgc atcaatatct caagtcaatg  7500
agaagattaa ccagagttta gcatttattc gtaaatccga tgaattatta cataatgtaa  7560
atgctggtaa atcaaccaca aatatcatga taactactat aattatagtg attatagtaa  7620
tattgttatc attaattgct gttggactgc tcctatactg taaggccaga agcacaccag  7680
tcacactaag caaggatcaa ctgagtggta taaataatat tgcatttagt aactgaataa  7740
aaatagcacc taatcatgtt cttacaatgg tttactatct gctcatagac aacccatcta  7800
tcattggatt ttcttaaaat ctgaacttca tcgaaactct tatctataaa ccatctcact  7860
tacactatt aagtagattc ctagtttata gttatataaa acacaattga atgccagtcg  7920
accttaccat ctgtaaaaat gaaaactggg gcaaatatgt cacgaaggaa tccttgcaaa  7980
tttgaaattc gaggtcattg cttaaatggt aagaggtgtc attttagtca taattatttt  8040
gaatggccac cccatgcact gcttgtaaga caaaacttta tgttaaacag aatacttaag  8100
tctatggata aaagtataga taccttatca gaaataagtg gagctgcaga gttggacaga  8160
acagaagagt atgctcttgg tgtagttgga gtgctagaga gttatatagg atcaataaac  8220
aatataacta aacaatcagc atgtgttgcc atgagcaaaa tcctcactga actcaatagt  8280
gatgatatca aaaagctgag ggacaatgaa gagctaaatt cacccaagat aagagtgtac  8340
aatactgtca tatcatatat tgaaagcaac aggaaaaaca ataaacaaac tatccatctg  8400
ttaaaaagat tgccagcaga cgtattgaag aaaaccatca aaaacacatt ggatatccat  8460
aagagcataa ccatcaacaa cccaaaagaa tcaactgtta gtgatacaaa tgaccatgcc  8520
aaaaataatg atactacctg acaaatatcc ttgtagtata acttccatac taataacaag  8580
tagatgtaga gttactatgt ataatcaaaa gaacacacta tatttcaatc aaaacaaccc  8640
aaataaccat atgtactcac cgaatcaaac attcaatgaa atccattgga cctctcaaga  8700
attgattgac acaattcaaa attttctaca acatctaggt attattggga atatatatac  8760
aatatatata ttagtgtcat aacactcaat tctaacactc accacatcgt tacattatta  8820
attcaaacaa ttcaagttgt gggacaaaat ggatcccatt attaatggaa attctgctaa  8880
tgtttatcta accgatagtt attttaaagg tgttatctct ttctcagagt gtaatgcttt  8940
aggaagttac atattcaatg gtcccttatct caaaaatgat tataccaact taattagtag  9000
acaaaatcca ttaatagaac acatgaatct aaagaaacta aatatacac agtcctaat  9060
atctaagtat cataaaggtg aaataaaatt agaagaacct acttattttc agtcattact  9120
tatgacatac aagagtatga cctcgtcaga acagattgct accactaatt tacttaaaaa  9180
gataataaga agagctatag aaataagtga tgtcaaagtc tatgctatat tgaataaact  9240
agggcttaaa gaaaaggaca agattaaatc caacaatgga caagatgaag acaactcagt  9300
tattacgacc ataatcaaag atgatatact ttcagctgtt aaagataatc aatctcatct  9360
taaagcagac aaaaatcact ctacaaaaca aaaagacaca atcaaaacaa cactcttgaa  9420
gaaattgatg tgttcaatgc aacatcctcc atcatggtta atacattggt ttaacttata  9480
cacaaaatta aacaacatat taacacagta tcgatcaaga gaggtaaaaa accatgggtt  9540
tacattgata gataatcaaa ctcttagtgg atttcaattt attttgaacc aatatgggtt  9600
tatagtttat cataaggaac tcaaaagaat tactgtgaca acctataatc aattcttgac  9660
atggaaagat attagcctta gtagattaaa tgtttgttta attacatgga ttagtaactg  9720
cttgaacaca ttaaataaaa gcttaggctt aagatgcgga ttcaataatg ttatcttgac  9780
acaactattc ctttatggag attgtatact aaagctattt cacaatgagg ggttctcat  9840
aataaaagag gtagggat ttattatgtc tctaatttta aatataacag aagaagatca  9900
attcagaaaa cgattttata atagtatgct caacaacatc acagatgctg ctaataaagc  9960
tcagaaaaat ctgctatcaa gagtatgtca tacattata gataagacag tgtccgataa  10020
tataataaat ggcagatgga taattctatt aagtaagttc cttaaattaa ttaagcttgc  10080
aggtgacaat aaccttaaca atctgagtga actatatttt tgttcagaa tatttggaca  10140
cccaatggta gatgaaagac aagccatgga tgctgttaaa attaattgca atgagaccaa  10200
atttttacttg ttaagcagtc tgagtatgtt aagaggtgcc tttatatata gaattataaa  10260
agggtttgta aataattaca acagatggcc tactttaaga aatgctattg ttttaccctt  10320
aagatggtta acttactata aactaaacac ttatccttct ttgttggaac ttacagaaag  10380
agatttgatt gtgttatcag gactacgttt ctatcgtgag tttcggttgc ctaaaaaagt  10440
ggatcttgaa atgattataa atgataaagc tatatcccct cctaaaaatt tgatatggac  10500
tagtttccct agaaattaca tgccatcaca catacaaaac tatatagaac atgaaaaatt  10560
aaaatttttcc gagagtgata aatcaagaag agtattagag tattatttaa gagataacaa  10620
attcaatgaa tgtgatttat acaactgtgt agttaatcaa agttatctca acaaccctaa  10680
tcatgtggta tcattgacag gcaaagaaag agaactcagt gtaggtagaa tgtttgcaat  10740
gcaaccggga atgttcagac aggttcaaat attggcagga aaatgatag ctgaaaacat  10800
tttacaattc tttcctgaaa gtcttacaag atatggtgat ctagaactac aaaaaaatatt  10860
agaattgaaa gcaggaataa gtaacaaatc aaatcgctac aatgataatt acaacaatta  10920
cattagtaag tgctctatca tcacagatct cagcaaattc aatcaagcat ttcgatatga  10980
aacgtcatgt atttgtagtg atgtgctgga tgaactgcat ggtgtacaat ctctattttc  11040
ctggttacat ttaactattc ctcatgtcac aataatatgc acatatagc atgcacccc  11100
ctatatagga gatcatattg tagatcttaa caatgtagat gaacaaagtg gattatatag  11160
atatcacatg ggtggcatcg aagggtggtg tcaaaaactg tggaccatag aagctatatc  11220
actattggat ctaatatctc tcaaagggaa attctcaatt actgctttaa ttaatggtga  11280
caatcaatca atagatataa gcaaaccaat cagactcatg gaaggtcaaa ctcatgctca  11340
gcagattat ttgctagcat taaatagcct taattactgt tataagagct atgcaggcat  11400
aggccacaaa ttaaaggaa ctgagactta tatatcacga gatatgcaat ttatgagtaa  11460
aacaattcaa cataacggtg tatattccc agctagtata aagaaagtcc taagagtggg  11520
accgtgata aacactatac ttgatgattt caaagtgagt ctagaatcta taggtagttt  11580
gacacaagaa ttagaatata gaggtgaaag tctattatgc agtttaatat ttagaaatgt  11640
atggttatat aatcagattg ctctacaatt aaaaaatcat gcattatgta acaataaact  11700
```

```
atatttggac atattaaagg ttctgaaaca cttaaaaacc ttttttaatc ttgataatat  11760
tgatacagca ttaacattgt atatgaattt acccatgtta tttggtggtg gtgatcccaa  11820
cttgttatat cgaagtttct atagaagaac tcctgacttc ctcacagagg ctatagttca  11880
ctctgtgttc atacttagtt attatacaaa ccatgactta aaagataaac ttcaagatct  11940
gtcagatgat agattgaata agttcttaac atgcataatc acgtttgaca aaaaccctaa  12000
tgctgaattc gtaacattga tgagagatcc tcaagcttta gggtctgaga gacaagctaa  12060
aattactagc gaaatcaata gactggcagt tacagaggtt ttgagtacag ctccaaacaa  12120
aatattctcc aaaagtgcac aacattatac tactacagag atagatctaa atgatattat  12180
gcaaaatata gaacctacat atcctcatgg gctaagagtt gtttatgaaa gtttacccct  12240
ttataaagca gagaaaatag taaatcttat atcaggtaca aaatctataa ctaacatact  12300
ggaaaaaact tctgccatag acttaacaga tattgataga gccactgaga tgatgaggaa  12360
aaacataact ttgcttataa ggatacttcc attggattgt aacagagata aaagagagat  12420
attgagtatg gaaaacctaa gtattactga attaagcaaa tatgttaggg aaagatcttg  12480
gtctttatcc aatatagttg gtgttacatc acccagtatc atgtataaca tggacatcaa  12540
atatactaca agcactatat ctagtggcat aattatagag aaatataatg ttaacagttt  12600
aacacgtggt gagagaggac ccactaaacc atgggttggt tcatctacac aagagaaaaa  12660
aacaatgcca gtttataata dacaagtctt aaccaaaaaa cagagagatc aaatagatct  12720
attagcaaaa ttggattggg tgtatgcatc tatagataac aaggatgaat tcatggaaga  12780
actcagcata ggaacccttg ggttaacata tgaaaaggcc aagaaattat ttccacaata  12840
tttaagtgtc aattatttgc atcgccttac agtcagtagt agaccatgtg aattccctgc  12900
atcaatacca gcttatagaa caacaaatta tcactttgac actagcccta ttaatcgcat  12960
attaacagaa aagtaggtg atgacatagta ttccaaaact gtataagctt  13020
tggccttagt ttaatgtcag tagtagaaca atttactagt gtatgtccta acagaattat  13080
tctcatacct aagcttaatg agatacattt gatgaaacct cccatattca caggtgatgt  13140
tgatattcac aagttaaaac aagtgataca aaaacagcat atgttttttac cagacaaaat  13200
aagtttgact caatatgtgg aaattattctt aagtaataaa acactcaaat ctggatctca  13260
tgttaattct aatttaatat tggcacataa aatatctgac tattttcata atacttacat  13320
tttaagtact aatttagctg gacattggat tctgattata caacttatga aagattctaa  13380
aggtattttt gaaaagatt ggggagaggg atatataact gatcatatgt ttattaattt  13440
gaaagtttc ttcaatgctt ataagaccta tctcttgtgt tttcataaag gttatggcaa  13500
agcaaagctg gagtgtgata tgaacacttc agatcttcta tgtgtattgg aattaataga  13560
cagtagttat tggaagtcta tgtctcaaggt attttagaa caaaaagtta tcaaatacat  13620
tcttagccaa gatgcaagtt tacatagagt aaaaggatgt catagcttca aattatggtt  13680
tcttaaacgt cttaatgtag cagaattcac agtttgccct tgggttgtta acatagatta  13740
tcatccaaca catatgaaag caatattaac ttatatgat cttgttagaa tgggattgat  13800
aaatatagat agaatacaca ttaaaaataa acacaaattc aatgatgaat tttatacttc  13860
taatctcttc tacattaatt ataacttctc agataatact catctattaa ctaaacatat  13920
aaggattgct aattctgaat tagaaaataa ttaacaacaaa ttatatcatc ctacaccaga  13980
aacctagag aatatactag ccaatccgat taaaagtaat gacaaaaaga cactgaatga  14040
ctattgtata ggtaaaaatg ttgactcaat aatgttacca ttgttatcta ataagaagct  14100
tattaaatcg tctgcaatga ttagaaccaa ttacagcaaa caagatttgt ataatttatt  14160
ccctatggtt gtgattgata gaattataga tcattcaggc aatacagcca atccaacca  14220
actttacact actacttccc accaaaatatc tttagtgcaa aatagcacat cacttttactg  14280
catgcttcct tggcatcata ttaatagatt caattttgta tttagttcta caggttgtaa  14340
aattagtata gagtatattt taaaagatct taaaattaaa gatcccaatt gtatagcatt  14400
cataggtgaa ggagcaggga atttattatt gcgtacagta gtggaacttc atcctgacat  14460
aagatatatt tacagaagtc tgaaagattg caatgatcat agtttaccta ttgagttttt  14520
aaggctgtac aatggacata tcaacattga ttatggtgaa aatttgacca ttcctgctac  14580
agatgcaacc aacaacattc attggtctta tttacatata aagtttgctg aacctatcag  14640
tcttttttgtc tgtgatgccg aattgtctgt aacagtcaac tggagtaaaa ttataataga  14700
atggcaacaag catgtaagaa agtgcaagta ctgttcctca gttaataaat gtatgttaat  14760
agtaaaatat catgctcaag atgatattga tttcaaatta gacaatataa ctatattaaa  14820
aacttatgta tgcttaggca gtaagttaaa gggatcggag gttacttag tccttacaat  14880
aggtcctgcg aatatattcc cagtatttaa tgtagtacaa aatgctaaat tgatactatc  14940
aagaaccaaa aatttcatca tgcctaagaa agctgataaa gagtctattg atgcaaatat  15000
taaaagtttg atacccttc ttttgttaccc tataacaaaa aaaggaatta atactgcatt  15060
gtcaaaacta aagagtgttg ttagtggaga tatactatca tattctatag ctggacgtaa  15120
tgaagttttc agcaataaac ttataaatca taagcatatg aacatcttaa aatggttcaa  15180
tcatgtttta aatttcagat caacagaact aaactataac catttatata tggaatc  15240
tacatatcct tacctaagtg aattgttaaa cagcttgaca accaatgaac ttaaaaaact  15300
gattaaaatc acaggtagtc tgttatacaa ctttcataat gaataatgaa taaagatctt  15360
ataataaaaa ttcccatagc tatacactaa cactgtattc aattatagtt attaaaaatt  15420
aaaaatcgta cgatttttta aataacttt agtgaactaa tcctaaagtt atcattttaa  15480
tcttggagga ataaatttaa acctaatct aattggttta tatgtgtatt aactaaatta  15540
cgagatatta gttttgaca cttttttct cgt                                 15573

SEQ ID NO: 5             moltype = AA  length = 139
FEATURE                  Location/Qualifiers
VAR_SEQ                  3
                         note = misc_feature - X can be any naturally occurring
                           amino acid
VAR_SEQ                  5
                         note = misc_feature - X can be any naturally occurring
                           amino acid
VAR_SEQ                  8
                         note = misc_feature - X can be any naturally occurring
                           amino acid
VAR_SEQ                  11
                         note = misc_feature - X can be any naturally occurring
```

```
VAR_SEQ              17..18
                     note = misc_feature - X can be any naturally occurring
                         amino acid
VAR_SEQ              31
                     note = misc_feature - X can be any naturally occurring
                         amino acid
VAR_SEQ              36
                     note = misc_feature - X can be any naturally occurring
                         amino acid
VAR_SEQ              45
                     note = misc_feature - X can be any naturally occurring
                         amino acid
VAR_SEQ              57
                     note = misc_feature - X can be any naturally occurring
                         amino acid
VAR_SEQ              64..65
                     note = misc_feature - X can be any naturally occurring
                         amino acid
VAR_SEQ              68
                     note = misc_feature - X can be any naturally occurring
                         amino acid
VAR_SEQ              70
                     note = misc_feature - X can be any naturally occurring
                         amino acid
VAR_SEQ              82
                     note = misc_feature - X can be any naturally occurring
                         amino acid
VAR_SEQ              84
                     note = misc_feature - X can be any naturally occurring
                         amino acid
VAR_SEQ              90
                     note = misc_feature - X can be any naturally occurring
                         amino acid
VAR_SEQ              92..93
                     note = misc_feature - X can be any naturally occurring
                         amino acid
VAR_SEQ              101
                     note = misc_feature - X can be any naturally occurring
                         amino acid
VAR_SEQ              104..106
                     note = misc_feature - X can be any naturally occurring
                         amino acid
VAR_SEQ              115..116
                     note = misc_feature - X can be any naturally occurring
                         amino acid
VAR_SEQ              118
                     note = misc_feature - X can be any naturally occurring
                         amino acid
VAR_SEQ              121
                     note = misc_feature - X can be any naturally occurring
                         amino acid
VAR_SEQ              124
                     note = misc_feature - X can be any naturally occurring
                         amino acid
VAR_SEQ              126..127
                     note = misc_feature - X can be any naturally occurring
                         amino acid
VAR_SEQ              129
                     note = misc_feature - X can be any naturally occurring
                         amino acid
VAR_SEQ              131
                     note = misc_feature - X can be any naturally occurring
                         amino acid
VAR_SEQ              135
                     note = misc_feature - X can be any naturally occurring
                         amino acid
VAR_SEQ              138..139
                     note = misc_feature - X can be any naturally occurring
                         amino acid
source               1..139
                     mol_type = protein
                     organism = respiratory syncytial virus
SEQUENCE: 5
MGXNXLSXIK XRLQNLXXND EVALLKITCY XDKLIXLTNA LAKAXIHTIK LNGIVFXHVI    60
TSSXXCPXNX IVVKSNFTTM PXLXNGGYIX EXXELTHCSQ XNGXXXDNCE IKFSXXLXDS   120
XMTXYXXQXS XLLGXDLXX                                                139

SEQ ID NO: 6         moltype = DNA   length = 420
```

```
FEATURE              Location/Qualifiers
source               1..420
                     mol_type = genomic DNA
                     organism = respiratory syncytial virus
SEQUENCE: 6
atgggttcga attcgctatc gatgataaaa gtacgtctac aaaatctatt tgataatgat    60
gaagtagcgc tactaaaaat aacgtgttat acgataaaac taatacatct aacgaatgcg   120
ctagcgaaag cggtaataca tacgataaaa ctaaatggta tagtatttgt acatgtaata   180
acgtcgtcgg atatatgtcc gaataataat atagtagtaa aatcgaattt tacgacgatg   240
ccggtactac aaaatggtgg ttatatatgg gaaatgatgg aactaacgca ttgttcgcaa   300
ccgaatggtc tactagatga taattgtgaa ataaaatttt cgaaaaaact atcggattcg   360
acgatgacga attatatgaa tcaactatcg gaactactag gttttgatct aaatccgtaa   420

SEQ ID NO: 7         moltype = DNA  length = 420
FEATURE              Location/Qualifiers
source               1..420
                     mol_type = genomic DNA
                     organism = respiratory syncytial virus
SEQUENCE: 7
atggggtcga actcgctctc gatgatcaag gtccgcctcc agaatctctt cgacaacgac    60
gaggtcgcgc tcctcaagat cacgtgttac acggacaagc tcatccacct cacgaacgcg   120
ctcgcgaagg cggtcatcca cacgatcaag ctcaacggga tcgtcttcgt ccacgtcatc   180
acgtcgtcgg acatctgtcc gaacaacaac atcgtcgtca agtcgaactt cacgacgatg   240
ccggtcctcc agaacggggg gtacatctgg gagatgatgg agctcacgca ctgttcgcag   300
ccgaacgggc tcctcgacga caactgtgag atcaagttct cgaagaagct ctcggactcg   360
acgatgacga actacatgaa ccagctctcg gagctcctcg ggttcgacct caacccgtaa   420

SEQ ID NO: 8         moltype = AA  length = 124
FEATURE              Location/Qualifiers
VAR_SEQ              2
                     note = misc_feature - X can be any naturally occurring
                       amino acid
VAR_SEQ              4..8
                     note = misc_feature - X can be any naturally occurring
                       amino acid
VAR_SEQ              10
                     note = misc_feature - X can be any naturally occurring
                       amino acid
VAR_SEQ              12
                     note = misc_feature - X can be any naturally occurring
                       amino acid
VAR_SEQ              14
                     note = misc_feature - X can be any naturally occurring
                       amino acid
VAR_SEQ              21
                     note = misc_feature - X can be any naturally occurring
                       amino acid
VAR_SEQ              23..26
                     note = misc_feature - X can be any naturally occurring
                       amino acid
VAR_SEQ              28
                     note = misc_feature - X can be any naturally occurring
                       amino acid
VAR_SEQ              32..33
                     note = misc_feature - X can be any naturally occurring
                       amino acid
VAR_SEQ              38
                     note = misc_feature - X can be any naturally occurring
                       amino acid
VAR_SEQ              45
                     note = misc_feature - X can be any naturally occurring
                       amino acid
VAR_SEQ              50
                     note = misc_feature - X can be any naturally occurring
                       amino acid
VAR_SEQ              55
                     note = misc_feature - X can be any naturally occurring
                       amino acid
VAR_SEQ              59..60
                     note = misc_feature - X can be any naturally occurring
                       amino acid
VAR_SEQ              68
                     note = misc_feature - X can be any naturally occurring
                       amino acid
VAR_SEQ              72
                     note = misc_feature - X can be any naturally occurring
                       amino acid
VAR_SEQ              76..77
                     note = misc_feature - X can be any naturally occurring
```

|   |   |
|---|---|
| VAR_SEQ | 81 |
|  | note = misc_feature - X can be any naturally occurring amino acid |
| VAR_SEQ | 98 |
|  | note = misc_feature - X can be any naturally occurring amino acid |
| VAR_SEQ | 100 |
|  | note = misc_feature - X can be any naturally occurring amino acid |
| VAR_SEQ | 103 |
|  | note = misc_feature - X can be any naturally occurring amino acid |
| VAR_SEQ | 108 |
|  | note = misc_feature - X can be any naturally occurring amino acid |
| VAR_SEQ | 118 |
| source | 1..124 |
|  | mol_type = protein |
|  | organism = respiratory syncytial virus |

SEQUENCE: 8
```
MXTXXXXXTX QXLXITDMRP XSXXXXXIXSL TXXIITHXFI YLINXECIVX KLDEXQATXX   60
FLVNYEMXLL HXVGSXXYKK XTEYNTKYGT FPMPIFIXHX GFXECIGXKP TKHTPIIXKY  120
DLNP                                                              124
```

| SEQ ID NO: 9 | moltype = DNA  length = 375 |
|---|---|
| FEATURE | Location/Qualifiers |
| source | 1..375 |
|  | mol_type = genomic DNA |
|  | organism = respiratory syncytial virus |

SEQUENCE: 9
```
atggatacga cgcataatga taatacgccg caacgtctaa tgataacgga tatgcgtccg   60
ctatcgctag aaacgataat aacgtcgcta acgcgtgata taataacgca taaatttata  120
tatctaataa atcatgaatg tatagtacgt aaactagatg aacgtcaagc gacgtttacg  180
tttctagtaa attatgaaat gaaactacta cataaagtag gttcgacgaa atataaaaaa  240
tatacggaat ataatacgaa atatggtacg tttccgatgc cgatatttat aaatcatgat  300
ggttttctag aatgtatagg tataaaaccg acgaaacata cgccgataat atataaatat  360
gatctaaatc cgtaa                                                   375
```

| SEQ ID NO: 10 | moltype = DNA  length = 375 |
|---|---|
| FEATURE | Location/Qualifiers |
| source | 1..375 |
|  | mol_type = genomic DNA |
|  | organism = respiratory syncytial virus |

SEQUENCE: 10
```
atggacacga cgcacaacga caacacgccg cagcgcctca tgatcacgga catgcgcccg   60
ctctcgctcg agacgatcat cacgtcgctc acgcgcgaca tcatcacgca caagttcatc  120
tacctcatca accacgagtg tatcgtccgc aagctcgacg agcgccaggc gacgtttcacg 180
ttcctcgtca actacgagat gaagctcctc cacaaggtcg gctcgacgaa gtacaagaag  240
tacacggagt acaacacgaa gtacgggacg ttcccgatgc cgatcttcat caaccacgac  300
gggttcctcg agtgtatcgg gatcaagccg acgaagcaca cgccgatcat ctacaagtac  360
gacctcaacc cgtaa                                                   375
```

| SEQ ID NO: 11 | moltype = AA  length = 30 |
|---|---|
| FEATURE | Location/Qualifiers |
| source | 1..30 |
|  | mol_type = protein |
|  | organism = Homo sapiens |

SEQUENCE: 11
```
TTNIMITTII IVIIVILLSL IAVGLLLYCK                                    30
```

| SEQ ID NO: 12 | moltype = AA  length = 26 |
|---|---|
| FEATURE | Location/Qualifiers |
| source | 1..26 |
|  | mol_type = protein |
|  | organism = Homo sapiens |

SEQUENCE: 12
```
ARSTPVPILK ANAITTILAA VTFCFA                                       26
```

| SEQ ID NO: 13 | moltype = AA  length = 20 |
|---|---|
| FEATURE | Location/Qualifiers |
| source | 1..20 |
|  | mol_type = protein |
|  | organism = Homo sapiens |

SEQUENCE: 13
```
AVTFCFASSQ NITEEFYQST                                              20
```

| SEQ ID NO: 14 | moltype = AA  length = 33 |
|---|---|
| FEATURE | Location/Qualifiers |

```
source                    1..33
                          mol_type = protein
                          organism = Homo sapiens
SEQUENCE: 14
QSTCSAVSKG YLSALRTGWY TSVITIELSN IKK                                   33

SEQ ID NO: 15             moltype = AA   length = 27
FEATURE                   Location/Qualifiers
source                    1..27
                          mol_type = protein
                          organism = Homo sapiens
SEQUENCE: 15
IKKNKCNGTD AKVKLMKQEL DKYKNAV                                          27

SEQ ID NO: 16             moltype = AA   length = 33
FEATURE                   Location/Qualifiers
source                    1..33
                          mol_type = protein
                          organism = Homo sapiens
SEQUENCE: 16
FPQAEKCKVQ SNRVFCDTMY SLTLPSEVNL CNV                                   33

SEQ ID NO: 17             moltype = AA   length = 574
FEATURE                   Location/Qualifiers
source                    1..574
                          mol_type = protein
                          organism = Homo sapiens
SEQUENCE: 17
MELPILKANA ITTILAAVTF CFASSQNITE EFYQSTCSAV SKGYLSALRT GWYTSVITIE       60
LSNIKKNKCN GTDAKVKLMK QELDKYKNAV TELQLLMQST PAANNRARRE LPRFMNYTLN      120
NTKKTNVTLS KKRKRRFLGF LLGVGSAIAS GIAVSKVLHL EGEVNKIKSA LLSTNKAVVS      180
LSNGVSVLTS RVLDLKNYID KQLLPIVNKQ SCRISNIETV IEFQQKNNRL LEITREFSVN      240
AGVTTPVSTY MLTNSELLSL INDMPITNDQ KKLMSNNVQI VRQQSYSIMS IIKEEVLAYV      300
VQLPLYGVID TPCWKLHTSP LCTTNTKEGS NICLTRTDRG WYCDNAGSVS FFPQAEKCKV      360
QSNRVFCDTM YSLTLPSEVN LCNVDIFNPK YDCKIMTSKT DVSSSVITSL GAIVSCYGKT      420
KCTASNKNRG IIKTFSNGCD YVSNKGVDTV SVGNTLYYVN KQEGKSLYVK GEPIINFYDP      480
LVFPSDEFDA SISQVNEKIN QSLAFIRKSD ELLHNVNAGK STTNIMITTI IIVIIVILLS      540
LIAVGLLLYC KARSTPVTLS KDQLSGINNI AFSN                                  574

SEQ ID NO: 18             moltype = DNA   length = 897
FEATURE                   Location/Qualifiers
source                    1..897
                          mol_type = genomic DNA
                          organism = respiratory syncytial virus
SEQUENCE: 18
atgtcgaaaa acaaagacca acgtaccgcg aagacgttag aacgtacctg ggatactcta      60
aatcatttac tattcatatc gtcgtgccta tataagtcac atcttaaatc ggtagcacaa     120
ataacactat ccatactggc gataataatc tcgacttcgc ttataatagc agcgatcata     180
tttatagcct cggcgaacca taaagtcacg ccaacgactg cgatcataca agatgcgaca     240
tcgcagataa agaatacaac gccaacgtac ctaacccaaa atcctcaact tggtatctcg     300
ccctcgaatc cgtctgaaat aacatcgcaa atcacgacgt actagcgtca aacgacaccg     360
ggagtaaagt cgaccctaca atccacgaca gtaaagacga aaaacacgac aacgactcaa     420
acgcaaccct cgaagccgac cacgaaacaa cgccaaaata accaccgag caaaccgaat      480
aatgattttc actttgaagt attcaatttt gtaccctgta gcatatgtag caataatcca     540
acgtgctggg cgatctgtaa aagaataccg aacaaaaaac cgggaaaaaa aaccacgaac     600
aaacccacga aaaaccaac gctcaaaaca acgaaaaag atcccaaacc gcaaccacg         660
aaatcaaaag aagtacccac gaccaaaccc acggaagagc cgaccataaa cacgaccaaa     720
acgaacataa taactacgct actcacgtcc aataccacgg gaaatccgga actcacgagt     780
caaatggaaa cgtttcactc gacttcgtcc gaaggtaatc catcgccttc gcaagtctcg     840
acaacgtccg aatacccgtc acaacgtca tcgccaccga cacgccacg tcagtag          897

SEQ ID NO: 19             moltype = DNA   length = 897
FEATURE                   Location/Qualifiers
source                    1..897
                          mol_type = genomic DNA
                          organism = respiratory syncytial virus
SEQUENCE: 19
atgtcgaaaa ataaagacca acgtacggcg aagacgctag aacgtacctg ggatacgcta      60
aatcatttac tatttatatc gtcgtgccta tataaactaa atcttaaatc ggtagcgcaa     120
ataacactat cgatactggc gataataata tcgacttcgc taataatagc agcgataata     180
tttatagcct cggcgaatca taaagtcacg ccgacgactg cgataataca agatgcgaca     240
tcgcaaataa agaatacgac gccaacgtat ctaacccaaa atccgcaact tggtatatcg     300
ccctcgaatc cgtcggaaat aacatcgcaa ataacgacca tactagcgtc gacgacaccg     360
ggtgtaaagt cgacgctaca atccacgacg gtaaagcgaa aaatacgac acgacgcaa       420
acgcaaccgt cgaaaccgac cacgaaacaa cgtcaaaata accaccgtc gaaaccgaat      480
aatgattttc actttgaagt atttaatttt gtaccctgtt cgatatgtag caataatccg     540
acgtgctggg cgatatgtaa aagaataccg aataaaaaac cgggaaaaaa aacgacgacc     600
aaaccgacga aaaaccaac gctaaaaaca acgaaaaaag atccgaaacc gcaaccacg        660
aaatcgaaag aagtacccac gacgaaaccc acggaagaac cgaccataaa tacgaccaaa     720
```

```
acgaatataa taactacgct actaacgtcc aatacgacgg gaaatccgga actaacgagt   780
caaatggaaa cgtttcattc gacttcgtcg gaaggtaatc catcgccgtc gcaagtctcg   840
acgacttccg aatatccgtc acaaccgtcg tcgccaccga atacgccacg tcaatag      897

SEQ ID NO: 20          moltype = DNA  length = 897
FEATURE                Location/Qualifiers
source                 1..897
                       mol_type = genomic DNA
                       organism = respiratory syncytial virus
SEQUENCE: 20
atgtcgaaaa ataagatca acgtacggcg aaaacgctag aacgtacgtg ggatacgcta    60
aatcatctac tatttatatc gtcgtgtcta tataaactaa atctaaaatc ggtagcgcaa   120
ataacgctat cgatactagc gataataata tcgacttcgc taataatagc ggcgataata   180
tttatagcgt cggcgaatca taaagtaacg ccgacgacgg cgataataca agatgcgact   240
tcgcaaataa aaaatacgac gccgacgtat ctaacgcaaa atccgcaact aggtatatcg   300
ccgtcgaatc cgtcggaaat aacgtcgcaa ataacgacga tactagcgtc gacgacgccg   360
ggtgtaaaat cgacgctaca atcgacgacg gtaaaaacga aaaatacgac gacgacgcaa   420
acgcaaccgt cgaaaccgac gacgaaacaa cgtcaaaata aaccgccgtc gaaaccgaat   480
aatgattttc attttgaagt atttaatttt gtaccgtgtt cgatatgttc gaataatccg   540
acgtgttggg cgatatgtaa acgtataccg aataaaaaac cgggtaaaaa aacgacgacg   600
aaaccgacga aaaaccgac  gctaaaaacg acgaaaaaag atccgaaacc gcaaacgacg   660
aaatcgaaag aagtaccgac gacgaaaccg acggaagaac cgacgataaa tacgacgaaa   720
acgaatataa taacgacgct actaacgtcg aatacgacgg gtaatccgga actaacgtcg   780
caaatggaaa cgtttcattc gacttcgtcg gaaggtaatc cgtcgccgtc gcaagtatcg   840
acgacttcgg aatatccgtc gcaaccgtcg tcgccgccga atacgccgcg tcaatag      897

SEQ ID NO: 21          moltype = AA  length = 574
FEATURE                Location/Qualifiers
source                 1..574
                       mol_type = protein
                       organism = respiratory syncytial virus
SEQUENCE: 21
MELPILKANA ITTILAAVTF CFASSQNITE EFYQSTCSAV SKGYLSALRT GWYTSVITIE    60
LSNIKENKCN GTDAKVKLMK QELDKYKNAV TELQLLMQST PAANNRARRE LPRFMNYTLN   120
NTKKTNVTLS KKRKRRFLGF LLGVGSAIAS GIAVSKVLHL EGEVNKIKSA LLSTNKAVVS   180
LSNGVSVLTS RVLDLKNYID KQLLPIVNKQ SCRISNIETV IEFQQKNNRL LEITREFSVN   240
AGVTTPVSTY MLTNSELLSL INDMPITNDQ KKLMSNNVQI VRQQSYSIMS IIKEEVLAYV   300
VQLPLYGVID TPCWKLHTSP LCTTNTKEGS NICLTRTDRG WYCDNAGSVS FFPQAEKCKV   360
QSNRVFCDTM YSLTLPSEVN LCNVDIFNPK YDCKIMTSKT DVSSSVITSL GAIVSCYGKT   420
KCTASNKNRG IIKTFSNGCD YVSNKGVDTV SVGNTLYYVN KQEGKSLYVK GEPIINFYDP   480
LVFPSDEFDA SISQVNEKIN QSLAFIRKSD ELLHNVNAGK STTNIMITTI IIVIIVILLS   540
LIAVGLLLYC KARSTPVTLS KDQLSGINNI AFSN                              574
```